(12) United States Patent
Casey et al.

(10) Patent No.: US 10,870,704 B2
(45) Date of Patent: Dec. 22, 2020

(54) CD83 BINDING PROTEINS AND USES THEREOF

(71) Applicant: KIRA BIOTECH PTY LIMITED, Fortitude Valley (AU)

(72) Inventors: Joanne L. Casey, Greensborough (AU); Andrew M. Coley, Greensborough (AU)

(73) Assignee: KIRA BIOTECH PTY LIMITED, Fortitude Valley (AU)

(*) Notice: Subject to any disclaimer, the term of this patent is extended or adjusted under 35 U.S.C. 154(b) by 474 days.

(21) Appl. No.: 15/521,124

(22) PCT Filed: Oct. 23, 2015

(86) PCT No.: PCT/AU2015/000635
§ 371 (c)(1),
(2) Date: Apr. 21, 2017

(87) PCT Pub. No.: WO2016/061617
PCT Pub. Date: Apr. 28, 2016

(65) Prior Publication Data
US 2017/0335006 A1 Nov. 23, 2017

(30) Foreign Application Priority Data
Oct. 23, 2014 (AU) ................ 2014904236

(51) Int. Cl.
C07K 16/28 (2006.01)
A61K 39/395 (2006.01)
A61K 47/68 (2017.01)

(52) U.S. Cl.
CPC ........ *C07K 16/2896* (2013.01); *A61K 39/395* (2013.01); *C07K 16/2803* (2013.01); *C07K 2317/21* (2013.01); *C07K 2317/515* (2013.01); *C07K 2317/55* (2013.01); *C07K 2317/56* (2013.01); *C07K 2317/92* (2013.01)

(58) Field of Classification Search
CPC ............ C07K 16/2896; C07K 16/2803; C07K 2317/21; C07K 2317/515; C07K 2317/55; C07K 2317/56; C07K 2317/92; A61K 39/395; A61K 47/6887; A61P 3/10; A61P 37/06; A61P 37/00; A61P 35/00; A61P 31/18
See application file for complete search history.

(56) References Cited

U.S. PATENT DOCUMENTS

| | | |
|---|---|---|
| 4,554,101 A | 11/1985 | Hopp |
| 4,593,089 A | 6/1986 | Wang et al. |
| 4,676,980 A | 6/1987 | Segal et al. |
| 4,751,190 A | 6/1988 | Chiapetta et al. |
| 4,816,397 A | 3/1989 | Boss et al. |
| 4,816,567 A | 3/1989 | Cabilly et al. |
| 4,946,778 A | 8/1990 | Ladner et al. |
| 5,225,539 A | 7/1993 | Winter |
| 5,260,203 A | 11/1993 | Ladner et al. |
| 5,316,920 A | 5/1994 | Tedder et al. |
| 5,516,637 A | 5/1996 | Huang et al. |
| 5,565,332 A | 10/1996 | Hoogenboom et al. |
| 5,571,728 A | 11/1996 | Kraus |
| 5,585,089 A | 12/1996 | Queen et al. |
| 5,731,168 A | 3/1998 | Carter et al. |
| 5,807,715 A | 9/1998 | Morrison et al. |
| 5,837,821 A | 11/1998 | Wu |
| 5,844,094 A | 12/1998 | Hudson et al. |
| 5,885,793 A | 3/1999 | Griffiths et al. |
| 6,054,297 A | 4/2000 | Carter et al. |
| 6,113,898 A | 9/2000 | Anderson et al. |
| 6,204,023 B1 | 3/2001 | Robinson et al. |
| 6,248,516 B1 | 6/2001 | Winter et al. |
| 6,248,597 B1 | 6/2001 | Eda et al. |
| 6,291,158 B1 | 9/2001 | Winter et al. |
| 6,300,064 B1 | 10/2001 | Knappik et al. |
| 6,331,415 B1 | 12/2001 | Cabilly et al. |
| 6,423,538 B1 | 7/2002 | Wittrup et al. |
| 6,602,684 B1 | 8/2003 | Umana et al. |
| 6,737,056 B1 | 5/2004 | Presta |
| 7,083,784 B2 | 8/2006 | Dall'Acqua et al. |
| 7,205,159 B2 | 4/2007 | Cole et al. |
| 7,217,797 B2 | 5/2007 | Hinton et al. |
| 7,217,798 B2 | 5/2007 | Hinton et al. |
| 7,270,969 B2 | 9/2007 | Watt et al. |
| 7,317,091 B2 | 1/2008 | Lazar et al. |
| 7,355,008 B2 | 4/2008 | Stavenhagen et al. |
| 7,563,442 B2 | 7/2009 | Bedian et al. |
| 7,566,771 B1 | 7/2009 | Adair et al. |
| 7,732,578 B2 | 6/2010 | Foote |

(Continued)

FOREIGN PATENT DOCUMENTS

| | | |
|---|---|---|
| EP | 0 569 141 | 11/1993 |
| EP | 2 258 724 | 12/2010 |

(Continued)

OTHER PUBLICATIONS

Rudikoff et al., PNAS 79: 1979-1983 (Year: 1982).*
Chen et al., EMBO J., 14: 2784-2794 (Year: 1995).*
Chien et al., Proc. Natl. Acad. Sci USA. 86 (14): 5532-5536 (Year: 1989).*
Caldas et al., Mol Immunol 39 (15): 941-952 (Year: 2003).*
Stancovski et al., Proceedings of the National Academy of Science USA 88: 8691-8695 (Year: 1991).*
Sarantakis, et al.; "A. Novel Cyclic Undecapeptide, WY-40,770, with Prolonged Growth Hormone Release Inhibiting Activity", Biochem. Biophys. Res. Commun., vol. 73, pp. 336-342 (1976).

(Continued)

*Primary Examiner* — Phuong Huynh
(74) *Attorney, Agent, or Firm* — Finnegan, Henderson, Farabow, Garrett & Dunner, LLP

(57) ABSTRACT

An isolated or recombinant CD83 binding protein may include an antigen binding domain, wherein the antigen binding domain binds specifically to CD83 or a cell expressing CD83.

17 Claims, 5 Drawing Sheets

Specification includes a Sequence Listing.

(56) References Cited

U.S. PATENT DOCUMENTS

| | | | |
|---|---|---|---|
| 8,197,809 | B2 | 6/2012 | Park et al. |
| 9,840,559 | B2 | 12/2017 | Seldon et al. |
| 2003/0124619 | A1 | 7/2003 | Weigl et al. |
| 2004/0116338 | A1 | 6/2004 | Steinkasserer et al. |
| 2004/0185040 | A1 | 9/2004 | Gracia-Martinez et al. |
| 2004/0228761 | A1 | 11/2004 | Owens et al. |
| 2004/0265926 | A1 | 12/2004 | Ng |
| 2005/0123546 | A1 | 6/2005 | Umana et al. |
| 2007/0135620 | A1 | 6/2007 | Chamberlain et al. |
| 2007/0190051 | A1 | 8/2007 | Bedian et al. |
| 2007/0292416 | A1 | 12/2007 | Rother et al. |
| 2008/0095767 | A1 | 4/2008 | Jennings et al. |
| 2008/0152586 | A1 | 6/2008 | Hudson et al. |
| 2009/0041770 | A1 | 2/2009 | Chamberlain et al. |
| 2009/0247455 | A1 | 10/2009 | Fear |
| 2010/0062489 | A1 | 3/2010 | Guehenneux et al. |
| 2010/0226912 | A1 | 9/2010 | Mehtali |
| 2014/0271617 | A1* | 9/2014 | Igawa .............. G01N 33/6854 424/130.1 |

FOREIGN PATENT DOCUMENTS

| | | |
|---|---|---|
| EP | 2 726 509 | 1/2013 |
| WO | WO 95/29236 | 11/1995 |
| WO | WO 1997/30087 | 8/1997 |
| WO | WO 1999/22764 | 5/1999 |
| WO | WO 99/58661 | 11/1999 |
| WO | WO 00/34317 | 6/2000 |
| WO | WO 03/045318 | 6/2003 |
| WO | WO 2004/016284 | 2/2004 |
| WO | WO 2004/048552 A2 | 6/2004 |
| WO | WO 2007/150020 | 12/2007 |
| WO | WO 2010/059821 | 5/2010 |
| WO | WO 2012/088290 | 6/2012 |
| WO | WO 2013/006505 A1 | 1/2013 |
| WO | WO 2014/117220 | 8/2014 |
| WO | WO 2014/117220 A1 | 8/2014 |

OTHER PUBLICATIONS

Merrifield; "Solid Phase Peptide Synthesis, I. The Synthesis of a Tetrapeptide", J. Am. Chem. Soc., vol. 85, pp. 2149-2154 (1963).
Bodanszky: "In Search of New Methods in Peptides Systhesis", Int. J. Peptide Protein Res., vol. 25, pp. 449-474 (1985).
Chothia et al.; "Canonical Structures for the Hypervariable Regions of Immunoglobulins", Jour. Mol. Biol., vol. 196 pp. 901-917 (1987).
Chothia et al.; "Conformations of Immunoglobulin Hypervariable Regions", Nature, vol. 342, pp. 877-883 (1989).
Al-Lazikani et al.; "Standard Conformations for the Canonical Structures of Immunoglobulins", J. Mol. Biol. vol. 273, pp. 927-948 (1997).
Honegger et al., "Yet Another Numbering Scheme for Immunoglobulin Variable Domains: An Automatic Modeling and Analysis Tool", J. Mol. Biol., vol. 309, pp. 657-670 (2001).
Guidicelli et al.; "IMGT, the International ImMunoGeneTics Database", Nucleic Acids Res., vol. 25, pp. 206-211 (1997).
Padian et al.; "Identification of Specificity-Determining Residues in Antibodies", FASEB J., vol. 9, pp. 133-139 (1995).
Jones et al.; "A Method for Rapid, Ligation-Independent Reformatting of Recombinant Monoclonal Antibodies", J. Immunol, Methods, vol. 354, pp, 85-90 (2010).
Jostock et al.; "Rapid Generation of Functional Human IgG Antibodies Derived from Fab-On-Phage Display Libraries", J. Immunol. Methods, vol. 289, pp. 65-80 (2004).
Shalaby et al.; "Development of Humanized Bispecific Antibodies Reactive with Cytotoxic Lymphocytes and Tumor Cells Overexpressing the HER2 Protooncogene", J. Exp. Med., vol. 175, pp. 217-225 (1992).
Hellstrom et al.; "Antitumor Effects of L6, and IgG2a Antibody that Reacts with most Human Carcinomas", Proc. Natl. Acad. Sci. USA, vol. 83, pp. 7059-7063 (1986).

Bruggemann et al.; "Comparison of the Effector Functions of Human Immunoglobulins Using a Matched Set of Chimeric Antibodies", J. Exp. Med., vol. 166, pp. 1351-1361 (1987).
Gazzano-Santoro et al.; "A Non-Radioactive Complement-Dependent Cytotoxicity Assay for Anti-CD20 Monoclonal Antibody", J. Immunol. Methods, vol. 202, pp. 163-171 (1997).
Needleman et al.; "A General Method Applicable to the Search for Similaritiesn the Amino Acid Sequence of Two Proteins", J. Mol. Biol., vol. 48, pp. 443-453 (1970).
Kyte et al.; "A Simple Method for Displaying the Hydropathic Character of a Protein", J. Mol. Biol., vol. 157, , pp. 105-132 (1982).
Thie et al.; "Affinity Maturation by Phage Display", Methods Mol. Biol., vol. 525, pp. 309-322 (2009).
Kopsidas et al.; "In Vitro Improvement of a Shark IgNAR Antibody by Qβ Replicase Mutation and Ribosome Display Mimics In Vivo Affinity Maturation", Immunol. Lett., vol. 107, pp. 163-168 (2006).
Kopsidas et al.; "RNA Mutagenesis Yields Highly Diverse mRNA Libraries for In Vitro Protein Evolution", BMC Biotechnology, vol. 7, No. 18, pp. 1-12 (2007).
Stemmer; "Rapid Evolution of a Protein In Vitro by DNA Shuffling", Nature, vol. 370, pp. 389-391 (1994).
Marsh et al.; "Expanded Polyglutamine Peptides Alone are Intrinsically Cytotoxic and Cause Neurodegeneration in *Drosophila*", Hum. Mol. Genet, vol. 9, pp. 13-25 (2000).
Kanai et al.; "$T_H^{1/T}{}_H2$-Mediated Colitis Induced by Adoptive Transfer of $CD4^+CD45RB^{high}T$ Lymphocytes into Nude Mice", Inflamm. Bowel Dis., vol. 12, No. 2, pp. 89-99 (2006).
Tsunoda et al.; "Two Models for Multiple Sclerosis: Experimental Allergic Encephalomyelitis and Theiler's Murine Encephalomyelitis Virus", J. Neuropathol. Exp. Neurol., vol. 55, No. 6, pp. 673-686 (1996).
Sakaguchi et al.; "Altered Thymic T-Cell Selection Due to a Mutation of the ZAP-70 Gene Causes Autoimmune Arthritis in Mice", Nature, vol. 426, pp. 454-460 (1995).
Bendele; "Animal Models of Rheumatoid Arthritis", J. Musculoskel. Neuron. Interact., vol. 1, pp. 377-385 (2001).
Kim et al.; "Localization of the Site of the Murine IgG1 Molecule that is Involved in Binding to the Murine Intestinal Fc Receptor", Eur. J. Immunol., vol. 24, pp. 2429-2434 (1994).
Kim et al.; "Identifying Amino Acid Residues that Influence Plasma Clearance of Murine IgG1 Fragments by Site-Directed Mutagenesis", Eur. J. Immunol., vol. 24, pp. 542-548 (1994).
De Heard et al.; "A Large Non-Immunized Human Fab Fragment Phage Library that Permits Rapid Isolation and Kinetic Analysis of High Affinity Antibodies", J. Biol. Chem., vol. 274, No. 26, pp. 18218-18230 (1999).
Munster et al.; "Human T Lymphoblasts and Activated Dendritic Cells in the Allogeneic Mixed Leukocyte Reaction are Susceptible to NK Cell-Mediated Anti-CD83-Dependent Cytotoxicity", Int. Immunol., vol. 16. No. 1, pp. 33-42 (2004).
Dudziak et al.; "Alternative Splicing Generates Putative Soluble CD83 Proteins that Inhibit T Cell Proliferation", J. Immunol., pp. 6672-6676 (2005).
Hock et al.; "A Soluble Form of CD83 is Released from Activated Dendritic Cells and B Lymphocytes, and is Detectable in Normal Human Sera", Int. Immunol., vol. 13, No. 7, pp. 959-967 (2001).
Marks et al., "By-Passing Immunization: Building High Affinity Antibodies by Chain Shuffling" Nature Biotech., vol. 10, pp. 779-783 (1992).
Harmsen et al.; "Properties, Production, and Applications of Camelid Single-Domain Antibody Fragments", Appl. Microbiol. Biotechnol., vol. 77, pp. 13-22 (2007).
Wu et al.; "The AKT Axis as a Therapeutic Target in Autoimmune Diseases", vol. 9, pp. 145-150 (2009).
Zinser et al.; "Prevention and Treatment of Experimental Autoimmune Encephalomyelitis by Soluble CD83", J. Exp. Med., vol. 200, No. 3, pp. 345-351 (2004).
Munster et al.; "A Potential New Target for Immunosuppression", Blood, vol. 100, No. 11, Abstract No. 3694, pp. 57b (2002).
Seldon et al.; "Improved Protein-A Separation of $V_H3$ Fab from Fc after Papain Digestion of Antibodies", Jour. Biomol. Tech., vol. 22, pp. 50-52 (2011).

(56) References Cited

OTHER PUBLICATIONS

Wilson et al.; "Antibody to the Dendritic Cell Surface Activation Antigen CD83 Prevents Acute Graft-Versus-Host Disease", J. Exp. Med., vol. 206, No. 2, pp. 387-398 (2009).
Seldon et al.; "Immunosuppressive Human Anti-CD83 Monoclonal Antibody Depletion of Activated Dendritic Cells in Transplantation", Leukemia, vol. 30, pp. 692-700 (2016).
Chen et al.; "Two Novel Monoclonal Antibodies Produced Against Human CD83 Molecule", Hybridoma, vol. 30, No. 3, pp. 297-302 (2011).
Hart et al.; "Developing a Therapeutic Anti-Dendritic Cell Antibody to Prevent Graft Versus Host Disease", Blood. vol. 114, Supplement 22, Abstract 3554, 2 pages (2009).
Database Geneseq (online) "Human DP-46 Heavy Chain Variable Region", EBI Accession No. GSP: AAM51167, 2 pages (2002).
Genbank Accession No. ABI35683.1, Immunoglobulin Heavy Chain Variable Region, Partial [*Homo Sapiens*], 1 page (2007).
Genbank Accession No. ACF37389, Immunoglobulin Heavy Chain Variable Region, Partial [*Homo Sapiens*], 1 page (2009).
D. Hart et al., Abstract No. D2342, "The Monoclonal Antibody 3C12C, Targeting CD83 Is a T Cell Sparing Potential New Immunosuppressive Agent," The American Society of Transplant Surgeons, The Transplantation Society and the American Society of Transplantation, vol. 98, Suppl. 1, p. 390 (2014).
D. Hart et al., Abstract 3554, "Developing a Therapeutic Anti-Dendritic Cell Antibody to Prevent Graft Versus Host Disease," Blood, vol. 114, Suppl. 22, (2009).
J. Wilson et al., "Antibody to the Dendritic Cell Surface Activation Antigen CD83 Prevents Acute Graft-Versus-Host Disease," J. Exp. Med., vol. 206, No. 2, pp. 387-398 (Feb. 16, 2009).
Benny (2004) "Antibody Engineering: Methods and Protocols", Humana Press, vol. 248. (Textbook cover provided.).
Chang et al., (2015) "High Levels of Regulatory T cells in blood are poor prognostic factor in patients with diffuse large B cell lymphoma", *Am. J. Clin. Pathol.*, 144(6):935-944.
Gietz et al., (1991) "Applications of high efficiency lithium acetate transformation of intact yeast cells using single-stranded nucleic acids as carrier", *Yeast*, 7(3):253-263.
Harlow and Lane, (1988) "Antibodies: A Laboratory Manual", Cold Spring Harbor Laboratory Press, Cold Spring Harbor, New York. (Textbook cover provided.).
Hart et al., (2014) "The Monoclonal Antibody 3C12C, Targeting CD83 Is a T Cell Sparing, Potential New Immunosuppressive Agent", *Transplantation*, 98:390 (Abstract D2342).
Honegger et al., (2001) "Yet another numbering scheme for immunoglobulin variable domains: an automatic modeling and analysis tool", *J. Mol. Biol.*, 309(3):657-670.
Hoogenboom et al., (1991) "Multi-subunit proteins on the surface of filamentous phage: methodologies for displaying antibody (Fab) heavy and light chains", *Nucleic Acids Res.*, 19(15):4133-4137.
International Search Report, International Application No. PCT/AU2014/000066 for TRANSBIO Ltd et al., dated Apr. 11, 2014 (7 pages).
Kanda et al., (2007) "Establishment of a GDP-mannose 4,6-dehydratase (GMD) knockout host cell line: a new strategy for generating completely non-fucosylated recombinant therapeutics", *J. Biotechnol.*, 130(3):300-310.
Khader et al., (2016) "The utility of fascin and CD83 in the differential diagnosis of mediastinal large B cell lymphoma", *Virchows Archives*, 469(Suppl 1):S111 (Abstract PS-11-002).
Li et al., (2018) "CD83 is a new potential biomarker and therapeutic target for Hodgkin lymphoma", *Haematologica*, 103(4):655-665.
Mori et al., (2004) "Engineering Chinese hamster ovary cells to maximize effector function of produced antibodies using FUT8 siRNA", *Biotechnol. Bioeng.*, 88(7):901-908.
Natsume et al., (2008) "Engineered antibodies of IgG1/IgG3 mixed isotype with enhanced cytotoxic activities", *Cancer Res.*, 68(10):3863-3872.
Orr-Weaver et al., (1983) "Multiple, tandem plasmid integration in *Saccharomyces cerevisiae*", *Mol. Cell Biol.*, 3(4):747-749.
Serke et al., (1998) "Quantitative fluorescence flow cytometry: a comparison of the three techniques for direct and indirect immunofluorescence", *Cytometry*, 33(2):179-187.
Sheets et al., (1998) "Efficient construction of a large nonimmune phage antibody library: the production of high-affinity human single-chain antibodies to protein antigens", *Proc. Natl. Acad. Sci. U.S.A.*, 95(11):6157-6162.
Supplementary European Search Report, European Application No. 14745637 entitled "Anti-CD83 Antibodies and Use Thereof", dated Sep. 20, 2016 (2 pages).
Umana et al., (1999) "Engineered glycoforms of an antineuroblastoma IgG1 with optimized antibody-dependent cellular cytotoxic activity", *Nat. Biotechnol.*, 17(2):176-180.
Yamane-Ohnuki et al., (2004) "Establishment of FUT8 knockout Chinese hamster ovary cells: an ideal host cell line for producing completely defucosylated antibodies with enhanced antibody-dependent cellular cytotoxicity", *Biotechnol. Bioeng.*, 87(5):614-622.
Zhou et al., (1995) "Human blood dendritic cells selectively express CD83, a member of the immunoglobulin superfamily", *J. Immunol.*, 154(8):3821-3835.
Zhou et al., (2010) "Internalizing cancer antibodies from phage libraries selected on tumor cells and yeast-displayed tumor antigens", *J. Mol. Biol.*, 404(1):88-99.

\* cited by examiner

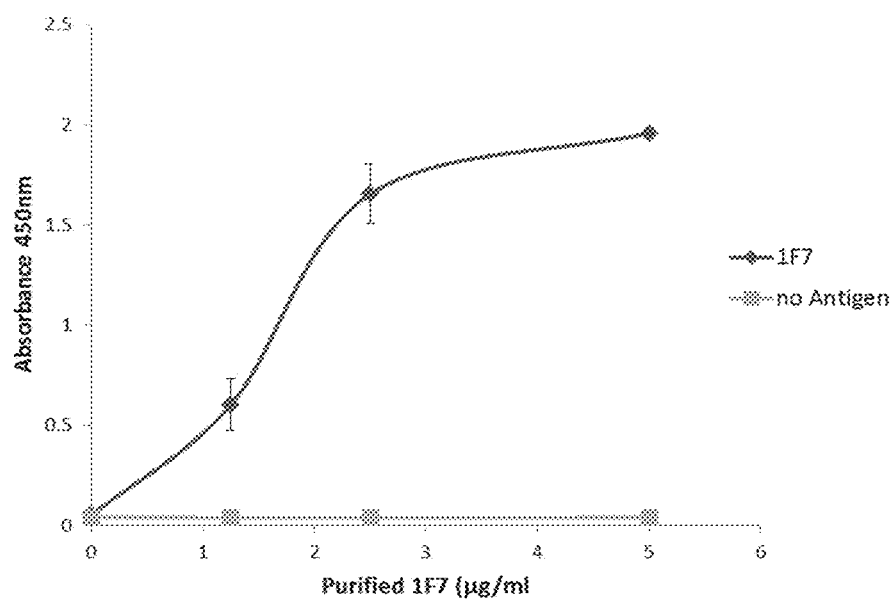
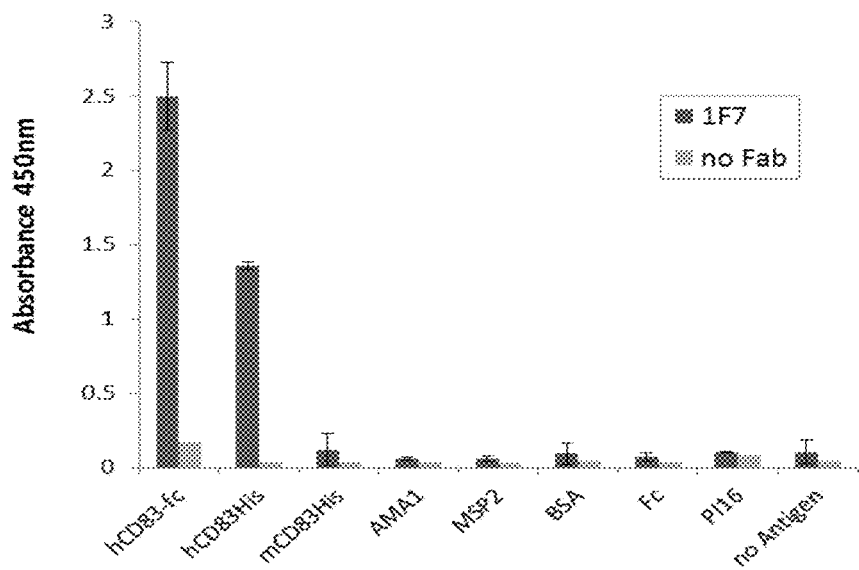
FIGURE 2

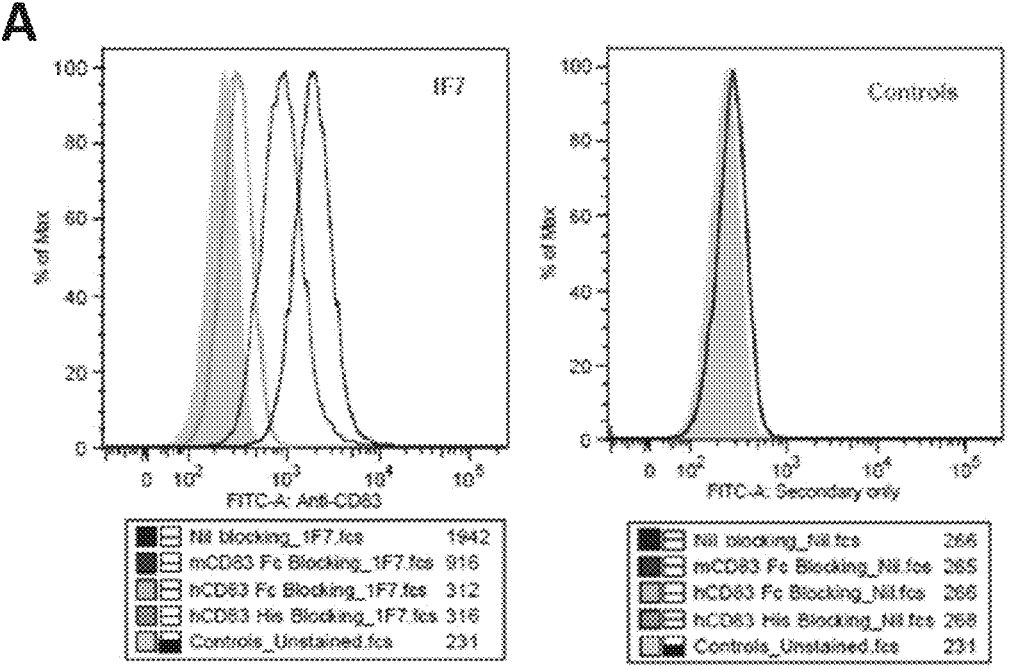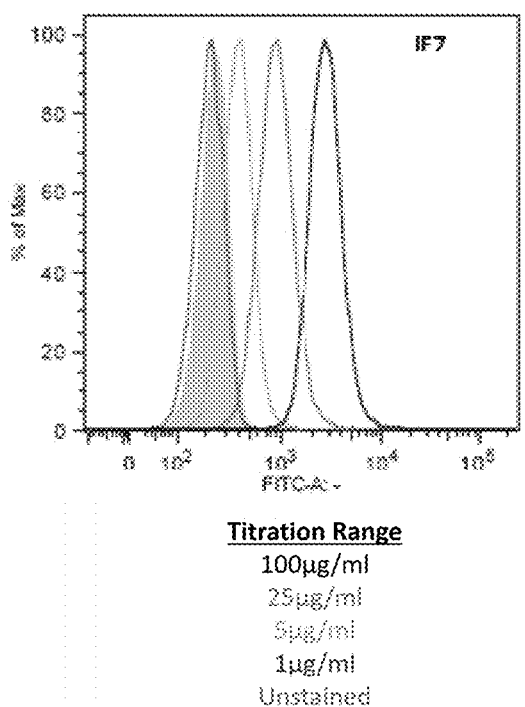
FIGURE 3

|          | FR1                              | CDR1                    | FR2                | CDR2      | FR3                                              | CDR3              | FR4           |
|----------|----------------------------------|-------------------------|--------------------|-----------|--------------------------------------------------|-------------------|---------------|
| wt1F7    | LFQPPSASGTPGQRVTISC              | SGSSSNIGSNTVN           | WYQQLPGTAPKLLIY    | GNDQRP    | SGVPDRFSASKSGTSASLAISGLQSEDEAHYC                 | AAWDGSLNGGVI      | FGGGTKVTVLG   |
| hFab 4.1 | VTQPPSASGTPGQRVTISC               | SGSSSNIGTNPVN           | WYQQLPGTAPKLLIY    | TTEQRP    | SGVPDRFSGSKSGTSASLAISGLQSEDEADYC                 | AAWDDSLSGLIV      | FGTGTKVTVLG   |
| hFab 4.2 | MRHTPLSLSVTPGQPASISC              | KSSQSLLHSDGKTYLY        | WYLQRPGQSPQRLIY    | EVSNRF    | SGVPDRFSGSGSGTDFTLKISRVEAEDVGVYC                 | MQSLQLWT          | FGQGTKVEIKR   |
| hFab 4.3 | MTQSPLSLPVTLGQPASISC              | RSSQSLIHSDGNTYLD        | WFQQRPGQSPRRLIY    | KVSNRD    | SGVPDRFSGSGSGTDFTLRISRVEAEDIGVYC                 | MQATHWPRT         | FGQGTKVEIKR   |
| hFab 4.4 | MTQSPLSLPVTLGQPASISC              | RSSQSLVDSAGNTFLH        | WFHQRPGQSPRRLIY    | KVSNRD    | SGVPDRFSGSGSGTDFTLKISRVEAEDVGVYC                 | MQGTHWPRT         | FGQGTKVEIKR   |
| hFab 4.5 | LTQSPLSLPVTLGQPASISC              | KSSQSLVDSDGNTYLN        | WFQQRPGQSPRRLIY    | KVSNRD    | SGVPDRFSGSGSGTDFTLKISRVEAEDVGVYC                 | MQGTHWPRT         | FGQGTKVEIKR   |
| hFab 4.7 | MTQSPLSLPVTLGQPASISC              | RSSQSLVHSDGNMYLN        | WFQQRPGQSPRRLIY    | KVSNRD    | SGVPDRFSGSGSGTDFTLKISRVEAEDVGVYC                 | MQATQPTWT         | FGQGTKLEIKR   |
| hFab 4.8 | MTQSPSSLSASVGDRVTITC              | QASQDISNYLN             | WYQQKPGKAPKLLIY    | DASNLE    | TGVPSRFSGSRFSGSGSGTDFTFTISSLQPDDFATYC            | QQTYSWPRT         | FGQGTKVEIKR   |
| hFab 4.9 | MTQSPSSLSASVGHPVTITC              | RASQSLISYLN             | WYHQKPGKAPKLLIY    | AASILQ    | SGVPSRFSGSGSGTDFTLTISSLQPENFASYC                 | QHTDSFPRT         | FGHGTKVEIKE   |
| hFab 4.10| LTQPPSASGTPGQRVTISC               | RGSTSNIGNWVN            | WYHVPGSAEKLLIW     | SNIQRP    | SGIPDRFSGSKSGTSASLAISGLQSEDEBAVYC                | AVWDDGLASWV       | FGGGTTVTVLS   |
| hFab 4.12| MTQAPVVSVALEQTVRITC               | QGDSLAIYDF              | WYQHRPGQAPVLVIY    | GKNNRP    | SGIPHRFSGSSS-NTDSLIITGAQAEDEADYC                 | NSRDSSGNHWV       | FGGGTNLTVLG   |
| hFab 4.18| LTQSPLSLPVTLGQPASISC              | KSNQSLVHSDGNTYLN        | WFQQRPGQSPRRLIY    | KVSNRD    | SGVPDRFSGSGSGTDFTLKINRVEAEDVGVYC                 | MQGTQWPRT         | FGQGTKLDIKE   |

FIGURE 4

SEQUENCE LISTING

<160> NUMBER OF SEQ ID NOS: 86

<210> SEQ ID NO 1
<211> LENGTH: 237
<212> TYPE: PRT
<213> ORGANISM: Artificial Sequence
<220> FEATURE:
<223> OTHER INFORMATION: IF7 heavy chain amino acid sequence

<400> SEQUENCE: 1

Gln Pro Ala Met Ala Glu Val Gln Leu Val Gln Ser Gly Gly Ala Val
1               5                   10                  15

Val Gln Pro Gly Arg Ser Leu Arg Leu Ser Cys Ala Ala Ser Gly Phe
            20                  25                  30

Thr Phe Ser Thr Tyr Gly Met His Trp Val Arg Gln Ala Pro Gly Lys
        35                  40                  45

Gly Leu Glu Trp Val Ala Val Ser Tyr Asp Gly Ser Asn Lys Tyr
    50                  55                  60

Tyr Ala Asp Phe Val Lys Gly Arg Phe Thr Ile Ser Arg Asp Asn Pro
65                  70                  75                  80

Lys Asn Thr Leu Tyr Leu Gln Met Asn Ser Leu Arg Ala Asp Asp Thr
                85                  90                  95

Ala Val Tyr Tyr Cys Ala Arg Arg Gly Gly Leu Asp Ile Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Ala
    210                 215                 220

Ala Ala His His His His His His Gly Pro Gln Ile Arg
225                 230                 235

<210> SEQ ID NO 2
<211> LENGTH: 221
<212> TYPE: PRT
<213> ORGANISM: Artificial Sequence
<220> FEATURE:
<223> OTHER INFORMATION: VH amino acid sequence

<400> SEQUENCE: 2

Glu Val Gln Leu Val Gln Ser Gly Gly Ala Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Ala Val Ser Tyr Asp Gly Ser Asn Lys Tyr Tyr Ala Asp Phe Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Arg Gly Gly Leu Asp Ile Trp Gly Gln Gly Thr Thr Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Ala Ala Ala
    210                 215                 220

<210> SEQ ID NO 3
<211> LENGTH: 5
<212> TYPE: PRT
<213> ORGANISM: Artificial Sequence
<220> FEATURE:
<223> OTHER INFORMATION: VH CDR1 amino acid sequence

<400> SEQUENCE: 3

Thr Tyr Gly Met His
1               5

<210> SEQ ID NO 4
<211> LENGTH: 17
<212> TYPE: PRT
<213> ORGANISM: Artificial Sequence
<220> FEATURE:
<223> OTHER INFORMATION: VH CDR2 amino acid sequence

<400> SEQUENCE: 4

Ala Val Ser Tyr Asp Gly Ser Asn Lys Tyr Tyr Ala Asp Phe Val Lys
1               5                   10                  15

Gly

<210> SEQ ID NO 5
<211> LENGTH: 6
<212> TYPE: PRT
<213> ORGANISM: Artificial Sequence
<220> FEATURE:

<223> OTHER INFORMATION: VH CDR3 amino acid sequence

<400> SEQUENCE: 5

Arg Gly Gly Leu Asp Ile
1               5

<210> SEQ ID NO 6
<211> LENGTH: 108
<212> TYPE: PRT
<213> ORGANISM: Artificial Sequence
<220> FEATURE:
<223> OTHER INFORMATION: light chain VL amino acid sequence of 1F7

<400> SEQUENCE: 6

Leu Thr Gln Pro Pro Ala Ser Gly Thr Pro Gly Gln Arg Val Thr
1               5                   10                  15

Ile Ser Cys Ser Gly Ser Ser Asn Ile Gly Ser Asn Thr Val Asn
                20                  25                  30

Trp Tyr Gln Gln Leu Pro Gly Thr Ala Pro Lys Leu Leu Ile Tyr Gly
                35                  40                  45

Asn Asp Gln Arg Pro Ser Gly Val Pro Asp Arg Phe Ser Ala Ser Lys
    50                  55                  60

Ser Gly Thr Ser Ala Ser Leu Ala Ile Ser Gly Leu Gln Ser Glu Asp
65                  70                  75                  80

Glu Ala His Tyr Tyr Cys Ala Ala Trp Asp Gly Ser Leu Asn Gly Gly
                85                  90                  95

Val Ile Phe Gly Gly Gly Thr Lys Val Thr Leu Gly
                100                 105

<210> SEQ ID NO 7
<211> LENGTH: 109
<212> TYPE: PRT
<213> ORGANISM: Artificial Sequence
<220> FEATURE:
<223> OTHER INFORMATION: light chain VL amino acid sequence of hFab4.1

<400> SEQUENCE: 7

Val Thr Gln Pro Pro Ser Ala Ser Gly Thr Pro Gly Gln Arg Val Thr
1               5                   10                  15

Ile Ser Cys Ser Gly Ser Ser Asn Ile Gly Thr Asn Pro Val Asn
                20                  25                  30

Trp Tyr Gln Gln Leu Pro Gly Thr Ala Pro Lys Leu Leu Ile Tyr Thr
                35                  40                  45

Thr Asp Gln Arg Pro Ser Gly Val Pro Asp Arg Phe Ser Gly Ser Lys
    50                  55                  60

Ser Gly Thr Ser Ala Ser Leu Ala Ile Ser Gly Leu Gln Ser Glu Asp
65                  70                  75                  80

Glu Ala Asp Tyr Tyr Cys Ala Ala Trp Asp Asp Ser Leu Ser Gly Leu
                85                  90                  95

Tyr Val Phe Gly Thr Gly Thr Lys Val Thr Val Leu Gly
                100                 105

<210> SEQ ID NO 8
<211> LENGTH: 109
<212> TYPE: PRT
<213> ORGANISM: Artificial Sequence
<220> FEATURE:
<223> OTHER INFORMATION: light chain VL amino acid sequence of hFab4.2

<400> SEQUENCE: 8

```
Met Thr His Thr Pro Leu Ser Leu Ser Val Thr Gly Gln Pro Ala
1               5                   10                  15

Ser Ile Ser Cys Lys Ser Ser Gln Ser Leu Leu His Ser Asp Gly Lys
            20                  25                  30

Thr Tyr Leu Tyr Trp Tyr Leu Gln Arg Pro Gly Gln Ser Pro Gln Pro
            35                  40                  45

Leu Ile Tyr Glu Val Ser Asn Arg Phe Ser Gly Val Pro Asp Arg Phe
50                  55                  60

Ser Gly Ser Gly Ser Gly Thr Asp Phe Thr Leu Lys Ile Ser Arg Val
65                  70                  75                  80

Glu Ala Glu Asp Val Gly Val Tyr Tyr Cys Met Gln Ser Leu Gln Leu
                85                  90                  95

Trp Thr Phe Gly Gln Gly Thr Lys Val Glu Ile Lys Arg
            100                 105
```

<210> SEQ ID NO 9
<211> LENGTH: 110
<212> TYPE: PRT
<213> ORGANISM: Artificial Sequence
<220> FEATURE:
<223> OTHER INFORMATION: light chain VL amino acid sequence of hFab4.3

<400> SEQUENCE: 9

```
Met Thr Gln Ser Pro Leu Ser Leu Pro Val Thr Leu Gly Gln Pro Ala
1               5                   10                  15

Ser Ile Ser Cys Arg Ser Ser Gln Ser Leu Ile His Ser Asp Gly Asn
            20                  25                  30

Thr Tyr Leu Asp Trp Phe Gln Gln Arg Pro Gly Gln Ser Pro Arg Arg
            35                  40                  45

Leu Ile Tyr Lys Val Ser Asn Arg Asp Ser Gly Val Pro Asp Arg Phe
50                  55                  60

Ser Gly Ser Gly Ser Gly Thr Asp Phe Thr Leu Arg Ile Ser Arg Val
65                  70                  75                  80

Glu Ala Glu Asp Ile Gly Val Tyr Tyr Cys Met Gln Ala Thr His Trp
                85                  90                  95

Pro Arg Thr Phe Gly Gln Gly Thr Lys Val Glu Ile Lys Arg
            100                 105                 110
```

<210> SEQ ID NO 10
<211> LENGTH: 110
<212> TYPE: PRT
<213> ORGANISM: Artificial Sequence
<220> FEATURE:
<223> OTHER INFORMATION: light chain VL amino acid sequence of hFab4.4

<400> SEQUENCE: 10

```
Met Thr Gln Ser Pro Leu Ser Leu Pro Val Thr Leu Gly Gln Pro Ala
1               5                   10                  15

Ser Ile Ser Cys Arg Ser Ser Gln Ser Leu Val Asp Ser Ala Gly Asn
            20                  25                  30

Thr Phe Leu His Trp Phe His Gln Arg Pro Gly Gln Ser Pro Arg Arg
            35                  40                  45

Leu Ile Tyr Lys Val Ser Asn Arg Asp Ser Gly Val Pro Asp Arg Phe
50                  55                  60

Ser Gly Ser Gly Ser Gly Thr Asp Phe Thr Leu Lys Ile Ser Arg Val
65                  70                  75                  80

Glu Ala Glu Asp Val Gly Val Tyr Tyr Cys Met Gln Gly Thr His Trp
                85                  90                  95
```

```
Pro Arg Thr Phe Gly Gln Gly Thr Lys Val Glu Ile Lys Arg
            100                 105                 110

<210> SEQ ID NO 11
<211> LENGTH: 110
<212> TYPE: PRT
<213> ORGANISM: Artificial Sequence
<220> FEATURE:
<223> OTHER INFORMATION: light chain VL amino acid sequence of hFab4.5

<400> SEQUENCE: 11

Leu Thr Gln Ser Pro Leu Ser Leu Pro Val Thr Leu Gly Gln Pro Ala
1               5                   10                  15

Ser Ile Ser Cys Lys Ser Ser Gln Ser Leu Val Asp Ser Asp Gly Asn
            20                  25                  30

Thr Tyr Leu Asn Trp Phe Gln Gln Arg Pro Gly Gln Ser Pro Arg Arg
        35                  40                  45

Leu Ile Tyr Lys Val Ser Asn Arg Asp Ser Gly Val Pro Asp Arg Phe
    50                  55                  60

Ser Gly Ser Gly Ser Gly Thr Asp Phe Thr Leu Lys Ile Ser Arg Val
65                  70                  75                  80

Glu Ala Glu Asp Val Gly Val Tyr Tyr Cys Met Gln Gly Thr His Trp
                85                  90                  95

Pro Arg Thr Phe Gly Gln Gly Thr Lys Val Glu Ile Lys Arg
            100                 105                 110

<210> SEQ ID NO 12
<211> LENGTH: 110
<212> TYPE: PRT
<213> ORGANISM: Artificial Sequence
<220> FEATURE:
<223> OTHER INFORMATION: light chain VL amino acid sequence of hFab4.7

<400> SEQUENCE: 12

Met Thr Gln Ser Pro Leu Ser Leu Pro Val Thr Leu Gly Gln Pro Ala
1               5                   10                  15

Ser Ile Ser Cys Arg Ser Ser Gln Ser Leu Val His Ser Asp Gly Asn
            20                  25                  30

Met Tyr Leu Asn Trp Phe Gln Gln Arg Pro Gly Gln Ser Pro Arg Arg
        35                  40                  45

Leu Ile Tyr Lys Val Ser Asn Arg Asp Ser Gly Val Pro Asp Arg Phe
    50                  55                  60

Ser Gly Ser Gly Ser Gly Thr Asp Phe Thr Leu Lys Ile Ser Arg Val
65                  70                  75                  80

Glu Ala Glu Asp Val Gly Val Tyr Tyr Cys Met Gln Ala Thr Gln Pro
                85                  90                  95

Thr Trp Thr Phe Gly Gln Gly Thr Lys Leu Glu Ile Lys Arg
            100                 105                 110

<210> SEQ ID NO 13
<211> LENGTH: 105
<212> TYPE: PRT
<213> ORGANISM: Artificial Sequence
<220> FEATURE:
<223> OTHER INFORMATION: light chain VL amino acid sequence of hFab4.8

<400> SEQUENCE: 13

Met Thr Gln Ser Pro Ser Ser Leu Ser Ala Ser Val Gly Asp Arg Val
1               5                   10                  15
```

```
Thr Ile Thr Cys Gln Ala Ser Gln Asp Ile Ser Asn Tyr Leu Asn Trp
             20                  25                  30

Tyr Gln Gln Lys Pro Gly Lys Ala Pro Lys Leu Leu Ile Tyr Asp Ala
         35                  40                  45

Ser Asn Leu Glu Thr Gly Val Pro Ser Arg Phe Ser Gly Ser Gly Ser
 50                  55                  60

Gly Thr Asp Phe Thr Phe Thr Ile Ser Ser Leu Gln Pro Asp Asp Phe
 65                  70                  75                  80

Ala Thr Tyr Tyr Cys Gln Gln Thr Tyr Ser Trp Pro Arg Thr Phe Gly
                 85                  90                  95

Gln Gly Thr Lys Leu Glu Ile Lys Arg
             100                 105
```

<210> SEQ ID NO 14
<211> LENGTH: 105
<212> TYPE: PRT
<213> ORGANISM: Artificial Sequence
<220> FEATURE:
<223> OTHER INFORMATION: light chain VL amino acid sequence of hFab4.9

<400> SEQUENCE: 14

```
Met Thr Gln Ser Pro Ser Ser Leu Ser Ala Ser Val Gly His Pro Val
 1                   5                  10                  15

Thr Ile Thr Cys Arg Ala Ser Gln Ser Leu Ile Ser Tyr Leu Asn Trp
             20                  25                  30

Tyr His Gln Lys Pro Gly Lys Ala Pro Lys Leu Leu Ile Tyr Ala Ala
         35                  40                  45

Ser Ile Leu Gln Ser Gly Val Pro Ser Arg Phe Ser Gly Ser Gly Ser
 50                  55                  60

Gly Thr Asp Phe Thr Leu Thr Ile Ser Ser Leu Gln Pro Glu Asn Phe
 65                  70                  75                  80

Ala Ser Tyr Tyr Cys Gln His Thr Asp Ser Phe Pro Arg Thr Phe Gly
                 85                  90                  95

His Gly Thr Lys Val Glu Ile Lys Arg
             100                 105
```

<210> SEQ ID NO 15
<211> LENGTH: 108
<212> TYPE: PRT
<213> ORGANISM: Artificial Sequence
<220> FEATURE:
<223> OTHER INFORMATION: light chain VL amino acid sequence of hFab4.10

<400> SEQUENCE: 15

```
Leu Thr Gln Pro Pro Ser Ala Ser Gly Thr Pro Gly Gln Gly Val Thr
 1                   5                  10                  15

Ile Ser Cys Arg Gly Ser Thr Ser Asn Ile Gly Asn Asn Val Val Asn
             20                  25                  30

Trp Tyr Gln His Val Pro Gly Ser Ala Pro Lys Leu Leu Ile Trp Ser
         35                  40                  45

Asn Ile Gln Arg Pro Ser Gly Ile Pro Asp Arg Phe Ser Gly Ser Lys
 50                  55                  60

Ser Gly Thr Ser Ala Ser Leu Ala Ile Ser Gly Leu Gln Ser Glu Asp
 65                  70                  75                  80

Glu Ala Val Tyr Tyr Cys Ala Val Trp Asp Asp Gly Leu Ala Gly Trp
                 85                  90                  95

Val Phe Gly Gly Gly Thr Thr Val Thr Val Leu Ser
             100                 105
```

```
<210> SEQ ID NO 16
<211> LENGTH: 105
<212> TYPE: PRT
<213> ORGANISM: Artificial Sequence
<220> FEATURE:
<223> OTHER INFORMATION: light chain VL amino acid sequence of hFab4.12

<400> SEQUENCE: 16

Met Thr Gln Ala Pro Val Val Ser Val Ala Leu Glu Gln Thr Val Arg
1               5                   10                  15

Ile Thr Cys Gln Gly Asp Ser Leu Ala Ile Tyr Tyr Asp Phe Trp Tyr
            20                  25                  30

Gln His Lys Pro Gly Gln Ala Pro Val Leu Val Ile Tyr Gly Lys Asn
        35                  40                  45

Asn Arg Pro Ser Gly Ile Pro His Arg Phe Ser Gly Ser Ser Ser Asn
    50                  55                  60

Thr Asp Ser Leu Thr Ile Thr Gly Ala Gln Ala Glu Asp Glu Ala Asp
65                  70                  75                  80

Tyr Tyr Cys Asn Ser Arg Asp Ser Ser Gly Asn His Trp Val Phe Gly
                85                  90                  95

Gly Gly Thr Asn Leu Thr Val Leu Gly
            100                 105

<210> SEQ ID NO 17
<211> LENGTH: 110
<212> TYPE: PRT
<213> ORGANISM: Artificial Sequence
<220> FEATURE:
<223> OTHER INFORMATION: light chain VL amino acid sequence of hFab4.18

<400> SEQUENCE: 17

Leu Thr Gln Ser Pro Leu Ser Leu Pro Val Thr Leu Gly Gln Pro Ala
1               5                   10                  15

Ser Ile Ser Cys Lys Ser Asn Gln Ser Leu Val His Ser Asp Gly Asn
            20                  25                  30

Thr Tyr Leu Asn Trp Phe Gln Gln Arg Pro Gly Gln Ser Pro Arg Arg
        35                  40                  45

Leu Ile Tyr Lys Val Ser Asn Arg Asp Ser Gly Val Pro Asp Arg Phe
    50                  55                  60

Ser Gly Ser Gly Ser Gly Thr Asp Phe Thr Leu Lys Ile Asn Arg Val
65                  70                  75                  80

Glu Ala Glu Asp Val Gly Val Tyr Tyr Cys Met Gln Gly Thr Gln Trp
                85                  90                  95

Pro Arg Thr Phe Gly Gln Gly Thr Lys Leu Asp Ile Lys Arg
            100                 105                 110

<210> SEQ ID NO 18
<211> LENGTH: 13
<212> TYPE: PRT
<213> ORGANISM: Artificial Sequence
<220> FEATURE:
<223> OTHER INFORMATION: light chain VL CDR1 amino acid consensus
      sequence of 1F7, hFab4.1, hFab4.12 and hFab4.10
<220> FEATURE:
<221> NAME/KEY: MISC_FEATURE
<222> LOCATION: (1)..(1)
<223> OTHER INFORMATION: Q or S or R
<220> FEATURE:
<221> NAME/KEY: MISC_FEATURE
<222> LOCATION: (3)..(3)
<223> OTHER INFORMATION: D or S
```

```
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (5)..(5)
<223> OTHER INFORMATION: S or L
<220> FEATURE:
<221> NAME/KEY: MISC_FEATURE
<222> LOCATION: (6)..(6)
<223> OTHER INFORMATION: A or N
<220> FEATURE:
<221> NAME/KEY: MISC_FEATURE
<222> LOCATION: (8)..(8)
<223> OTHER INFORMATION: G or absent
<220> FEATURE:
<221> NAME/KEY: MISC_FEATURE
<222> LOCATION: (9)..(9)
<223> OTHER INFORMATION: T or N or S or absent
<220> FEATURE:
<221> NAME/KEY: MISC_FEATURE
<222> LOCATION: (10)..(10)
<223> OTHER INFORMATION: N or Y
<220> FEATURE:
<221> NAME/KEY: MISC_FEATURE
<222> LOCATION: (11)..(11)
<223> OTHER INFORMATION: V or P or T or Y
<220> FEATURE:
<221> NAME/KEY: MISC_FEATURE
<222> LOCATION: (12)..(12)
<223> OTHER INFORMATION: V or D
<220> FEATURE:
<221> NAME/KEY: MISC_FEATURE
<222> LOCATION: (13)..(13)
<223> OTHER INFORMATION: N or F

<400> SEQUENCE: 18

Xaa Gly Xaa Xaa Xaa Xaa Ile Xaa Xaa Xaa Xaa Xaa Xaa
1               5                   10

<210> SEQ ID NO 19
<211> LENGTH: 16
<212> TYPE: PRT
<213> ORGANISM: Artificial Sequence
<220> FEATURE:
<223> OTHER INFORMATION: light chain VL CDR1 amino acid consensus
      sequence of hFab4.2; hFab4.3; hFab4.4; hFab4.5; hFab4.7 and
      hFab4.18
<220> FEATURE:
<221> NAME/KEY: MISC_FEATURE
<222> LOCATION: (1)..(1)
<223> OTHER INFORMATION: K or R
<220> FEATURE:
<221> NAME/KEY: MISC_FEATURE
<222> LOCATION: (3)..(3)
<223> OTHER INFORMATION: S or N
<220> FEATURE:
<221> NAME/KEY: MISC_FEATURE
<222> LOCATION: (7)..(7)
<223> OTHER INFORMATION: V or I or L
<220> FEATURE:
<221> NAME/KEY: MISC_FEATURE
<222> LOCATION: (8)..(8)
<223> OTHER INFORMATION: H or D
<220> FEATURE:
<221> NAME/KEY: MISC_FEATURE
<222> LOCATION: (10)..(10)
<223> OTHER INFORMATION: D or A
<220> FEATURE:
<221> NAME/KEY: MISC_FEATURE
<222> LOCATION: (12)..(12)
<223> OTHER INFORMATION: N or K
<220> FEATURE:
<221> NAME/KEY: MISC_FEATURE
<222> LOCATION: (13)..(13)
<223> OTHER INFORMATION: T or M
```

<220> FEATURE:
<221> NAME/KEY: MISC_FEATURE
<222> LOCATION: (14)..(14)
<223> OTHER INFORMATION: Y or F
<220> FEATURE:
<221> NAME/KEY: MISC_FEATURE
<222> LOCATION: (16)..(16)
<223> OTHER INFORMATION: Y or N or D or H

<400> SEQUENCE: 19

Xaa Ser Xaa Gln Ser Leu Xaa Xaa Ser Xaa Gly Xaa Xaa Xaa Leu Xaa
1               5                   10                  15

<210> SEQ ID NO 20
<211> LENGTH: 11
<212> TYPE: PRT
<213> ORGANISM: Artificial Sequence
<220> FEATURE:
<223> OTHER INFORMATION: light chain VL CDR1 amino acid consensus
      sequence of hFab4.8 and hFab4.9
<220> FEATURE:
<221> NAME/KEY: MISC_FEATURE
<222> LOCATION: (1)..(1)
<223> OTHER INFORMATION: Q or R
<220> FEATURE:
<221> NAME/KEY: MISC_FEATURE
<222> LOCATION: (5)..(5)
<223> OTHER INFORMATION: D or S
<220> FEATURE:
<221> NAME/KEY: MISC_FEATURE
<222> LOCATION: (6)..(6)
<223> OTHER INFORMATION: I or L
<220> FEATURE:
<221> NAME/KEY: MISC_FEATURE
<222> LOCATION: (7)..(7)
<223> OTHER INFORMATION: S or I
<220> FEATURE:
<221> NAME/KEY: MISC_FEATURE
<222> LOCATION: (8)..(8)
<223> OTHER INFORMATION: N or S

<400> SEQUENCE: 20

Xaa Ala Ser Gln Xaa Xaa Xaa Xaa Tyr Leu Asn
1               5                   10

<210> SEQ ID NO 21
<211> LENGTH: 6
<212> TYPE: PRT
<213> ORGANISM: Artificial Sequence
<220> FEATURE:
<223> OTHER INFORMATION: light chain VL CDR2 amino acid consensus
      sequence of 1F7, hFab4.1, hFab4.12 and hFab4.10
<220> FEATURE:
<221> NAME/KEY: MISC_FEATURE
<222> LOCATION: (1)..(1)
<223> OTHER INFORMATION: G or T or S
<220> FEATURE:
<221> NAME/KEY: MISC_FEATURE
<222> LOCATION: (2)..(2)
<223> OTHER INFORMATION: K or T or N
<220> FEATURE:
<221> NAME/KEY: MISC_FEATURE
<222> LOCATION: (3)..(3)
<223> OTHER INFORMATION: N or D or I
<220> FEATURE:
<221> NAME/KEY: MISC_FEATURE
<222> LOCATION: (4)..(4)
<223> OTHER INFORMATION: N or Q

<400> SEQUENCE: 21

Xaa Xaa Xaa Xaa Arg Pro
1               5

```
<210> SEQ ID NO 22
<211> LENGTH: 6
<212> TYPE: PRT
<213> ORGANISM: Artificial Sequence
<220> FEATURE:
<223> OTHER INFORMATION: light chain VL CDR2 amino acid consensus
      sequence of hFab4.2; hFab4.3; hFab4.4; hFab4.5; hFab4.7 and
      hFab4.18
<220> FEATURE:
<221> NAME/KEY: MISC_FEATURE
<222> LOCATION: (1)..(1)
<223> OTHER INFORMATION: E or K
<220> FEATURE:
<221> NAME/KEY: MISC_FEATURE
<222> LOCATION: (6)..(6)
<223> OTHER INFORMATION: D or F

<400> SEQUENCE: 22

Xaa Val Ser Asn Arg Xaa
1               5

<210> SEQ ID NO 23
<211> LENGTH: 6
<212> TYPE: PRT
<213> ORGANISM: Artificial Sequence
<220> FEATURE:
<223> OTHER INFORMATION: light chain VL CDR2 amino acid consensus
      sequence of hFab4.8 and hFab4.9
<220> FEATURE:
<221> NAME/KEY: MISC_FEATURE
<222> LOCATION: (1)..(1)
<223> OTHER INFORMATION: D or A
<220> FEATURE:
<221> NAME/KEY: MISC_FEATURE
<222> LOCATION: (4)..(4)
<223> OTHER INFORMATION: N or I
<220> FEATURE:
<221> NAME/KEY: MISC_FEATURE
<222> LOCATION: (6)..(6)
<223> OTHER INFORMATION: E or Q

<400> SEQUENCE: 23

Xaa Ala Ser Xaa Leu Xaa
1               5

<210> SEQ ID NO 24
<211> LENGTH: 12
<212> TYPE: PRT
<213> ORGANISM: Artificial Sequence
<220> FEATURE:
<223> OTHER INFORMATION: light chain VL CDR3 amino acid consensus
      sequence of 1F7, hFab4.1, hFab4.12 and hFab4.10
<220> FEATURE:
<221> NAME/KEY: MISC_FEATURE
<222> LOCATION: (1)..(1)
<223> OTHER INFORMATION: N or A
<220> FEATURE:
<221> NAME/KEY: MISC_FEATURE
<222> LOCATION: (2)..(2)
<223> OTHER INFORMATION: S or A or V
<220> FEATURE:
<221> NAME/KEY: MISC_FEATURE
<222> LOCATION: (3)..(3)
<223> OTHER INFORMATION: R or W
<220> FEATURE:
<221> NAME/KEY: MISC_FEATURE
<222> LOCATION: (5)..(5)
<223> OTHER INFORMATION: S or D or G
<220> FEATURE:
<221> NAME/KEY: MISC_FEATURE
<222> LOCATION: (6)..(6)
<223> OTHER INFORMATION: S or G
<220> FEATURE:
<221> NAME/KEY: MISC_FEATURE
<222> LOCATION: (7)..(7)
```

```
<223> OTHER INFORMATION: L or absent
<220> FEATURE:
<221> NAME/KEY: MISC_FEATURE
<222> LOCATION: (8)..(8)
<223> OTHER INFORMATION: G or S or A or N
<220> FEATURE:
<221> NAME/KEY: MISC_FEATURE
<222> LOCATION: (9)..(9)
<223> OTHER INFORMATION: N or G
<220> FEATURE:
<221> NAME/KEY: MISC_FEATURE
<222> LOCATION: (10)..(10)
<223> OTHER INFORMATION: H or L or G or absent
<220> FEATURE:
<221> NAME/KEY: MISC_FEATURE
<222> LOCATION: (11)..(11)
<223> OTHER INFORMATION: W or Y or V
<220> FEATURE:
<221> NAME/KEY: MISC_FEATURE
<222> LOCATION: (12)..(12)
<223> OTHER INFORMATION: V or I

<400> SEQUENCE: 24

Xaa Xaa Xaa Asp Xaa Xaa Xaa Xaa Xaa Xaa Xaa Xaa
1               5                   10

<210> SEQ ID NO 25
<211> LENGTH: 9
<212> TYPE: PRT
<213> ORGANISM: Artificial Sequence
<220> FEATURE:
<223> OTHER INFORMATION: light chain VL CDR3 amino acid consensus
      sequence of hFab4.2; hFab4.3; hFab4.4; hFab4.5; hFab4.7 and
      hFab4.18
<220> FEATURE:
<221> NAME/KEY: MISC_FEATURE
<222> LOCATION: (3)..(3)
<223> OTHER INFORMATION: S or A or G
<220> FEATURE:
<221> NAME/KEY: MISC_FEATURE
<222> LOCATION: (4)..(4)
<223> OTHER INFORMATION: L or T
<220> FEATURE:
<221> NAME/KEY: MISC_FEATURE
<222> LOCATION: (5)..(5)
<223> OTHER INFORMATION: Q or H
<220> FEATURE:
<221> NAME/KEY: MISC_FEATURE
<222> LOCATION: (6)..(6)
<223> OTHER INFORMATION: W or P or absent
<220> FEATURE:
<221> NAME/KEY: MISC_FEATURE
<222> LOCATION: (7)..(7)
<223> OTHER INFORMATION: L or T or P
<220> FEATURE:
<221> NAME/KEY: MISC_FEATURE
<222> LOCATION: (8)..(8)
<223> OTHER INFORMATION: W or R

<400> SEQUENCE: 25

Met Gln Xaa Xaa Xaa Xaa Xaa Xaa Thr
1               5

<210> SEQ ID NO 26
<211> LENGTH: 9
<212> TYPE: PRT
<213> ORGANISM: Artificial Sequence
<220> FEATURE:
<223> OTHER INFORMATION: light chain VL CDR3 amino acid consensus
      sequence of hFab4.8 and hFab4.9
<220> FEATURE:
<221> NAME/KEY: MISC_FEATURE
<222> LOCATION: (2)..(2)
<223> OTHER INFORMATION: Q or H
<220> FEATURE:
```

```
<221> NAME/KEY: MISC_FEATURE
<222> LOCATION: (4)..(4)
<223> OTHER INFORMATION: Y or D
<220> FEATURE:
<221> NAME/KEY: MISC_FEATURE
<222> LOCATION: (6)..(6)
<223> OTHER INFORMATION: W or F

<400> SEQUENCE: 26

Gln Xaa Thr Xaa Ser Xaa Pro Arg Thr
1               5

<210> SEQ ID NO 27
<211> LENGTH: 109
<212> TYPE: PRT
<213> ORGANISM: Artificial Sequence
<220> FEATURE:
<223> OTHER INFORMATION: light chain VL amino acid consensus sequence of
      1F7, hFab4.1, hFab4.12 and hFab4.10
<220> FEATURE:
<221> NAME/KEY: MISC_FEATURE
<222> LOCATION: (1)..(1)
<223> OTHER INFORMATION: M or V or L
<220> FEATURE:
<221> NAME/KEY: MISC_FEATURE
<222> LOCATION: (4)..(4)
<223> OTHER INFORMATION: A or P
<220> FEATURE:
<221> NAME/KEY: MISC_FEATURE
<222> LOCATION: (6)..(6)
<223> OTHER INFORMATION: V or S or P
<220> FEATURE:
<221> NAME/KEY: MISC_FEATURE
<222> LOCATION: (7)..(7)
<223> OTHER INFORMATION: V or A
<220> FEATURE:
<221> NAME/KEY: MISC_FEATURE
<222> LOCATION: (9)..(9)
<223> OTHER INFORMATION: V or G
<220> FEATURE:
<221> NAME/KEY: MISC_FEATURE
<222> LOCATION: (10)..(10)
<223> OTHER INFORMATION: A or T
<220> FEATURE:
<221> NAME/KEY: MISC_FEATURE
<222> LOCATION: (11)..(11)
<223> OTHER INFORMATION: L or P
<220> FEATURE:
<221> NAME/KEY: MISC_FEATURE
<222> LOCATION: (12)..(12)
<223> OTHER INFORMATION: E or G
<220> FEATURE:
<221> NAME/KEY: MISC_FEATURE
<222> LOCATION: (14)..(14)
<223> OTHER INFORMATION: T or R or G
<220> FEATURE:
<221> NAME/KEY: MISC_FEATURE
<222> LOCATION: (16)..(16)
<223> OTHER INFORMATION: R or T
<220> FEATURE:
<221> NAME/KEY: MISC_FEATURE
<222> LOCATION: (18)..(18)
<223> OTHER INFORMATION: S or T
<220> FEATURE:
<221> NAME/KEY: MISC_FEATURE
<222> LOCATION: (20)..(20)
<223> OTHER INFORMATION: R or S or Q
<220> FEATURE:
<221> NAME/KEY: MISC_FEATURE
<222> LOCATION: (22)..(22)
<223> OTHER INFORMATION: D or S
<220> FEATURE:
<221> NAME/KEY: MISC_FEATURE
<222> LOCATION: (23)..(23)
<223> OTHER INFORMATION: S or T
<220> FEATURE:
<221> NAME/KEY: MISC_FEATURE
```

```
<222> LOCATION: (24)..(24)
<223> OTHER INFORMATION: L or S
<220> FEATURE:
<221> NAME/KEY: MISC_FEATURE
<222> LOCATION: (25)..(25)
<223> OTHER INFORMATION: A or N
<220> FEATURE:
<221> NAME/KEY: MISC_FEATURE
<222> LOCATION: (27)..(27)
<223> OTHER INFORMATION: G or absent
<220> FEATURE:
<221> NAME/KEY: MISC_FEATURE
<222> LOCATION: (28)..(28)
<223> OTHER INFORMATION: N or S or T or absent
<220> FEATURE:
<221> NAME/KEY: MISC_FEATURE
<222> LOCATION: (29)..(29)
<223> OTHER INFORMATION: N or Y
<220> FEATURE:
<221> NAME/KEY: MISC_FEATURE
<222> LOCATION: (30)..(30)
<223> OTHER INFORMATION: Y or P or T or V
<220> FEATURE:
<221> NAME/KEY: MISC_FEATURE
<222> LOCATION: (31)..(31)
<223> OTHER INFORMATION: D or V
<220> FEATURE:
<221> NAME/KEY: MISC_FEATURE
<222> LOCATION: (32)..(32)
<223> OTHER INFORMATION: F or N
<220> FEATURE:
<221> NAME/KEY: MISC_FEATURE
<222> LOCATION: (36)..(36)
<223> OTHER INFORMATION: H or Q
<220> FEATURE:
<221> NAME/KEY: MISC_FEATURE
<222> LOCATION: (37)..(37)
<223> OTHER INFORMATION: K or L or V
<220> FEATURE:
<221> NAME/KEY: MISC_FEATURE
<222> LOCATION: (40)..(40)
<223> OTHER INFORMATION: Q or T or S
<220> FEATURE:
<221> NAME/KEY: MISC_FEATURE
<222> LOCATION: (43)..(43)
<223> OTHER INFORMATION: K or V
<220> FEATURE:
<221> NAME/KEY: MISC_FEATURE
<222> LOCATION: (45)..(45)
<223> OTHER INFORMATION: L or V
<220> FEATURE:
<221> NAME/KEY: MISC_FEATURE
<222> LOCATION: (47)..(47)
<223> OTHER INFORMATION: Y or W
<220> FEATURE:
<221> NAME/KEY: MISC_FEATURE
<222> LOCATION: (48)..(48)
<223> OTHER INFORMATION: G or T or S
<220> FEATURE:
<221> NAME/KEY: MISC_FEATURE
<222> LOCATION: (49)..(49)
<223> OTHER INFORMATION: K or T or N
<220> FEATURE:
<221> NAME/KEY: MISC_FEATURE
<222> LOCATION: (50)..(50)
<223> OTHER INFORMATION: N or D or I
<220> FEATURE:
<221> NAME/KEY: MISC_FEATURE
<222> LOCATION: (51)..(51)
<223> OTHER INFORMATION: N or Q
<220> FEATURE:
<221> NAME/KEY: MISC_FEATURE
<222> LOCATION: (56)..(56)
<223> OTHER INFORMATION: I or V
<220> FEATURE:
<221> NAME/KEY: MISC_FEATURE
<222> LOCATION: (58)..(58)
<223> OTHER INFORMATION: H or D
<220> FEATURE:
```

```
<221> NAME/KEY: MISC_FEATURE
<222> LOCATION: (62)..(62)
<223> OTHER INFORMATION: G or A
<220> FEATURE:
<221> NAME/KEY: MISC_FEATURE
<222> LOCATION: (64)..(64)
<223> OTHER INFORMATION: S or K
<220> FEATURE:
<221> NAME/KEY: MISC_FEATURE
<222> LOCATION: (66)..(66)
<223> OTHER INFORMATION: N or G
<220> FEATURE:
<221> NAME/KEY: MISC_FEATURE
<222> LOCATION: (68)..(68)
<223> OTHER INFORMATION: S or absent
<220> FEATURE:
<221> NAME/KEY: MISC_FEATURE
<222> LOCATION: (69)..(69)
<223> OTHER INFORMATION: D or A
<220> FEATURE:
<221> NAME/KEY: MISC_FEATURE
<222> LOCATION: (72)..(72)
<223> OTHER INFORMATION: A or T
<220> FEATURE:
<221> NAME/KEY: MISC_FEATURE
<222> LOCATION: (74)..(74)
<223> OTHER INFORMATION: T or S
<220> FEATURE:
<221> NAME/KEY: MISC_FEATURE
<222> LOCATION: (76)..(76)
<223> OTHER INFORMATION: A or L
<220> FEATURE:
<221> NAME/KEY: MISC_FEATURE
<222> LOCATION: (78)..(78)
<223> OTHER INFORMATION: A or S
<220> FEATURE:
<221> NAME/KEY: MISC_FEATURE
<222> LOCATION: (83)..(83)
<223> OTHER INFORMATION: D or H or V
<220> FEATURE:
<221> NAME/KEY: MISC_FEATURE
<222> LOCATION: (87)..(87)
<223> OTHER INFORMATION: N or A
<220> FEATURE:
<221> NAME/KEY: MISC_FEATURE
<222> LOCATION: (88)..(88)
<223> OTHER INFORMATION: S or A or V
<220> FEATURE:
<221> NAME/KEY: MISC_FEATURE
<222> LOCATION: (89)..(89)
<223> OTHER INFORMATION: R or W
<220> FEATURE:
<221> NAME/KEY: MISC_FEATURE
<222> LOCATION: (91)..(91)
<223> OTHER INFORMATION: S or D or G
<220> FEATURE:
<221> NAME/KEY: MISC_FEATURE
<222> LOCATION: (92)..(92)
<223> OTHER INFORMATION: S or G
<220> FEATURE:
<221> NAME/KEY: MISC_FEATURE
<222> LOCATION: (93)..(93)
<223> OTHER INFORMATION: L or absent
<220> FEATURE:
<221> NAME/KEY: MISC_FEATURE
<222> LOCATION: (94)..(94)
<223> OTHER INFORMATION: G or S or A or N
<220> FEATURE:
<221> NAME/KEY: MISC_FEATURE
<222> LOCATION: (95)..(95)
<223> OTHER INFORMATION: N or G
<220> FEATURE:
<221> NAME/KEY: MISC_FEATURE
<222> LOCATION: (96)..(96)
<223> OTHER INFORMATION: G or H or L or absent
<220> FEATURE:
<221> NAME/KEY: MISC_FEATURE
<222> LOCATION: (97)..(97)
<223> OTHER INFORMATION: V or W or Y
```

<220> FEATURE:
<221> NAME/KEY: MISC_FEATURE
<222> LOCATION: (98)..(98)
<223> OTHER INFORMATION: V or I
<220> FEATURE:
<221> NAME/KEY: MISC_FEATURE
<222> LOCATION: (101)..(101)
<223> OTHER INFORMATION: G or T
<220> FEATURE:
<221> NAME/KEY: MISC_FEATURE
<222> LOCATION: (104)..(104)
<223> OTHER INFORMATION: N or K or T
<220> FEATURE:
<221> NAME/KEY: MISC_FEATURE
<222> LOCATION: (105)..(105)
<223> OTHER INFORMATION: L or V
<220> FEATURE:
<221> NAME/KEY: MISC_FEATURE
<222> LOCATION: (109)..(109)
<223> OTHER INFORMATION: G or S

<400> SEQUENCE: 27

Xaa Thr Gln Xaa Pro Xaa Xaa Ser Xaa Xaa Xaa Gln Xaa Val Xaa
 1               5                  10                  15

Ile Xaa Cys Xaa Gly Xaa Xaa Xaa Ile Xaa Xaa Xaa Xaa Xaa
             20                  25                  30

Trp Tyr Gln Xaa Xaa Pro Gly Xaa Ala Pro Xaa Leu Xaa Ile Xaa Xaa
                 35                  40                  45

Xaa Xaa Xaa Arg Pro Ser Gly Xaa Pro Xaa Arg Phe Ser Xaa Ser Xaa
         50                  55                  60

Ser Xaa Thr Xaa Xaa Ser Leu Xaa Ile Xaa Gly Xaa Gln Xaa Glu Asp
 65                  70                  75                  80

Glu Ala Xaa Tyr Tyr Cys Xaa Xaa Asp Xaa Xaa Xaa Xaa Xaa
                 85                  90                  95

Xaa Xaa Phe Gly Xaa Gly Thr Xaa Xaa Thr Val Leu Xaa
             100                 105

<210> SEQ ID NO 28
<211> LENGTH: 110
<212> TYPE: PRT
<213> ORGANISM: Artificial Sequence
<220> FEATURE:
<223> OTHER INFORMATION: light chain VL amino acid consensus sequence of
      hFab4.2; hFab4.3; hFab4.4; hFab4.5; hFab4.7 and hFab4.18
<220> FEATURE:
<221> NAME/KEY: MISC_FEATURE
<222> LOCATION: (1)..(1)
<223> OTHER INFORMATION: M or L
<220> FEATURE:
<221> NAME/KEY: MISC_FEATURE
<222> LOCATION: (3)..(3)
<223> OTHER INFORMATION: H or Q
<220> FEATURE:
<221> NAME/KEY: MISC_FEATURE
<222> LOCATION: (4)..(4)
<223> OTHER INFORMATION: T or S
<220> FEATURE:
<221> NAME/KEY: MISC_FEATURE
<222> LOCATION: (9)..(9)
<223> OTHER INFORMATION: S or P
<220> FEATURE:
<221> NAME/KEY: MISC_FEATURE
<222> LOCATION: (12)..(12)
<223> OTHER INFORMATION: L or P
<220> FEATURE:
<221> NAME/KEY: MISC_FEATURE
<222> LOCATION: (21)..(21)
<223> OTHER INFORMATION: K or R
<220> FEATURE:
<221> NAME/KEY: MISC_FEATURE
<222> LOCATION: (23)..(23)

```
<223> OTHER INFORMATION: S or N
<220> FEATURE:
<221> NAME/KEY: MISC_FEATURE
<222> LOCATION: (27)..(27)
<223> OTHER INFORMATION: V or I or L
<220> FEATURE:
<221> NAME/KEY: MISC_FEATURE
<222> LOCATION: (28)..(28)
<223> OTHER INFORMATION: D or H
<220> FEATURE:
<221> NAME/KEY: MISC_FEATURE
<222> LOCATION: (30)..(30)
<223> OTHER INFORMATION: D or A
<220> FEATURE:
<221> NAME/KEY: MISC_FEATURE
<222> LOCATION: (32)..(32)
<223> OTHER INFORMATION: N or K
<220> FEATURE:
<221> NAME/KEY: MISC_FEATURE
<222> LOCATION: (33)..(33)
<223> OTHER INFORMATION: T or M
<220> FEATURE:
<221> NAME/KEY: MISC_FEATURE
<222> LOCATION: (34)..(34)
<223> OTHER INFORMATION: Y or F
<220> FEATURE:
<221> NAME/KEY: MISC_FEATURE
<222> LOCATION: (36)..(36)
<223> OTHER INFORMATION: N or H or D or Y
<220> FEATURE:
<221> NAME/KEY: MISC_FEATURE
<222> LOCATION: (38)..(38)
<223> OTHER INFORMATION: F or Y
<220> FEATURE:
<221> NAME/KEY: MISC_FEATURE
<222> LOCATION: (39)..(39)
<223> OTHER INFORMATION: Q or H or L
<220> FEATURE:
<221> NAME/KEY: MISC_FEATURE
<222> LOCATION: (47)..(47)
<223> OTHER INFORMATION: R or Q
<220> FEATURE:
<221> NAME/KEY: MISC_FEATURE
<222> LOCATION: (48)..(48)
<223> OTHER INFORMATION: R or P
<220> FEATURE:
<221> NAME/KEY: MISC_FEATURE
<222> LOCATION: (52)..(52)
<223> OTHER INFORMATION: K or E
<220> FEATURE:
<221> NAME/KEY: MISC_FEATURE
<222> LOCATION: (57)..(57)
<223> OTHER INFORMATION: D or F
<220> FEATURE:
<221> NAME/KEY: MISC_FEATURE
<222> LOCATION: (76)..(76)
<223> OTHER INFORMATION: K or R
<220> FEATURE:
<221> NAME/KEY: MISC_FEATURE
<222> LOCATION: (78)..(78)
<223> OTHER INFORMATION: S or N
<220> FEATURE:
<221> NAME/KEY: MISC_FEATURE
<222> LOCATION: (85)..(85)
<223> OTHER INFORMATION: V or I
<220> FEATURE:
<221> NAME/KEY: MISC_FEATURE
<222> LOCATION: (93)..(93)
<223> OTHER INFORMATION: G or A or S
<220> FEATURE:
<221> NAME/KEY: MISC_FEATURE
<222> LOCATION: (94)..(94)
<223> OTHER INFORMATION: T or L
<220> FEATURE:
<221> NAME/KEY: MISC_FEATURE
<222> LOCATION: (95)..(95)
<223> OTHER INFORMATION: H or Q
<220> FEATURE:
<221> NAME/KEY: MISC_FEATURE
```

```
<222> LOCATION: (96)..(96)
<223> OTHER INFORMATION: W or P or absent
<220> FEATURE:
<221> NAME/KEY: MISC_FEATURE
<222> LOCATION: (97)..(97)
<223> OTHER INFORMATION: P or T or L
<220> FEATURE:
<221> NAME/KEY: MISC_FEATURE
<222> LOCATION: (98)..(98)
<223> OTHER INFORMATION: R or W
<220> FEATURE:
<221> NAME/KEY: MISC_FEATURE
<222> LOCATION: (106)..(106)
<223> OTHER INFORMATION: L or V
<220> FEATURE:
<221> NAME/KEY: MISC_FEATURE
<222> LOCATION: (107)..(107)
<223> OTHER INFORMATION: E or D

<400> SEQUENCE: 28

Xaa Thr Xaa Xaa Pro Leu Ser Leu Xaa Val Thr Xaa Gly Gln Pro Ala
 1               5                  10                  15

Ser Ile Ser Cys Xaa Ser Xaa Gln Ser Leu Xaa Xaa Ser Xaa Gly Xaa
            20                  25                  30

Xaa Xaa Leu Xaa Trp Xaa Xaa Gln Arg Pro Gly Gln Ser Pro Xaa Xaa
        35                  40                  45

Leu Ile Tyr Xaa Val Ser Asn Arg Xaa Ser Gly Val Pro Asp Arg Phe
    50                  55                  60

Ser Gly Ser Gly Ser Gly Thr Asp Phe Thr Leu Xaa Ile Xaa Arg Val
65                  70                  75                  80

Glu Ala Glu Asp Xaa Gly Val Tyr Tyr Cys Met Gln Xaa Xaa Xaa Xaa
                85                  90                  95

Xaa Xaa Thr Phe Gly Gln Gly Thr Lys Xaa Xaa Ile Lys Arg
            100                 105                 110

<210> SEQ ID NO 29
<211> LENGTH: 105
<212> TYPE: PRT
<213> ORGANISM: Artificial Sequence
<220> FEATURE:
<223> OTHER INFORMATION: light chain VL amino acid consensus sequence of
      hFab4.8 and hFab4.9
<220> FEATURE:
<221> NAME/KEY: MISC_FEATURE
<222> LOCATION: (14)..(14)
<223> OTHER INFORMATION: H or D
<220> FEATURE:
<221> NAME/KEY: MISC_FEATURE
<222> LOCATION: (15)..(15)
<223> OTHER INFORMATION: P or R
<220> FEATURE:
<221> NAME/KEY: MISC_FEATURE
<222> LOCATION: (21)..(21)
<223> OTHER INFORMATION: R or Q
<220> FEATURE:
<221> NAME/KEY: MISC_FEATURE
<222> LOCATION: (25)..(25)
<223> OTHER INFORMATION: S or D
<220> FEATURE:
<221> NAME/KEY: MISC_FEATURE
<222> LOCATION: (26)..(26)
<223> OTHER INFORMATION: I or L
<220> FEATURE:
<221> NAME/KEY: MISC_FEATURE
<222> LOCATION: (27)..(27)
<223> OTHER INFORMATION: S or I
<220> FEATURE:
<221> NAME/KEY: MISC_FEATURE
<222> LOCATION: (28)..(28)
<223> OTHER INFORMATION: N or S
<220> FEATURE:
```

```
<221> NAME/KEY: MISC_FEATURE
<222> LOCATION: (34)..(34)
<223> OTHER INFORMATION: H or Q
<220> FEATURE:
<221> NAME/KEY: MISC_FEATURE
<222> LOCATION: (47)..(47)
<223> OTHER INFORMATION: D or A
<220> FEATURE:
<221> NAME/KEY: MISC_FEATURE
<222> LOCATION: (50)..(50)
<223> OTHER INFORMATION: N or I
<220> FEATURE:
<221> NAME/KEY: MISC_FEATURE
<222> LOCATION: (52)..(52)
<223> OTHER INFORMATION: E or Q
<220> FEATURE:
<221> NAME/KEY: MISC_FEATURE
<222> LOCATION: (53)..(53)
<223> OTHER INFORMATION: T or S
<220> FEATURE:
<221> NAME/KEY: MISC_FEATURE
<222> LOCATION: (70)..(70)
<223> OTHER INFORMATION: F or L
<220> FEATURE:
<221> NAME/KEY: MISC_FEATURE
<222> LOCATION: (78)..(78)
<223> OTHER INFORMATION: D or E
<220> FEATURE:
<221> NAME/KEY: MISC_FEATURE
<222> LOCATION: (79)..(79)
<223> OTHER INFORMATION: D or N
<220> FEATURE:
<221> NAME/KEY: MISC_FEATURE
<222> LOCATION: (82)..(82)
<223> OTHER INFORMATION: T or S
<220> FEATURE:
<221> NAME/KEY: MISC_FEATURE
<222> LOCATION: (87)..(87)
<223> OTHER INFORMATION: Q or H
<220> FEATURE:
<221> NAME/KEY: MISC_FEATURE
<222> LOCATION: (89)..(89)
<223> OTHER INFORMATION: D or Y
<220> FEATURE:
<221> NAME/KEY: MISC_FEATURE
<222> LOCATION: (91)..(91)
<223> OTHER INFORMATION: W or F
<220> FEATURE:
<221> NAME/KEY: MISC_FEATURE
<222> LOCATION: (97)..(97)
<223> OTHER INFORMATION: H or Q
<220> FEATURE:
<221> NAME/KEY: MISC_FEATURE
<222> LOCATION: (101)..(101)
<223> OTHER INFORMATION: L or V

<400> SEQUENCE: 29

Met Thr Gln Ser Pro Ser Ser Leu Ser Ala Ser Val Gly Xaa Xaa Val
1               5                   10                  15

Thr Ile Thr Cys Xaa Ala Ser Gln Xaa Xaa Xaa Xaa Tyr Leu Asn Trp
            20                  25                  30

Tyr Xaa Gln Lys Pro Gly Lys Ala Pro Lys Leu Leu Ile Tyr Xaa Ala
        35                  40                  45

Ser Xaa Leu Xaa Xaa Gly Val Pro Ser Arg Phe Ser Gly Ser Gly Ser
    50                  55                  60

Gly Thr Asp Phe Thr Xaa Thr Ile Ser Ser Leu Gln Pro Xaa Xaa Phe
65                  70                  75                  80

Ala Xaa Tyr Tyr Cys Gln Xaa Thr Xaa Ser Xaa Pro Arg Thr Phe Gly
                85                  90                  95

Xaa Gly Thr Lys Xaa Glu Ile Lys Arg
            100                 105
```

<210> SEQ ID NO 30
<211> LENGTH: 663
<212> TYPE: DNA
<213> ORGANISM: Artificial Sequence
<220> FEATURE:
<223> OTHER INFORMATION: heavy chain VH nucleotide sequence

<400> SEQUENCE: 30

```
gaggtccagc tggtacagtc tggtggagcc gtggtccagc ctgggaggtc cctgagactc      60
tcctgtgcag cctctggatt caccttcagt acctatggca tgcactgggt ccgccaggct     120
ccaggcaagg gctggagtg gtggcagct gtatcatatg atggaagtaa taaatactat      180
gcagacttcg tgaaggggcg attcaccatc tccagagaca atcccaagaa caccctgtat     240
ctgcaaatga acagcctgag agccgatgac acggccgtat attactgtgc ccgcagaggt     300
ggtcttgata tctggggcca agggaccacg gtcaccgtct caagcgcctc caccaagggc     360
ccatcggtct tccccctggc accctcctcc aagagcacct ctgggggcac agcggccctg     420
ggctgcctgg tcaaggacta cttccccgaa ccggtgacgg tgtcgtggaa ctcaggcgcc     480
ctgaccagcg gcgtccacac cttcccggct gtcctacagt cctcaggact ctactccctc     540
agcagcgtag tgaccgtgcc ctccagcagc ttgggcaccc agacctacat ctgcaacgtg     600
aatcacaagc ccagcaacac caaggtggac aagaaagttg agcccaaatc ttgtgcggcc     660
gca                                                                   663
```

<210> SEQ ID NO 31
<211> LENGTH: 214
<212> TYPE: PRT
<213> ORGANISM: Artificial Sequence
<220> FEATURE:
<223> OTHER INFORMATION: amino acid sequence of IF7 light chain

<400> SEQUENCE: 31

```
Leu Thr Gln Pro Pro Ala Ser Gly Thr Pro Gly Gln Arg Val Thr
  1               5                  10                  15

Ile Ser Cys Ser Gly Ser Ser Asn Ile Gly Ser Asn Thr Val Asn
                 20                  25                  30

Trp Tyr Gln Gln Leu Pro Gly Thr Ala Pro Lys Leu Leu Ile Tyr Gly
             35                  40                  45

Asn Asp Gln Arg Pro Ser Gly Val Pro Asp Arg Phe Ser Ala Ser Lys
         50                  55                  60

Ser Gly Thr Ser Ala Ser Leu Ala Ile Ser Gly Leu Gln Ser Glu Asp
 65                  70                  75                  80

Glu Ala His Tyr Tyr Cys Ala Ala Trp Asp Gly Ser Leu Asn Gly Gly
                 85                  90                  95

Val Ile Phe Gly Gly Gly Thr Lys Val Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Lys Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190
```

Tyr Ser Cys Gln Val Thr His Glu Gly Ser Thr Val Glu Lys Thr Val
        195                 200                 205

Ala Pro Thr Glu Cys Ser
    210

<210> SEQ ID NO 32
<211> LENGTH: 648
<212> TYPE: DNA
<213> ORGANISM: Artificial Sequence
<220> FEATURE:
<223> OTHER INFORMATION: nucleotide sequence of IF7 light chain

<400> SEQUENCE: 32
ctgactcagc cacccccagc gtctgggacc ccgggcaga gggtcaccat ctcttgttct      60
ggaagcagct ccaacatcgg aagtaatact gtaaactggt accagcaact cccaggaacg     120
gcccccaaac tcctcattta tggtaatgat cagcggccct caggggtccc tgaccgattc     180
tctgcctcca gtctggcac ctcagcctcc ctggccatca gtgggctcca gtctgaggat     240
gaggctcatt attattgtgc agcatgggat ggcagtctga tggtggtgt gatattcggc     300
ggagggacca aggtgaccgt cctgggtcag cccaaggctg cccctcggt cactctgttc     360
ccaccctcct ctgaggagct tcaagccaac aaggccacac tggtgtgtct cataagtgac     420
ttctacccgg agccgtgac agtggcctgg aaggcagata gcagcccgt caaggcggga     480
gtggagacca ccaaaccctc caaacagagc aacaacaagt acgcggccag cagctacctg     540
agcctgacgc cgagcagtg gaagtcccac agaagctaca gctgccaggt cacgcatgaa     600
gggagcaccg tggagaagac agtggcccct acagaatgtt cataataa                 648

<210> SEQ ID NO 33
<211> LENGTH: 648
<212> TYPE: DNA
<213> ORGANISM: Artificial Sequence
<220> FEATURE:
<223> OTHER INFORMATION: nucleotide sequence of hFab4.1 light chain

<400> SEQUENCE: 33
gtgacgcagc cgccctcagc gtctgggacc ccgggcaga gggtcaccat ctcttgttct      60
gggagcagct ccaacatcgg aactaatcct gtaaactggt accagcagct cccaggaacg     120
gcccccaaac tcctcatcta tactactgat cagcggccct caggggtccc tgaccgcttc     180
tctggctcca gtctggcac ctcagcctcc ctggccatca gtgggctcca gtctgaggat     240
gaggctgatt attactgtgc agcatgggat gacagcctga gtggcctta tgtcttcggg     300
actgggacca aggtcaccgt cctcggtcag cccaaggcca ccccactgt cactctgttc     360
ccgcccctcct ctgaggagct ccaagccaac aaggccacac tagtgtgtct gatcagtgac     420
ttctacccgg agctgtgac agtggcctgg aaggcagatg gcagcccgt caaggcggga     480
gtggagacca ccaaaccctc caaacagagc aacaacaagt acgcggccag cagctacctg     540
agcctgacgc cgagcagtg gaagtcccac agaagctaca gctgccaggt cacgcatgaa     600
gggagcaccg tggagaagac agtggcccct gcagaatgct cttaataa                 648

<210> SEQ ID NO 34
<211> LENGTH: 651
<212> TYPE: DNA
<213> ORGANISM: Artificial Sequence
<220> FEATURE:
<223> OTHER INFORMATION: nucleotide sequence of hFab4.2 light chain

<400> SEQUENCE: 34

```
atgacccaca ctccattgtc tctgtccgtc acccctggac agccggcctc catctcctgc    60
aagtctagtc agagtctctt gcatagtgat ggaaagacct atttgtattg gtacctgcag   120
aggccaggcc agtctccaca gcccctgatc tatgaagttt ccaaccggtt ctctggagtg   180
ccagataggt tcagtggcag cgggtcaggg acagatttca cactgaaaat cagccgggtg   240
gaggctgagg atgtcggggt ttattactgc atgcaaagtc tacaactctg acgttcggc    300
caagggacca aggtggaaat caaacgaact gtggctgcac catctgtctt catcttccg    360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagactac gagaaacac aaagtctacg cctgcgaagt cacccatcag   600
ggcctgagct cgcccgtcac aaagagcttc aacaggggag agtgttaata a            651
```

<210> SEQ ID NO 35
<211> LENGTH: 654
<212> TYPE: DNA
<213> ORGANISM: Artificial Sequence
<220> FEATURE:
<223> OTHER INFORMATION: nucleotide sequence of hFab4.3 light chain

<400> SEQUENCE: 35

```
atgactcagt ctccactctc cctgcccgtc acccttggac agccggcctc catctcctgc    60
aggtctagtc aaagcctcat acacagtgat ggaaacacgt acttggattg gtttcagcag   120
aggccaggcc aatctccaag cgcctaatt tataaggttt ctaaccggga ctctggggtc    180
ccagacagat tcagcggcag tgggtccggc actgatttca cactgagaat cagcagggtg   240
gaggctgagg atattggggt gtattactgc atgcaagcta cacactggcc tcggacgttc   300
ggccagggga ccaaggtgga aatcaaacga actgtggctg caccatctgt cttcatcttc   360
ccgccatctg atgagcagtt gaaatctgga actgcctctg ttgtgtgcct gctgaataac   420
ttctatccca gagaggccaa agtacagtgg aaggtggata cgccctcca atcgggtaac   480
tcccaggaga gtgtcacaga gcaggacagc aaggacagca cctacagcct cagcagcacc   540
ctgacgctga gcaaagcaga ctacgagaaa cacaaagtct acgcctgcga agtcacccat   600
cagggcctga gctcgcccgt cacaaagagc ttcaacaggg gagagtgtta ataa          654
```

<210> SEQ ID NO 36
<211> LENGTH: 654
<212> TYPE: DNA
<213> ORGANISM: Artificial Sequence
<220> FEATURE:
<223> OTHER INFORMATION: nucleotide sequence of hFab4.4 light chain

<400> SEQUENCE: 36

```
atgactcagt ctccactctc cctgcccgtc acccttggac agccggcctc catctcctgc    60
aggtctagtc aaagcctcgt agacagtgct ggaaacacct tcttgcattg gtttcaccag   120
aggccaggcc aatctccaag cgcctaatt tataaggttt ctaaccggga ctctggggtc    180
ccagacagat tcagcggcag tgggtcaggc actgatttca cactgaaaat cagcagggtg   240
gaggctgagg atgttggggt ttattactgt atgcaaggta cacactggcc ccggacgttc   300
ggccaaggga ccaaggtgga aatcaaacga actgtggctg caccatctgt cttcatcttc   360
ccgccatctg atgagcagtt gaaatctgga actgcctctg ttgtgtgcct gctgaataac   420
```

```
ttctatccca gagaggccaa agtacagtgg aaggtggata acgccctcca atcgggtaac    480
tcccaggaga gtgtcacaga gcaggacagc aaggacagca cctacagcct cagcagcacc    540
ctgacgctga gcaaagcaga ctacgagaaa cacaaagtct acgcctgcga agtcacccat    600
cagggcctga gctcgcccgt cacaaagagc ttcaacaggg gagagtgtta ataa          654
```

<210> SEQ ID NO 37
<211> LENGTH: 654
<212> TYPE: DNA
<213> ORGANISM: Artificial Sequence
<220> FEATURE:
<223> OTHER INFORMATION: nucleotide sequence of hFab4.5 light chain

<400> SEQUENCE: 37

```
ctgactcagt ctccactctc cctgcccgtc acccttggac agccggcctc catctcctgc    60
aagtctagtc aaagcctcgt agacagtgat ggaaacacct acttgaattg gtttcagcag   120
aggccaggcc aatctccaag gcgcctaatt tataaggttt ctaaccggga ctctggggtc   180
ccagacagat tcagcggcag tgggtcaggc actgatttca cactgaaaat cagcagggtg   240
gaggctgagg atgttggggt ttattactgc atgcaaggta cacactggcc tcggacgttc   300
ggccaaggga ccaaggtgga aatcaaacga actgtggctg caccatctgt cttcatcttc   360
ccgccatctg atgagcagtt gaaatctgga actgcctctg ttgtgtgcct gctgaataac   420
ttctatccca gagaggccaa agtacagtgg aaggtggata acgccctcca atcgggtaac   480
tcccaggaga gtgtcacaga gcaggacagc aaggacagca cctacagcct cagcagcacc   540
ctgacgctga gcaaagcaga ctacgagaaa cacaaagtct acgcctgcga agtcacccat   600
cagggcctga gctcgcccgt cacaaagagc ttcaacaggg gagagtgtta ataa          654
```

<210> SEQ ID NO 38
<211> LENGTH: 693
<212> TYPE: DNA
<213> ORGANISM: Artificial Sequence
<220> FEATURE:
<223> OTHER INFORMATION: nucleotide sequence of hFab4.7 light chain

<400> SEQUENCE: 38

```
atgactcagt ctccactctc cctgcccgtc acccttggac agccggcctc catctcctgc    60
aggtctagtc aaagcctcgt acacagtgat ggaaacatgt acttgaattg gtttcagcag   120
aggccaggcc aatctccaag gcgcctaatt tataaggttt ctaaccggga ctctggggtc   180
ccagacagat tcagcggcag tgggtcaggc acagatttta cactgaaaat cagcagagtg   240
gaggctgagg atgttggggt ttattactgc atgcaagcta cacagcccac gtggacgttc   300
ggccaaggga ccaagctgga gatcaaacga actgtggctg caccatctgt cttcatcttc   360
ccgccatctg atgagcagtt gaaatctgga actgcctctg ttgtgtgcct gctgaataac   420
ttctatccca gagaggccaa agtacagtgg aaggtggata acgccctcca atcgggtaac   480
tcccaggaga gtgtcacaga gcaggacagc aaggacagca cctacagcct cagcagcacc   540
ctgacgctga gcaaaagcag actacgagaa acacaaagtc tacgcctgcg aagtcaccca   600
tcagggcctg agctcgcccg tcacaaagag cttcaacagg ggagagtgtt aataaggcgc   660
gccaattcta tttcaaggag acagtcataa tga                                 693
```

<210> SEQ ID NO 39
<211> LENGTH: 677
<212> TYPE: DNA

<213> ORGANISM: Artificial Sequence
<220> FEATURE:
<223> OTHER INFORMATION: nucleotide sequence of hFab4.8 light chain

<400> SEQUENCE: 39

```
atgacccagt ctccatcctc cctgtctgca tctgtaggag acagagtcac catcacttgc      60
caggcgagtc aggacattag caactattta aattggtatc agcagaaacc agggaaagcc     120
cctaagctcc tgatctacga tgcatccaat ttggaaacag ggtcccatc aaggttcagt      180
ggaagtggat ctgggacaga ttttactttc accatcagca gcctgcaacc tgacgatttt     240
gcaacttact actgtcaaca gacttacagt tggcctcgga cttttggcca ggggaccaag     300
ctggagatca aacgaactgt ggctgcacca tctgtcttca tcttcccgcc atctgatgag     360
cagttgaaat ctggaactgc ctctgttgtg tgcctgctga ataacttcta tcccagagag     420
gccaaagtac agtggaaggt ggataacgcc ctccaatcgg gtaactccca ggagagtgtc     480
acagagcagg acagcaagga cagcacctac agcctcagca gcaccctgac gctgagcaaa     540
gcagactacg agaaacacaa agtctacgcc tgcgaagtca cccatcaggg cctgagctcg     600
cccgtcacaa agagcttcaa caggggagag tgttaataag gcgcgccaat tctatttcaa     660
ggagacagtc ataatga                                                    677
```

<210> SEQ ID NO 40
<211> LENGTH: 639
<212> TYPE: DNA
<213> ORGANISM: Artificial Sequence
<220> FEATURE:
<223> OTHER INFORMATION: nucleotide sequence of hFab4.9 light chain

<400> SEQUENCE: 40

```
atgacccagt ctccatcctc cctgtccgca tctgtaggac acccagtcac catcacttgc      60
cgggcaagtc aaagccttat cagctattta aattggtatc accagaaacc agggaaagcc     120
cctaagctcc tgatctatgc ggcatccatt ttgcaaagtg ggtcccatc aaggttcagt      180
ggcagtggat ctgggacaga tttcactctc accatcagca gtctgcaacc tgaaaatttt     240
gcaagttact actgtcaaca taccgacagt ttccctcgga cgttcggcca cgggaccaag     300
gtggaaatca aacgaactgt ggctgcacca tctgtcttca tcttcccgcc atctgatgac     360
cagttgaaat ctggaactgc ctccgttgtg tgcctgctga ataacttcta tcccaaaaag     420
gccaaagtac aatggaaggt ggataacgcc ctcgagtcgg gtaactccca ggagagtgtc     480
acagagcagg acgtcaagga cagcacctac agcctcagca gcaccctgac gctgagcaaa     540
gccggactac gagaaaccaa agtctacgcc tgcgaagtca cccatctgcg aactgagctc     600
tcccgtcaca aagagcttca caggggagag tgttaataa                            639
```

<210> SEQ ID NO 41
<211> LENGTH: 645
<212> TYPE: DNA
<213> ORGANISM: Artificial Sequence
<220> FEATURE:
<223> OTHER INFORMATION: nucleotide sequence of hFab4.10 light chain

<400> SEQUENCE: 41

```
ctgactcagc cccctcagc gtctgggacc cccgggcagg gtgtcaccat ctcctgtcgt       60
ggaagcacct ccaacatcgg aaataatgtt gttaattggt atcaacatgt cccgggatcg     120
gccccccaaac tcctcatctg gagtaatatt cagcggccct cagggattcc tgaccgattc     180
tctggctcca agtctggcac ctcagcctcc ctggccatca gtggacttca gtctgaagat     240
```

```
gaggctgttt attactgtgc agtctgggat acggcctgg ctggttgggt gttcggcgga    300
gggaccacgg tgaccgtcct aagtcagccc aaggctgccc cctcggtcac tctgttcccg    360
ccctcctctg aggagcttca agccaacaag gccacactgg tgtgtctcat aagtgacttc    420
tacccgggag ccgtgacagt ggcctggaag gcagatagca gccccgtcaa ggcgggagtg    480
gagaccacca cccctccaa acaaagcaac aacaagtacg cggccagcag ctacctgagc    540
ctgacgcctg agcagtggaa gtcccacaaa agctacagct gccaggtcac gcatgaaggg    600
agcaccgtgg agaagacagt ggcccctaca gaatgttcat aataa                   645

<210> SEQ ID NO 42
<211> LENGTH: 639
<212> TYPE: DNA
<213> ORGANISM: Artificial Sequence
<220> FEATURE:
<223> OTHER INFORMATION: nucleotide sequence of hFab4.12 light chain

<400> SEQUENCE: 42
atgactcagg cccctgttgt gtcggtggcc ttggaacaaa cagtcaggat cacatgccaa     60
ggagacagcc tagcaatcta ttatgatttc tggtaccagc acaagccagg acaggcccct    120
gtacttgtca tctatggtaa aaacaaccgg ccctcaggga tcccccaccg attctctggc    180
tccagctcat gaaacacaga ttccttgacc atcactgggg ctcaggcgga agatgaggct    240
gactattact gtaactcccg ggacagcagt ggtaaccatt gggtgttcgg cggagggacc    300
aacctgaccg tcctaggtca acccaaggct gcccccctcgg ccattctgtt cccgccctcc    360
tctgaggagc ttcaaactaa cacggctaca tgggtgtgtc tcatatttga cttctacccg    420
ggagctgtaa cagtggccgg gaatgcagat ggcaaccccg tcaacgccgg agtggatacc    480
accaaaccct actgccagaa caacaactac tacgcggcca gcacctacct gatcatgacg    540
cctgaccagt ggaaatccca cttcagctac agctaactcg tcacgcatga agggagctcc    600
gtggacaaga aaatggcccc tgcagaatgc tcttaataa                           639

<210> SEQ ID NO 43
<211> LENGTH: 654
<212> TYPE: DNA
<213> ORGANISM: Artificial Sequence
<220> FEATURE:
<223> OTHER INFORMATION: nucleotide sequence of hFab4.18 light chain

<400> SEQUENCE: 43
ctgactcagt ctccactctc cctgcccgtc acccttggac agccggcctc catctcctgc     60
aagtctaatc aaagcctcgt acacagtgat ggaaacacct acttgaattg gtttcagcag    120
aggccaggcc aatctccaag gcgcctaatc tataaggttt ctaaccggga ctctggggtc    180
ccagacagat tcagcggcag tgggtcaggc actgatttca cactgaaaat caacagggtg    240
gaggctgaga tgttggggt ttattactgc atgcaaggta cacagtggcc tcggactttt    300
ggccagggga ccaagctgga catcaaacga actgtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggata cgccctccaa atcgggtaac    480
tcccaggaga gtgtcacaga gcaggacagc aaggacagca cctacagcct cagcagcacc    540
ctgacgctga gcaaagcaaa ctacaagaaa cacaaagtct acgcctgcga agtcacccat    600
cagggcctga cctcgcccgt cacaaagagc ttcaacaagg gagagtgtta ataa          654
```

```
<210> SEQ ID NO 44
<211> LENGTH: 205
<212> TYPE: PRT
<213> ORGANISM: Homo sapiens

<400> SEQUENCE: 44

Met Ser Arg Gly Leu Gln Leu Leu Leu Ser Cys Ala Tyr Ser Leu
1               5                   10                  15

Ala Pro Ala Thr Pro Glu Val Lys Val Ala Cys Ser Glu Asp Val Asp
            20                  25                  30

Leu Pro Cys Thr Ala Pro Trp Asp Pro Gln Val Pro Tyr Thr Val Ser
            35                  40                  45

Trp Val Lys Leu Leu Glu Gly Gly Glu Glu Arg Met Glu Thr Pro Gln
50                  55                  60

Glu Asp His Leu Arg Gly Gln His Tyr His Gln Lys Gly Gln Asn Gly
65                  70                  75                  80

Ser Phe Asp Ala Pro Asn Glu Arg Pro Tyr Ser Leu Lys Ile Arg Asn
                85                  90                  95

Thr Thr Ser Cys Asn Ser Gly Thr Tyr Arg Cys Thr Leu Gln Asp Pro
                100                 105                 110

Asp Gly Gln Arg Asn Leu Ser Gly Lys Val Ile Leu Arg Val Thr Gly
            115                 120                 125

Cys Pro Ala Gln Arg Lys Glu Glu Thr Phe Lys Lys Tyr Arg Ala Glu
130                 135                 140

Ile Val Leu Leu Leu Ala Leu Val Ile Phe Tyr Leu Thr Leu Ile Ile
145                 150                 155                 160

Phe Thr Cys Lys Phe Ala Arg Leu Gln Ser Ile Phe Pro Asp Phe Ser
                165                 170                 175

Lys Ala Gly Met Glu Arg Ala Phe Leu Pro Val Thr Ser Pro Asn Lys
                180                 185                 190

His Leu Gly Leu Val Thr Pro His Lys Thr Glu Leu Val
            195                 200                 205

<210> SEQ ID NO 45
<211> LENGTH: 204
<212> TYPE: PRT
<213> ORGANISM: Homo sapiens

<400> SEQUENCE: 45

Met Ser Arg Gly Leu Gln Leu Leu Leu Ser Cys Ala Tyr Ser Leu
1               5                   10                  15

Ala Pro Ala Thr Pro Glu Val Lys Val Ala Cys Ser Glu Asp Val Asp
            20                  25                  30

Leu Pro Cys Thr Ala Pro Trp Asp Pro Gln Val Pro Tyr Thr Val Ser
            35                  40                  45

Trp Val Lys Leu Leu Glu Gly Gly Glu Glu Arg Met Glu Thr Pro Gln
50                  55                  60

Glu Asp His Leu Arg Gly Gln His Tyr His Gln Lys Gly Gln Asn Gly
65                  70                  75                  80

Ser Phe Asp Ala Pro Asn Glu Arg Pro Tyr Ser Leu Lys Ile Arg Asn
                85                  90                  95

Thr Thr Ser Cys Asn Ser Gly Thr Tyr Arg Cys Thr Leu Gln Asp Pro
                100                 105                 110

Asp Gly Gln Arg Asn Leu Ser Gly Lys Val Ile Leu Arg Val Thr Gly
            115                 120                 125
```

Cys Pro Ala Gln Arg Lys Glu Glu Thr Phe Lys Lys Tyr Arg Ala Glu
    130                 135                 140

Ile Val Leu Leu Leu Ala Leu Val Ile Phe Tyr Leu Thr Leu Ile Ile
145                 150                 155                 160

Phe Thr Cys Phe Ala Arg Leu Gln Ser Ile Phe Pro Asp Phe Ser Lys
            165                 170                 175

Ala Gly Met Glu Arg Ala Phe Leu Pro Val Thr Ser Pro Asn Lys His
            180                 185                 190

Leu Gly Leu Val Thr Pro His Lys Thr Glu Leu Val
            195                 200

<210> SEQ ID NO 46
<211> LENGTH: 146
<212> TYPE: PRT
<213> ORGANISM: Homo sapiens

<400> SEQUENCE: 46

Met Glu Thr Pro Gln Glu Asp His Leu Arg Gly Gln His Tyr His Gln
1               5                   10                  15

Lys Gly Gln Asn Gly Ser Phe Asp Ala Pro Asn Glu Arg Pro Tyr Ser
            20                  25                  30

Leu Lys Ile Arg Asn Thr Thr Ser Cys Asn Ser Gly Thr Tyr Arg Cys
        35                  40                  45

Thr Leu Gln Asp Pro Asp Gly Gln Arg Asn Leu Ser Gly Lys Val Ile
    50                  55                  60

Leu Arg Val Thr Gly Cys Pro Ala Gln Arg Lys Glu Glu Thr Phe Lys
65                  70                  75                  80

Lys Tyr Arg Ala Glu Ile Val Leu Leu Leu Ala Leu Val Ile Phe Tyr
                85                  90                  95

Leu Thr Leu Ile Ile Phe Thr Cys Lys Phe Ala Arg Leu Gln Ser Ile
                100                 105                 110

Phe Pro Asp Phe Ser Lys Ala Gly Met Glu Arg Ala Phe Leu Pro Val
            115                 120                 125

Thr Ser Pro Asn Lys His Leu Gly Leu Val Thr Pro His Lys Thr Glu
        130                 135                 140

Leu Val
145

<210> SEQ ID NO 47
<211> LENGTH: 25
<212> TYPE: DNA
<213> ORGANISM: Artificial Sequence
<220> FEATURE:
<223> OTHER INFORMATION: nucleotide sequence of pFUSE VH 4.4 For primer

<400> SEQUENCE: 47
gaattcggag gtccagctgg tacag                                    25

<210> SEQ ID NO 48
<211> LENGTH: 26
<212> TYPE: DNA
<213> ORGANISM: Artificial Sequence
<220> FEATURE:
<223> OTHER INFORMATION: nucleotide sequence of pFUSE VH 4.4 Rev primer

<400> SEQUENCE: 48
gctagcgctt gagacggtga ccgtgg                                   26

<210> SEQ ID NO 49

```
<211> LENGTH: 32
<212> TYPE: DNA
<213> ORGANISM: Artificial Sequence
<220> FEATURE:
<223> OTHER INFORMATION: nucleotide sequence of pFUSE VL 4.4 For primer

<400> SEQUENCE: 49
gaattcagat gttgtgatga ctcagtctcc ac                                     32

<210> SEQ ID NO 50
<211> LENGTH: 31
<212> TYPE: DNA
<213> ORGANISM: Artificial Sequence
<220> FEATURE:
<223> OTHER INFORMATION: nucleotide sequence of pFUSE VL 4.4 Rev primer

<400> SEQUENCE: 50
cgtacgtttg atttccacct tggtcccttg g                                      31

<210> SEQ ID NO 51
<211> LENGTH: 13
<212> TYPE: PRT
<213> ORGANISM: Artificial Sequence
<220> FEATURE:
<223> OTHER INFORMATION: WT1F7 CDR1

<400> SEQUENCE: 51

Ser Gly Ser Ser Ser Asn Ile Gly Ser Asn Thr Val Asn
1               5                   10

<210> SEQ ID NO 52
<211> LENGTH: 6
<212> TYPE: PRT
<213> ORGANISM: Artificial Sequence
<220> FEATURE:
<223> OTHER INFORMATION: WT1F7 CDR2

<400> SEQUENCE: 52

Gly Asn Asp Gln Arg Pro
1               5

<210> SEQ ID NO 53
<211> LENGTH: 12
<212> TYPE: PRT
<213> ORGANISM: Artificial Sequence
<220> FEATURE:
<223> OTHER INFORMATION: WT1F7 CDR3

<400> SEQUENCE: 53

Ala Ala Trp Asp Gly Ser Leu Asn Gly Gly Val Ile
1               5                   10

<210> SEQ ID NO 54
<211> LENGTH: 13
<212> TYPE: PRT
<213> ORGANISM: Artificial Sequence
<220> FEATURE:
<223> OTHER INFORMATION: hFab4.1 CDR1

<400> SEQUENCE: 54

Ser Gly Ser Ser Ser Asn Ile Gly Thr Asn Pro Val Asn
1               5                   10

<210> SEQ ID NO 55
<211> LENGTH: 6
<212> TYPE: PRT
<213> ORGANISM: Artificial Sequence
```

```
<220> FEATURE:
<223> OTHER INFORMATION: hFab4.1 CDR2

<400> SEQUENCE: 55

Thr Thr Asp Gln Arg Pro
1               5

<210> SEQ ID NO 56
<211> LENGTH: 12
<212> TYPE: PRT
<213> ORGANISM: Artificial Sequence
<220> FEATURE:
<223> OTHER INFORMATION: hFab4.1 CDR3

<400> SEQUENCE: 56

Ala Ala Trp Asp Asp Ser Leu Ser Gly Leu Tyr Val
1               5                   10

<210> SEQ ID NO 57
<211> LENGTH: 16
<212> TYPE: PRT
<213> ORGANISM: Artificial Sequence
<220> FEATURE:
<223> OTHER INFORMATION: hFab 4.2 CDR1

<400> SEQUENCE: 57

Lys Ser Ser Gln Ser Leu Leu His Ser Asp Gly Lys Thr Tyr Leu Tyr
1               5                   10                  15

<210> SEQ ID NO 58
<211> LENGTH: 6
<212> TYPE: PRT
<213> ORGANISM: Artificial Sequence
<220> FEATURE:
<223> OTHER INFORMATION: hFab 4.2 CDR2

<400> SEQUENCE: 58

Glu Val Ser Asn Arg Phe
1               5

<210> SEQ ID NO 59
<211> LENGTH: 8
<212> TYPE: PRT
<213> ORGANISM: Artificial Sequence
<220> FEATURE:
<223> OTHER INFORMATION: hFab 4.2 CDR3

<400> SEQUENCE: 59

Met Gln Ser Leu Gln Leu Trp Thr
1               5

<210> SEQ ID NO 60
<211> LENGTH: 16
<212> TYPE: PRT
<213> ORGANISM: Artificial Sequence
<220> FEATURE:
<223> OTHER INFORMATION: hFab 4.3 CDR1

<400> SEQUENCE: 60

Arg Ser Ser Gln Ser Leu Ile His Ser Asp Gly Asn Thr Tyr Leu Asp
1               5                   10                  15

<210> SEQ ID NO 61
<211> LENGTH: 6
<212> TYPE: PRT
<213> ORGANISM: Artificial Sequence
<220> FEATURE:
```

<223> OTHER INFORMATION: hFab 4.3 CDR2

<400> SEQUENCE: 61

Lys Val Ser Asn Arg Asp
1               5

<210> SEQ ID NO 62
<211> LENGTH: 9
<212> TYPE: PRT
<213> ORGANISM: Artificial Sequence
<220> FEATURE:
<223> OTHER INFORMATION: hFab 4.3 CDR3

<400> SEQUENCE: 62

Met Gln Ala Thr His Trp Pro Arg Thr
1               5

<210> SEQ ID NO 63
<211> LENGTH: 16
<212> TYPE: PRT
<213> ORGANISM: Artificial Sequence
<220> FEATURE:
<223> OTHER INFORMATION: hFab 4.4 CDR1

<400> SEQUENCE: 63

Arg Ser Ser Gln Ser Leu Val Asp Ser Ala Gly Asn Thr Phe Leu His
1               5                   10                  15

<210> SEQ ID NO 64
<211> LENGTH: 6
<212> TYPE: PRT
<213> ORGANISM: Artificial Sequence
<220> FEATURE:
<223> OTHER INFORMATION: hFab 4.4 CDR2

<400> SEQUENCE: 64

Lys Val Ser Asn Arg Asp
1               5

<210> SEQ ID NO 65
<211> LENGTH: 9
<212> TYPE: PRT
<213> ORGANISM: Artificial Sequence
<220> FEATURE:
<223> OTHER INFORMATION: hFab 4.4 CDR3

<400> SEQUENCE: 65

Met Gln Gly Thr His Trp Pro Arg Thr
1               5

<210> SEQ ID NO 66
<211> LENGTH: 16
<212> TYPE: PRT
<213> ORGANISM: Artificial Sequence
<220> FEATURE:
<223> OTHER INFORMATION: hFab 4.5 CDR1

<400> SEQUENCE: 66

Lys Ser Ser Gln Ser Leu Val Asp Ser Asp Gly Asn Thr Tyr Leu Asn
1               5                   10                  15

<210> SEQ ID NO 67
<211> LENGTH: 6
<212> TYPE: PRT
<213> ORGANISM: Artificial Sequence
<220> FEATURE:
<223> OTHER INFORMATION: hFab 4.5 CDR2

```
<400> SEQUENCE: 67

Lys Val Ser Asn Arg Asp
1               5

<210> SEQ ID NO 68
<211> LENGTH: 9
<212> TYPE: PRT
<213> ORGANISM: Artificial Sequence
<220> FEATURE:
<223> OTHER INFORMATION: hFab 4.5 CDR3

<400> SEQUENCE: 68

Met Gln Gly Thr His Trp Pro Arg Thr
1               5

<210> SEQ ID NO 69
<211> LENGTH: 16
<212> TYPE: PRT
<213> ORGANISM: Artificial Sequence
<220> FEATURE:
<223> OTHER INFORMATION: hFab 4.7 CDR1

<400> SEQUENCE: 69

Arg Ser Ser Gln Ser Leu Val His Ser Asp Gly Asn Met Tyr Leu Asn
1               5                   10                  15

<210> SEQ ID NO 70
<211> LENGTH: 6
<212> TYPE: PRT
<213> ORGANISM: Artificial Sequence
<220> FEATURE:
<223> OTHER INFORMATION: hFab 4.7 CDR2

<400> SEQUENCE: 70

Lys Val Ser Asn Arg Asp
1               5

<210> SEQ ID NO 71
<211> LENGTH: 9
<212> TYPE: PRT
<213> ORGANISM: Artificial Sequence
<220> FEATURE:
<223> OTHER INFORMATION: hFab 4.7 CDR3

<400> SEQUENCE: 71

Met Gln Ala Thr Gln Pro Thr Trp Thr
1               5

<210> SEQ ID NO 72
<211> LENGTH: 11
<212> TYPE: PRT
<213> ORGANISM: Artificial Sequence
<220> FEATURE:
<223> OTHER INFORMATION: hFab 4.8 CDR1

<400> SEQUENCE: 72

Gln Ala Ser Gln Asp Ile Ser Asn Tyr Leu Asn
1               5                   10

<210> SEQ ID NO 73
<211> LENGTH: 6
<212> TYPE: PRT
<213> ORGANISM: Artificial Sequence
<220> FEATURE:
<223> OTHER INFORMATION: hFab 4.8 CDR2
```

<400> SEQUENCE: 73

Asp Ala Ser Asn Leu Glu
1               5

<210> SEQ ID NO 74
<211> LENGTH: 9
<212> TYPE: PRT
<213> ORGANISM: Artificial Sequence
<220> FEATURE:
<223> OTHER INFORMATION: hFab 4.8 CDR3

<400> SEQUENCE: 74

Gln Gln Thr Tyr Ser Trp Pro Arg Thr
1               5

<210> SEQ ID NO 75
<211> LENGTH: 11
<212> TYPE: PRT
<213> ORGANISM: Artificial Sequence
<220> FEATURE:
<223> OTHER INFORMATION: hFab 4.9 CDR1

<400> SEQUENCE: 75

Arg Ala Ser Gln Ser Leu Ile Ser Tyr Leu Asn
1               5                   10

<210> SEQ ID NO 76
<211> LENGTH: 6
<212> TYPE: PRT
<213> ORGANISM: Artificial Sequence
<220> FEATURE:
<223> OTHER INFORMATION: hFab 4.9 CDR2

<400> SEQUENCE: 76

Ala Ala Ser Ile Leu Gln
1               5

<210> SEQ ID NO 77
<211> LENGTH: 9
<212> TYPE: PRT
<213> ORGANISM: Artificial Sequence
<220> FEATURE:
<223> OTHER INFORMATION: hFab 4.9 CDR3

<400> SEQUENCE: 77

Gln His Thr Asp Ser Phe Pro Arg Thr
1               5

<210> SEQ ID NO 78
<211> LENGTH: 13
<212> TYPE: PRT
<213> ORGANISM: Artificial Sequence
<220> FEATURE:
<223> OTHER INFORMATION: hFab 4.10 CDR1

<400> SEQUENCE: 78

Arg Gly Ser Thr Ser Asn Ile Gly Asn Asn Val Val Asn
1               5                   10

<210> SEQ ID NO 79
<211> LENGTH: 6
<212> TYPE: PRT
<213> ORGANISM: Artificial Sequence
<220> FEATURE:
<223> OTHER INFORMATION: hFab 4.10 CDR2

<400> SEQUENCE: 79

```
Ser Asn Ile Gln Arg Pro
1               5

<210> SEQ ID NO 80
<211> LENGTH: 11
<212> TYPE: PRT
<213> ORGANISM: Artificial Sequence
<220> FEATURE:
<223> OTHER INFORMATION: hFab 4.10 CDR3

<400> SEQUENCE: 80

Ala Val Trp Asp Asp Gly Leu Ala Gly Trp Val
1               5                   10

<210> SEQ ID NO 81
<211> LENGTH: 11
<212> TYPE: PRT
<213> ORGANISM: Artificial Sequence
<220> FEATURE:
<223> OTHER INFORMATION: hFab 4.12 CDR1

<400> SEQUENCE: 81

Gln Gly Asp Ser Leu Ala Ile Tyr Tyr Asp Phe
1               5                   10

<210> SEQ ID NO 82
<211> LENGTH: 6
<212> TYPE: PRT
<213> ORGANISM: Artificial Sequence
<220> FEATURE:
<223> OTHER INFORMATION: hFab 4.12 CDR2

<400> SEQUENCE: 82

Gly Lys Asn Asn Arg Pro
1               5

<210> SEQ ID NO 83
<211> LENGTH: 11
<212> TYPE: PRT
<213> ORGANISM: Artificial Sequence
<220> FEATURE:
<223> OTHER INFORMATION: hFab 4.12 CDR3

<400> SEQUENCE: 83

Asn Ser Arg Asp Ser Ser Gly Asn His Trp Val
1               5                   10

<210> SEQ ID NO 84
<211> LENGTH: 16
<212> TYPE: PRT
<213> ORGANISM: Artificial Sequence
<220> FEATURE:
<223> OTHER INFORMATION: hFab 4.18 CDR1

<400> SEQUENCE: 84

Lys Ser Asn Gln Ser Leu Val His Ser Asp Gly Asn Thr Tyr Leu Asn
1               5                   10                  15

<210> SEQ ID NO 85
<211> LENGTH: 6
<212> TYPE: PRT
<213> ORGANISM: Artificial Sequence
<220> FEATURE:
<223> OTHER INFORMATION: hFab 4.18 CDR2

<400> SEQUENCE: 85
```

```
Lys Val Ser Asn Arg Asp
1               5

<210> SEQ ID NO 86
<211> LENGTH: 9
<212> TYPE: PRT
<213> ORGANISM: Artificial Sequence
<220> FEATURE:
<223> OTHER INFORMATION: hFab 4.18 CDR3

<400> SEQUENCE: 86

Met Gln Gly Thr Gln Trp Pro Arg Thr
1               5
```

CD83 BINDING PROTEINS AND USES THEREOF

CROSS-REFERENCE TO RELATED APPLICATIONS

This application is a national phase application of International Application No. PCT/AU2015/000635, filed Oct. 23, 2015, and claims the priority of Australian Application No. 2014904236, filed Oct. 23, 2014, the content of both of which is incorporated herein by reference.

FIELD

The present disclosure relates to proteins that bind to CD83 and uses thereof, for example, in therapy, prophylaxis, diagnosis, or prognosis.

BACKGROUND

CD83

CD83 is a 45 kDa, type-I membrane glycoprotein belonging to the immunoglobulin superfamily. CD83 is a cell surface marker predominantly expressed on mature dendritic cells (DCs). CD83 is minimally expressed on immature blood DC (BDC) and monocyte derived DC (MoDC). Due to its preferential expression on mature DCs, CD83 is an attractive target for immunotherapy.

Dendritic Cells and the Control of Innate and Adaptive Immune Responses

DCs link the innate and cognate (adaptive) immune systems. Innate immunity is the primary driver of non-specific immune activation in response to foreign agents. Immature DCs specialize in the internalisation of antigens and are distributed throughout peripheral tissues allowing for continuous antigenic surveillance. Termed professional antigen presenting cells (APCs) for their capability to drive primary T cell responses, DCs only require minimal quantities of antigen to initiate immune activation.

Immature DCs are attuned to a variety of signals from infectious and foreign material, which trigger differentiation and maturation (also known as activation) of the DCs. Whilst mature DCs are capable of antigen capture, this activation process reduces the capacity of these cells to internalize antigen, instead up-regulating cytokine release, activation marker expression and processing of antigen for major histocompatibility complex (MHC) presentation. Mature DCs loaded with processed antigen can efficiently recruit T cells, B cells, granulocytes, natural killer (NK) cells, monocytes and other cells of the innate immune system to amplify the response to antigen.

The molecules which become expressed upon DC differentiation and activation aid in linking innate and adaptive immunity. Mature DCs up-regulate the expression of chemokine receptors and adhesion molecules such as CD54, facilitating DC migration to lymph nodes for increased interaction with lymphocytes. Expression of co-stimulatory molecules, such as CD80 and CD86, provides the requisite co-stimulatory signals for T cell activation and the initiation of an antigen-specific immune response. Ligation of CD40 enhances the expression of co-stimulatory molecules and induces the release of IL-12 to facilitate T cell activation; differentiated T cells then orchestrate the complex interactions of the adaptive immune response.

Since DCs exert control over immune responses, activated DCs can be viewed as a target for intervention across a number of immunological diseases including malignancy and autoimmune diseases.

It will be apparent to the skilled person from the foregoing that compounds that target DCs may modulate the immune response. Accordingly, compounds that bind DCs are desirable, for example, for their therapeutic, prophylactic, diagnostic and prognostic uses.

SUMMARY

The present disclosure is based on the inventors' production of a human antibody (1F7 mAb) that binds specifically to CD83. 1F7 mAb was derived from a phage display library of human Fab sequences; the obtained Fab phage clone reformatted as an IgG1 mAb.

To improve the therapeutic efficacy of the 1F7 mAb, the inventors performed affinity maturation of the light chain to improve the affinity of the 1F7 mAb for CD83. Eleven new 1F7 Fab variants with distinct light chain variable region ($V_L$) sequences and enhanced binding properties relative to the wild type Fab were obtained. The affinity matured antibodies included substitutions in the framework (FR) and complementarity determining regions (CDRs) of the $V_L$. The effect of these substitutions was not predictable.

The present disclosure is broadly directed to a CD83 binding protein comprising an antigen binding domain which specifically binds to CD83.

In one example, the present disclosure provides a CD83 binding protein comprising an antigen binding domain which specifically binds to CD83, wherein the binding protein comprises a heavy chain variable region ($V_H$) which comprises a sequence which is at least 90% identical to the amino acid sequence shown in SEQ ID NO:2. In one example, the heavy chain variable region ($V_H$) comprises a sequence which is at least 90% identical to the frame work regions of the amino acid sequence shown in SEQ ID NO:2.

The present disclosure additionally or alternatively provides a CD83 binding protein comprising an antigen binding domain which specifically binds to CD83, wherein the binding protein comprises a heavy chain variable region ($V_H$) which comprises three complementarity determining regions (CDRs) of the amino acid sequence shown in SEQ ID NO:2.

In one example, the $V_H$ CDR1 comprises amino acids 31 to 35 of SEQ ID NO:2, the $V_H$ CDR2 comprises amino acids 50 to 59 of SEQ ID NO:2 and the $V_H$ CDR3 comprises amino acids 99 to 106 of SEQ ID NO:2.

In one example, the $V_H$ CDR1 comprises the amino acid sequence shown in SEQ ID NO:3, the $V_H$ CDR2 comprises the amino acid sequence shown in SEQ ID NO:4 and the $V_H$ CDR3 comprises the amino acid sequence shown in SEQ ID NO:5.

The present disclosure additionally or alternatively provides a CD83 binding protein comprising an antigen binding domain which specifically binds to CD83, wherein the binding protein comprises a light chain variable region ($V_L$) which comprises:

(i) a sequence which is at least 90% identical to any one of the amino acid sequences shown in SEQ ID NOs:6 to 17; or (ii) three complementarity determining regions (CDRs) of any one of the amino acid sequences shown in SEQ ID NOs: 6 to 17; or (iii) a sequence as shown in SEQ ID NO:27 or SEQ ID NO:28 or SEQ ID NO:29; or (iv) three CDRs, wherein the amino acid sequence of CDR1, CDR2, or CDR3 is a consensus sequence shown in SEQ ID NOs:18 to 26.

In one example, the light chain variable region ($V_L$) comprises a sequence which is at least 90% identical to the frame work regions of any one of the amino acid sequences shown in SEQ ID NOs: 6 to 17.

In one example, the $V_L$ CDR1 comprises amino acids 24 to 34 of any one of SEQ ID NOs: 6 to 17; the $V_L$ CDR2 comprises amino acids 50 to 56 of any one of SEQ ID NOs: 6 to 17; and the $V_L$ CDR3 comprises amino acids 89 to 97 of any one of SEQ ID NOs: 6 to 17.

In one example, the $V_L$ CDR1 comprises the amino acid sequence shown in SEQ ID NO:18, the $V_L$ CDR2 comprises the amino acid sequence shown in SEQ ID NO:21 and the $V_L$ CDR3 comprises the amino acid sequence shown in SEQ ID NO:24.

In one example, the amino acid sequence of $V_L$ CDR1 comprises a Glutamine (Q) or Serine (S) or Arginine (R) at position 1 and/or Aspartic acid (D) or Serine (S) at position 3 and/or Serine (S) or Threonine (T) at position 4 and/or Serine (S) or Leucine (L) at position 5 and/or Alanine (A) or Asparagine (N) at position 6 and/or Glycine or no residue at position 8 and/or Threonine (T) or Asparagine (N) or Serine (S) or no residue at position 9 and/or Asparagine (N) or Tyrosine (Y) at position 10 and/or Valine (V) or Proline (P) or Threonine (T) or Tyrosine (Y) at position 11 and/or Valine (V) or Aspartic acid (D) at position 12 and/or Asparagine (N) or Phenylalanine (F) at position 13.

In one example, the amino acid sequence of $V_L$ CDR2 comprises a Serine (S) or Glycine (G) or Threonine (T) at position 1 and/or Asparagine (N) or Threonine (T) or Lysine (K) at position 2 and/or Isoleucine (I) or Aspartic Acid (D) or Asparagine (N) at position 3 and/or Asparagine (N) or Glutamine (Q) at position 4.

In one example, the amino acid sequence of $V_L$ CDR3 comprises a Alanine (A) or Asparagine (N) at position 1 and/or Serine (S) or Alanine (A) or Valine (V) at position 2 and/or Arginine (R) or Tryptophan (W) at position 3 and/or Serine (S) or Aspartic acid (D) or Glycine (G) at position 5 and/or Serine (S) or Glycine (G) at position 6 and/or Leucine (L) or no residue at position 7 and/or Glycine (G) or Serine (S) or Alanine (A) or Asparagine (N) at position 8 and/or Asparagine (N) or Glycine (G) at position 9 and/or Histidine (H) or Lysine (L) or Glycine (G) or no residue at position 10 and/or Tryptophan (W) or Tyrosine (Y) or Valine (V) at position 11 and/or Valine (V) or Isoleucine (I) at position 12.

In one example, the $V_L$ CDR1 comprises the amino acid sequence shown in SEQ ID NO:19, the $V_L$ CDR2 comprises the amino acid sequence shown in SEQ ID NO:22 and the $V_L$ CDR3 comprises the amino acid sequence shown in SEQ ID NO:25.

In one example, the amino acid sequence of $V_L$ CDR1 comprises a Lysine (K) or Arginine (R) at position 1 and/or Serine (S) or Asparagine (N) at position 3 and/or Valine (V) or Isoleucine (I) or Leucine (L) at position 7 and/or Aspartic Acid (D) or Histidine (H) at position 8 and/or Alanine (A) or Aspartic Acid (D) at position 10 and/or Asparagine (N) or Lysine (K) at position 12 and/or Methionine (M) or Threonine (T) at position 13 and/or Phenylalanine (F) or Tyrosine (Y) at position 14 and/or Aspartic Acid (D) or Histidine (H) or Asparagine (N) or Tyrosine (Y) at position 16.

In one example, the amino acid sequence of $V_L$ CDR2 comprises a Lysine (K) or Glutamic Acid (E) at position 1 and/or Aspartic Acid (D) or Phenylalanine (F) at position 6.

In one example, the amino acid sequence of $V_L$ CDR3 comprises Glycine (G) or Alanine (A) or Serine (S) at position 3 and/or Threonine (T) or Leucine (L) at position 4 and/or Glutamine (Q) or Histidine (H) at position 5 and/or Tryptophan (W) or Proline (P) or no residue at position 6 and/or Proline (P) or Threonine (T) or Leucine (L) at position 7 and/or Arginine (R) or Tryptophan (W) at position 8.

In one example, the $V_L$ CDR1 comprises the amino acid sequence shown in SEQ ID NO:20, the $V_L$ CDR2 comprises the amino acid sequence shown in SEQ ID NO:23 and the $V_L$ CDR3 comprises the amino acid sequence shown in SEQ ID NO:26.

In one example, the amino acid sequence of $V_L$ CDR1 comprises Arginine (R) or Glutamine (Q) at position 1 and/or Aspartic Acid (D) or Serine (S) at position 5 and/or Isoleucine (I) or Leucine (L) at position 6 and/or Serine (S) or Isoleucine (I) at position 7 and/or Asparagine (N) or Serine (S) at position 8.

In one example, the amino acid sequence of $V_L$ CDR2 comprises Aspartic Acid (D) or Alanine (A) at position 1 and/or Asparagine (N) or Isoleucine (I) at position 4 and/or Glutamic Acid (E) or Glutamine (Q) at position 6.

In one example, the amino acid sequence of $V_L$ CDR3 comprises Glutamine (Q) or Histidine (H) at position 2 and/or Aspartic Acid (D) or Tyrosine (Y) at position 4 and/or Phenylalanine (F) or Tryptophan (W) at position 6.

In one example, the $V_H$ and the $V_L$ are in a single polypeptide chain. For example, the CD83 binding protein is:
  (i) a single chain Fv fragment (scFv); or
  (ii) a dimeric scFv (di-scFv); or
  (iii) (i) or (ii) linked to a Fc or a heavy chain constant domain ($C_H$) 2 and/or $C_H$3; or
  (iv) (i) or (ii) linked to a protein that binds to an immune effector cell.

In another example, the $V_L$ and $V_H$ are in separate polypeptide chains. For example, the CD83 binding protein is:
  (i) a diabody; or
  (ii) a triabody; or
  (iii) a tetrabody; or
  (iv) a Fab; or
  (v) a F(ab')$_2$; or
  (vi) a Fv; or
  (vii) one of (i) to (vi) linked to a Fc or a $C_H$2 and/or $C_H$3; or
  (viii) one of (i) to (vi) linked to a protein that binds to an immune effector cell.

In one example, a CD83 binding protein of the disclosure comprises an antigen binding domain that competitively inhibits the binding of an antibody to CD83, the antibody comprising a heavy chain sequence as shown in SEQ ID NO:1 and a light chain sequence as shown in SEQ ID NO:31.

Exemplary CD83 binding proteins of the present disclosure comprise a $V_H$ of the disclosure and a chimeric, de-immunized, humanized, human, synhumanized or primatized light chain or $V_L$.

In an exemplary form of the present disclosure, the CD83 binding protein is an antibody. The antibody may comprise:
  (i) a $V_H$ sequence as shown in SEQ ID NO:2 and a $V_L$ sequence as shown in SEQ ID NO:6; or
  (ii) a $V_H$ sequence as shown in SEQ ID NO:2 and a $V_L$ sequence as shown in SEQ ID NO:7; or
  (iii) a $V_H$ sequence as shown in SEQ ID NO:2 and a $V_L$ sequence as shown in SEQ ID NO:8; or
  (iv) a $V_H$ sequence as shown in SEQ ID NO:2 and a $V_L$ sequence as shown in SEQ ID NO:9; or
  (v) a $V_H$ sequence as shown in SEQ ID NO:2 and a $V_L$ sequence as shown in SEQ ID NO:10; or (vi) a $V_H$ sequence as shown in SEQ ID NO:2 and a $V_L$ sequence as shown in SEQ ID NO:11; or (vii) a $V_H$ sequence as shown in SEQ ID NO:2 and a $V_L$ sequence as shown in SEQ ID NO:12; or (viii) a $V_H$ sequence as shown in SEQ ID NO:2 and a $V_L$ sequence as shown in SEQ ID NO:13; or (ix) a $V_H$ sequence as shown in SEQ ID NO:2 and a $V_L$ sequence as shown in SEQ ID NO:14; or (x) a $V_H$ sequence as shown in SEQ ID NO:2 and a $V_L$ sequence as shown in SEQ ID NO:15; or (xi) a $V_H$ sequence as shown in SEQ ID NO:2 and a $V_L$ sequence as shown in SEQ ID NO:16; or (xii) a $V_H$ sequence as shown in SEQ ID NO:2 and a $V_L$ sequence as shown in SEQ ID NO:17.

In one example, the antibody depletes cells to which it binds, for example, immune cells such as antigen presenting cells (APC) (e.g., dendritic cells (DCs)) and/or lymphocytes (e.g., T cells).

As will be apparent to the skilled artisan from the disclosure herein, exemplary CD83 binding proteins are capable of depleting cells to which they bind without being conjugated to a toxic compound.

In one example, the CD83 binding protein is capable of inducing an effector function, for example, an effector function that results in killing a cell to which antibody binds. Exemplary effector functions include ADCC, antibody-dependent cell-mediated phagocytosis (ADCP) and/or complement-dependent cytotoxicity (CDC).

In one example, the CD83 binding protein is capable of inducing ADCC.

In one example, the CD83 binding protein comprises an antibody Fc region capable of inducing an effector function. For example, the effector function is Fc-mediated effector function. In one example, the Fc region is an IgG1 Fc region.

In one example, the CD83 binding protein is capable of inducing a similar (e.g., not significantly different or within about 10%) or the same level of effector function as a wild-type human IgG1 region.

In one example, the CD83 binding protein is capable of inducing an enhanced level of effector function.

In one example, the level of effector function induced by the CD83 binding protein is enhanced relative to that of the CD83 binding protein when it comprises a wild-type IgG1 Fc region.

In one example, a CD83 binding protein of the present disclosure is a naked antibody or antigen binding fragment thereof.

In one example, a CD83 binding protein of the present disclosure is a full length antibody.

In one example, a CD83 binding protein of the present disclosure binds to CD83 with an equilibrium dissociation constant ($K_D$) of $5\times10^{-7}$ M or less, such as $4.5\times10^{-7}$ M or less, such as $4\times10^{-7}$ M or less, such as $3.5\times10^{-7}$ M or less, such as $3\times10^{-7}$ M or less, such as $2.5\times10^{-7}$ M or less, such as $2\times10^{-7}$ M or less, such as $1.5\times10^{-7}$ M or less, such as $1\times10^{-7}$ M or less, such as $9.5\times10^{-8}$ M or less, such as $9\times10^{-8}$ M or less, such as $8.5\times10^{-8}$ M or less, such as $8\times10^{-8}$ M or less, such as $7.5\times10^{-8}$ M or less, such as $7\times10^{-8}$ M or less, such as $6.5\times10^{-8}$ M or less, such as $6\times10^{-8}$ M or less, $5.5\times10^{-8}$ M or less, such as $5\times10^{-8}$ M or less, such as $4.5\times10^{-8}$ M or less, such as $4\times10^{-8}$ M or less, such as $3.5\times10^{-8}$ M or less, such as $3\times10^{-8}$ M or less, such as $2.5\times10^{-8}$ M or less, such as $2\times10^{-8}$ M or less, such as $1.5\times10^{-8}$ M or less, such as $1\times10^{-8}$ M or less, such as $9.5\times10^{-9}$ M or less, such as $9\times10^{-9}$ M or less, such as $8.5\times10^{-9}$ M or less, such as $8\times10^{-9}$ M or less, such as $7.5\times10^{-9}$ M or less, such as $7\times10^{-9}$ M or less, such as $6.5\times10^{-9}$ M or less, such as $6\times10^{-9}$ M or less, such as $5.5\times10^{-9}$ M or less, such as $5\times10^{-9}$ M.

In one example, a CD83 binding protein of the present disclosure binds to CD83 with a $K_D$ of between about $5.5\times10^{-8}$ M to about $5\times10^{-8}$ M, for example, $5.1\times10^{-8}$ M. In one example, the $K_D$ is between about $3\times10^{-8}$ M and about $2\times10^{-8}$ M, for example, is about $2.6\times10^{-8}$ M. In one example, the $K_D$ is between about $1.5\times10^{-8}$ M and about $9.5\times10^{-9}$ M, for example, is about $1\times10^{-9}$ M.

In one example, a CD83 binding protein of the present disclosure binds to CD83 with an on rate ($K_A$) of $5\times10^{6}$ M$^{-1}$ s$^{-1}$ or less, such as $4.5\times10^{6}$ M$^{-1}$ s$^{-1}$ or less, such as $4\times10^{6}$ M$^{-1}$ s$^{-1}$ or less, such as $3.5\times10^{6}$ M$^{-1}$ s$^{-1}$ or less, such as $3\times10^{6}$ M$^{-1}$ s$^{-1}$ or less, such as $2.5\times10^{6}$ M$^{-1}$ s$^{-1}$ or less, such as $2\times10^{6}$ M$^{-1}$ s$^{-1}$ or less, such as $1.5\times10^{6}$ M$^{-1}$ s$^{-1}$ or less, such as $1\times10^{6}$ M$^{-1}$ s$^{-1}$ or less, such as $9.5\times10^{5}$ M$^{-1}$ s$^{-1}$ or less, such as $9\times10^{5}$ M$^{-1}$ s$^{-1}$ or less, such as $8.5\times10^{5}$ M$^{-1}$ s$^{-1}$ or less, such as $8\times10^{5}$ M$^{-1}$ s$^{-1}$ or less, such as $7.5\times10^{5}$ M$^{-1}$ s$^{-1}$ or less, such as $7\times10^{5}$ M$^{-1}$ s$^{-1}$ or less, such as $6.5\times10^{5}$ M$^{-1}$ s$^{-1}$ or less, such as $6\times10^{5}$ M$^{-1}$ s$^{-1}$ or less, such as $5.5\times10^{5}$ M$^{-1}$ s$^{-1}$ or less, such as $5\times10^{5}$ M$^{-1}$ s$^{-1}$ or less, such as $4.5\times10^{5}$ M$^{-1}$ s$^{-1}$ or less, such as $4\times10^{5}$ M$^{-1}$ s$^{-1}$ or less, such as $3.5\times10^{5}$ M$^{-1}$ s$^{-1}$ or less, such as $3\times10^{5}$ M$^{-1}$ s$^{-1}$ or less, such as $2.5\times10^{5}$ M$^{-1}$ s$^{-1}$ or less, such as $2\times10^{5}$ M$^{-1}$ s$^{-1}$ or less, such as $1.5\times10^{5}$ M$^{-1}$ s$^{-1}$ or less, such as $1\times10^{5}$ M$^{-1}$ s$^{-1}$.

In one example, a CD83 binding protein of the present disclosure binds to CD83 with a $K_A$ of about $3\times10^{5}$ M$^{-1}$ s$^{-1}$ or less. In one example, the $K_A$ is between about $1.5\times10^{5}$ M$^{-1}$ s$^{-1}$ and about $2\times10^{5}$ M$^{-1}$ s$^{-1}$, for example, is about $1.8\times10^{5}$ M$^{-1}$ s$^{-1}$. In one example, the $K_A$ is between about $2\times10^{5}$ M$^{-1}$ s$^{-1}$ and about $3\times10^{5}$ M$^{-1}$ s$^{-1}$, for example, is about $2.6\times10^{5}$ M$^{-1}$ s$^{-1}$.

In one example, a CD83 binding protein of the present disclosure dissociates from CD83 with an off rate of ($K_{off}$) of $5\times10^{-2}$ s$^{-1}$ or less, such as $4.5\times10^{-2}$ s$^{-1}$ or less, such as $4\times10^{-2}$ s$^{-1}$ or less, such as $3.5\times10^{-2}$ s$^{-1}$ or less, such as $3\times10^{-2}$ s$^{-1}$ or less, such as $2.5\times10^{-2}$ s$^{-1}$ or less, such as $2\times10^{-2}$ s$^{-1}$ or less, such as $1.5\times10^{-2}$ s$^{-1}$ or less, such as $1\times10^{-2}$ s$^{-1}$ or less, such as $9.5\times10^{-3}$ s$^{-1}$ or less, such as $9\times10^{-3}$ s$^{-1}$ or less, such as $8.5\times10^{-3}$ s$^{-1}$ or less, such as $8\times10^{-3}$ s$^{-1}$ or less, such as $7.5\times10^{-3}$ s$^{-1}$ or less, such as $7\times10^{-3}$ s$^{-1}$ or less, such as $6.5\times10^{-3}$ s$^{-1}$ or less, such as $6\times10^{-3}$ s$^{-1}$ or less, such as $5.5\times10^{-3}$ s$^{-1}$ or less, such as $5\times10^{-3}$ s$^{-1}$ or less, such as $4.5\times10^{-3}$ s$^{-1}$ or less, such as $4\times10^{-3}$ s$^{-1}$ or less, such as $3.5\times10^{-3}$ s$^{-1}$ or less, such as $3\times10^{-3}$ s$^{-1}$ or less, such as $2.5\times10^{-3}$ s$^{-1}$ or less, such as $2\times10^{-3}$ s$^{-1}$ or less, such as $1.5\times10^{-3}$ s$^{-1}$ or less, such as $1\times10^{-3}$ s$^{-1}$ or less, such as $9.5\times10^{-4}$ s$^{-1}$ or less, such as $9\times10^{-4}$ s$^{-1}$ or less, such as $8.5\times10^{-4}$ s$^{-1}$ or less, such as $8\times10^{-4}$ s$^{-1}$ or less.

In one example, a CD83 binding protein of the present disclosure dissociates from CD83 with a $K_{off}$ of about $8\times10^{-3}$ s$^{-1}$ or less. In one example, the $K_{off}$ is between about $6\times10^{-3}$ s$^{-1}$ and about $7\times10^{-3}$ s$^{-1}$, for example, is about $6.4\times10^{-3}$ s$^{-1}$. In one example, the $K_{off}$ is between about $1\times10^{-3}$ s$^{-1}$ and about $2\times10^{-3}$ s$^{-1}$, for example, is about $1.7\times10^{-3}$ s$^{-1}$.

The disclosure also includes fragments, variants and derivatives of the antibody of the disclosure.

In one example, the disclosure provides a pharmaceutical composition comprising a CD83 binding protein according to the present disclosure and a suitable carrier, for example, a pharmaceutically acceptable carrier, diluent or excipient.

The present disclosure also provides an isolated or recombinant nucleic acid encoding a CD83 binding protein of the present disclosure.

Exemplary sequences of nucleic acids are discussed in the context of encoding CD83 binding proteins of the disclosure and are to be taken to apply mutatis mutandis to the present example of the disclosure.

In one example, the nucleic acid of the disclosure comprises a nucleotide sequence as shown in any one of SEQ ID NOs: 30 or 32 to 43.

The present disclosure also provides a nucleic acid capable of hybridizing to a nucleic acid of the disclosure under moderate or high stringency hybridization conditions.

The disclosure also includes fragments, homologs and derivatives of an isolated nucleic acid of the disclosure.

The present disclosure also provides a genetic construct comprising an isolated or recombinant nucleic acid of the disclosure and one or more additional nucleotide sequences, such as a promoter operably linked to the nucleic acid.

In one example, the genetic construct is an expression construct comprising an expression vector and an isolated or recombinant nucleic acid of the disclosure, wherein said isolated or recombinant nucleic acid is operably linked to one or more regulatory nucleic acids in said expression vector.

In one example, the genetic construct of the disclosure comprises a nucleic acid encoding a polypeptide (e.g., comprising a $V_H$) operably linked to a promoter and a nucleic acid encoding another polypeptide (e.g., comprising a $V_L$) operably linked to a promoter.

In another example, the genetic construct is a bicistronic genetic construct, for example, comprising the following operably linked components in 5' to 3' order:
  (i) a promoter;
  (ii) a nucleic acid encoding a first polypeptide;
  (iii) an internal ribosome entry site; and
  (iv) a nucleic acid encoding a second polypeptide.

For example, the first polypeptide comprises a $V_H$ and the second polypeptide comprises a $V_L$, or the first polypeptide comprises a $V_L$ and the second polypeptide comprises a $V_H$.

The present disclosure also contemplates separate genetic constructs one of which encodes a first polypeptide (e.g., comprising a $V_H$) and another of which encodes a second polypeptide (e.g., comprising a $V_L$). For example, the present disclosure also provides a composition comprising:
  (i) a first genetic construct comprising a nucleic acid encoding a polypeptide (e.g., comprising a $V_H$) operably linked to a promoter; and
  (ii) a second genetic construct comprising a nucleic acid encoding a polypeptide (e.g., comprising a $V_L$) operably linked to a promoter.

The disclosure also provides a cell comprising a genetic construct according to the present disclosure.

In one example, the present disclosure provides an isolated cell expressing a CD83 binding protein of the disclosure or a recombinant cell genetically-modified to express the CD83 binding protein of the invention.

In one example, the cell comprises the genetic construct of the disclosure or:
  (i) a first genetic construct comprising a nucleic acid encoding a polypeptide (e.g., comprising a $V_H$) operably linked to a promoter; and
  (ii) a second genetic construct comprising a nucleic acid encoding a polypeptide (e.g., comprising a $V_L$) operably linked to a promoter,
wherein the first and second polypeptides form an antibody or an antigen binding fragment of the present disclosure.

The genetic construct can be integrated into the cell or remain episomal.

Examples of cells of the present disclosure include bacterial cells, yeast cells, insect cells or mammalian cells.

The present disclosure additionally provides a method for producing a CD83 binding protein of the disclosure, the method comprising maintaining the genetic construct(s) of the disclosure under conditions sufficient for the CD83 binding protein to be produced.

In one example, the method for producing a CD83 binding protein of the disclosure comprises culturing the cell of the disclosure under conditions sufficient for the CD83 binding protein to be produced and, optionally, secreted.

In one example, the method for producing a CD83 binding protein of the disclosure additionally comprises isolating the CD83 binding protein.

The present disclosure additionally provides a method of producing a recombinant a CD83 binding protein, the method including the steps of:
  (i) culturing a cell containing an expression vector according to the disclosure such that the recombinant immunoglobulin or antibody is expressed in said host cell; and
  (ii) isolating the recombinant CD83 binding protein.

In one example, a method for producing a CD83 binding protein of the disclosure additionally comprises formulating the CD83 binding protein with a pharmaceutically acceptable carrier.

The present disclosure also provides a method of therapeutic or prophylactic treatment of a disease or condition in a subject, the method including the step of administering the CD83 binding protein of the disclosure to the subject to thereby treat or prevent the disease or condition.

In one example, the subject is a mammal.

In one example, the mammal is a human.

In one example, the mammal is in need of treatment or prophylaxis.

In one example, the mammal in need suffers from the disease or condition.

In one example, the mammal in need is at risk of developing the disease or condition or a relapse thereof.

The present disclosure also provides for use of a CD83 binding protein of the disclosure or a composition of the disclosure in medicine.

The present disclosure additionally or alternatively provides for use of a CD83 binding protein of the disclosure in the manufacture of a medicament for the treatment of a disease or condition in a subject.

The present disclosure also provides a CD83 binding protein of the disclosure for use in the treatment of a disease or condition in a subject.

In one example, the disease or condition is a CD83 mediated disease or condition.

In one example, the disease or condition is an autoimmune disease or condition, or an inflammatory disease or condition. For example, the disease or condition is mysthemia gravis, multiple sclerosis, vasculitis, chronic inflammatory bowel diseases such as Morbus Crohn or colitis ulcerosa, HLA B27-associated autoimmune disorders such as Morbus Bechterew, and systemic lupus erythematosis, skin diseases such as psoriasis, rheumatoid arthritis, and insulin-dependent diabetes mellitus in a subject.

In one example, the condition is graft versus host disease.

In one example, the disease or condition is caused by the dysfunction or undesired function of the immune system or a cellular response involving antigen presenting cells (APC) (e.g., dendritic cells (DCs)) and/or lymphocytes (e.g., T cells) in a subject, the method comprising administering a CD83 binding protein or composition of the disclosure to the subject.

In another example, the disease or condition is rejection of a cell, tissue or organ graft.

In another example, the disease or condition is rejection of a stem cell graft, for example, an hematopoietic stem cell transplantation (HSCT) or an umbilical cord blood transplantation (UCBT) or an endothelial progenitor cell transplant. For example, rejection of the stem cell transplant occurs as a result of graft versus host disease or host versus graft disease. The HSCT may be derived from, for example, the bone marrow directly or from the peripheral blood following mobilization of cells from the bone marrow (e.g. by administration of G-CSF) or directly from donor umbilical cord blood.

In one example, the method comprises administering an effective amount of the CD83 binding protein, such as a therapeutically effective amount of the CD83 binding protein to the donor and/or recipient. The graft may be contacted with an effective amount of the CD83 binding protein ex vivo or in vivo prior to or after being transplanted.

The present disclosure also provides a method for downregulating the immunoactivity of an allogeneic graft, the method comprising contacting the graft with a CD83 binding protein or a composition of the disclosure.

In one example, the allogeneic graft is a hematopoietic stem cell graft.

In one example, the graft is contacted with a CD83 binding protein or a composition of the disclosure ex vivo.

In another or additional example, the recipient of the graft is administered a CD83 binding protein or a composition of the disclosure prior to and/or simultaneously with and/or following transplant of the graft.

BRIEF DESCRIPTION OF THE DRAWINGS

FIG. 2 is a graphical representation of the reactivity and specificity of purified hFab clone 1F7. A. Purified 1F7 bound specifically in a dose dependant manner to CD83-His, detected with anti-kappa-HRP antibody. B. 1F7 binds specifically to hCD83 ectodomain (Fc and His tagged) and does not recognise mouse CD83 and does react non-specifically to 5 other antigens analysed.

FIG. 3 is a graphical representation of the cell surface binding specificity of 1F7 hFab to KMH2 cells expressing CD83. A. 1F7 Fab pre-mixed with anti-human F(ab')2 resulted a shift in fluorescence to the right analysed by FACS. Addition of mCD83 and hCD83-His and hCD83-Fc blocked fluorescence by 95%. B. Titration of hFab 1F7 (100, 25, 5, 1 μg/ml) with a 2:1 molar ratio of anti-human F(ab')2 showed a high level of fluorescence indicating binding of hFab to cell-surface CD83, which reduced in a dose-dependent manner.

FIG. 4 is a graphical representation of the protein sequences of $V_L$ chain shuffled clones after 4 rounds of stringent selection on CD83-His antigen. The differences in CDRs and framework regions 2 and 3 of the clones are show in bold font.

SEQUENCE LISTING

Figure 1:
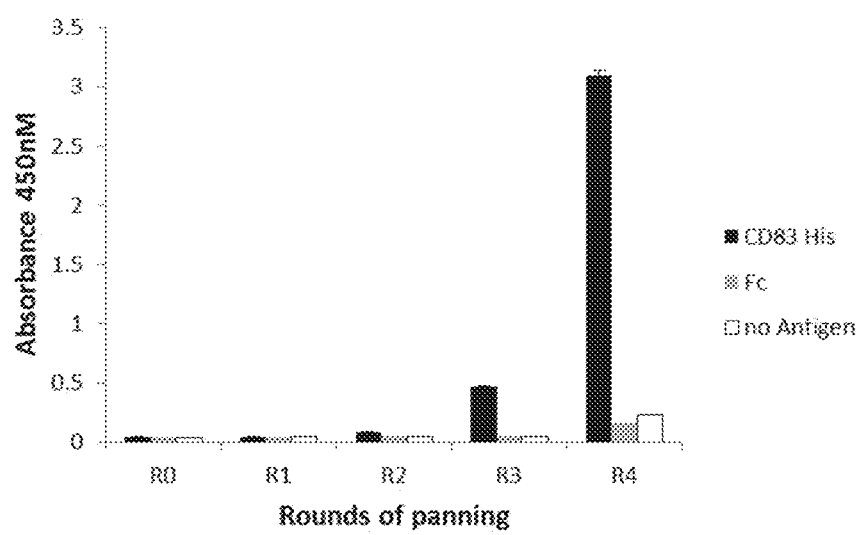
FIG. 1 is a graphical representation of the high reactivity of hFab's from the phage display library to recombinant CD83-His as analysed by ELISA. Analysis was performed in duplicate; error bars represent ranges of individual values. The control antigen is an irrelevant antigen of the Fc portion of human IgG.

SEQ ID NO: 1 amino acid sequence of IF7 heavy chain
SEQ ID NO: 2 heavy chain $V_H$ amino acid sequence
SEQ ID NO: 3 heavy chain $V_H$ CDR1 amino acid sequence
SEQ ID NO: 4 heavy chain $V_H$ CDR2 amino acid sequence
SEQ ID NO: 5 heavy chain $V_H$ CDR3 amino acid sequence
SEQ ID NO: 6 light chain $V_L$ amino acid sequence of IF7
SEQ ID NO: 7 light chain $V_L$ amino acid sequence of hFab4.1
SEQ ID NO: 8 light chain $V_L$ amino acid sequence of hFab4.2
SEQ ID NO: 9 light chain $V_L$ amino acid sequence of hFab4.3
SEQ ID NO: 10 light chain $V_L$ amino acid sequence of hFab4.4
SEQ ID NO: 11 light chain $V_L$ amino acid sequence of hFab4.5
SEQ ID NO: 12 light chain $V_L$ amino acid sequence of hFab4.7
SEQ ID NO: 13 light chain $V_L$ amino acid sequence of hFab4.8
SEQ ID NO: 14 light chain $V_L$ amino acid sequence of hFab4.9
SEQ ID NO: 15 light chain $V_L$ amino acid sequence of hFab4.10
SEQ ID NO: 16 light chain $V_L$ amino acid sequence of hFab4.12
SEQ ID NO: 17 light chain $V_L$ amino acid sequence of hFab4.18
SEQ ID NO: 18 light chain $V_L$ CDR1 amino acid consensus sequence of IF7, hFab4.1, hFab4.10 and hFab4.12
SEQ ID NO: 19 light chain $V_L$ CDR1 amino acid consensus sequence of hFab4.2; hFab4.3; hFab4.4; hFab4.5; hFab4.6; hFab4.7 and hFab4.18
SEQ ID NO: 20 light chain $V_L$ CDR1 amino acid consensus sequence of hFab4.8 and hFab4.9
SEQ ID NO: 21 light chain $V_L$ CDR2 amino acid consensus sequence of IF7, hFab4.1, hFab4.10 and hFab4.12
SEQ ID NO: 22 light chain $V_L$ CDR2 amino acid consensus sequence of hFab4.2; hFab4.3; hFab4.4; hFab4.5; hFab4.6; hFab4.7 and hFab4.18
SEQ ID NO: 23 light chain $V_L$ CDR2 amino acid consensus sequence of hFab4.8 and hFab4.9
SEQ ID NO: 24 light chain $V_L$ CDR3 amino acid consensus sequence of IF7, hFab4.1, hFab4.10 and hFab4.12
SEQ ID NO: 25 light chain $V_L$ CDR3 amino acid consensus sequence of hFab4.2; hFab4.3; hFab4.4; hFab4.5; hFab4.6; hFab4.7 and hFab4.18
SEQ ID NO: 26 light chain $V_L$ CDR3 amino acid consensus sequence of hFab4.8 and hFab4.9
SEQ ID NO: 27 $V_L$ amino acid consensus sequence of IF7, hFab4.1, hFab4.10 and hFab4.12
SEQ ID NO: 28 $V_L$ amino acid consensus sequence of hFab4.2; hFab4.3; hFab4.4; hFab4.5; hFab4.6; hFab4.7 and hFab4.18
SEQ ID NO: 29 $V_L$ amino acid consensus sequence of hFab4.8 and hFab4.9
SEQ ID NO: 30 heavy chain VH nucleotide sequence
SEQ ID NO: 31 amino acid sequence of IF7 light chain
SEQ ID NO: 32 nucleotide sequence of IF7 light chain
SEQ ID NO: 33 nucleotide sequence of hFab4.1 light chain
SEQ ID NO: 34 nucleotide sequence of hFab4.2 light chain
SEQ ID NO: 35 nucleotide sequence of hFab4.3 light chain SEQ ID NO: 36 nucleotide sequence of hFab4.4 light chain
SEQ ID NO: 37 nucleotide sequence of hFab4.5 light chain
SEQ ID NO: 38 nucleotide sequence of hFab4.7 light chain
SEQ ID NO: 39 nucleotide sequence of hFab4.8 light chain
SEQ ID NO: 40 nucleotide sequence of hFab4.9 light chain
SEQ ID NO: 41 nucleotide sequence of hFab4.10 light chain
SEQ ID NO: 42 nucleotide sequence of hFab4.12 light chain
SEQ ID NO: 43 nucleotide sequence of hFab4.18 light chain
SEQ ID NO: 44 amino acid sequence of human CD83 isoform a
SEQ ID NO: 45 amino acid sequence of human CD83 isoform b
SEQ ID NO: 46 amino acid sequence of human CD83 isoform c
SEQ ID NO: 47 nucleotide sequence of pFUSE $V_H$ 4.4 For primer
SEQ ID NO: 48 nucleotide sequence of pFUSE $V_H$ 4.4 Rev primer
SEQ ID NO: 49 nucleotide sequence of pFUSE $V_L$ 4.4 For primer
SEQ ID NO: 50 nucleotide sequence of pFUSE $V_L$ 4.4 Rev primer
SEQ ID NO: 51 light chain $V_L$ CDR1 amino acid sequence of IF7
SEQ ID NO: 52 light chain $V_L$ CDR2 amino acid sequence of IF7
SEQ ID NO: 53 light chain $V_L$ CDR3 amino acid sequence of IF7
SEQ ID NO: 54 light chain $V_L$ CDR1 amino acid sequence of hFab4.1
SEQ ID NO: 55 light chain $V_L$ CDR2 amino acid sequence of hFab4.1
SEQ ID NO: 56 light chain $V_L$ CDR3 amino acid sequence of hFab4.1
SEQ ID NO: 57 light chain $V_L$ CDR1 amino acid sequence of hFab4.2
SEQ ID NO: 58 light chain $V_L$ CDR2 amino acid sequence of hFab4.2
SEQ ID NO: 59 light chain $V_L$ CDR3 amino acid sequence of hFab4.2
SEQ ID NO: 60 light chain $V_L$ CDR1 amino acid sequence of hFab4.3
SEQ ID NO: 61 light chain $V_L$ CDR2 amino acid sequence of hFab4.3
SEQ ID NO: 62 light chain $V_L$ CDR3 amino acid sequence of hFab4.3
SEQ ID NO: 63 light chain $V_L$ CDR1 amino acid sequence of hFab4.4
SEQ ID NO: 64 light chain $V_L$ CDR2 amino acid sequence of hFab4.4
SEQ ID NO: 65 light chain $V_L$ CDR3 amino acid sequence of hFab4.4
SEQ ID NO: 66 light chain $V_L$ CDR1 amino acid sequence of hFab4.5
SEQ ID NO: 67 light chain $V_L$ CDR2 amino acid sequence of hFab4.5
SEQ ID NO: 68 light chain $V_L$ CDR3 amino acid sequence of hFab4.5
SEQ ID NO: 69 light chain $V_L$ CDR1 amino acid sequence of hFab4.7
SEQ ID NO: 70 light chain $V_L$ CDR2 amino acid sequence of hFab4.7
SEQ ID NO: 71 light chain $V_L$ CDR3 amino acid sequence of hFab4.7
SEQ ID NO: 72 light chain $V_L$ CDR1 amino acid sequence of hFab4.8
SEQ ID NO: 73 light chain $V_L$ CDR2 amino acid sequence of hFab4.8
SEQ ID NO: 74 light chain $V_L$ CDR3 amino acid sequence of hFab4.8
SEQ ID NO: 75 light chain $V_L$ CDR1 amino acid sequence of hFab4.9
SEQ ID NO: 76 light chain $V_L$ CDR2 amino acid sequence of hFab4.9
SEQ ID NO: 77 light chain $V_L$ CDR3 amino acid sequence of hFab4.9
SEQ ID NO: 78 light chain $V_L$ CDR1 amino acid sequence of hFab4.10
SEQ ID NO: 79 light chain $V_L$ CDR2 amino acid sequence of hFab4.10
SEQ ID NO: 80 light chain $V_L$ CDR3 amino acid sequence of hFab4.10
SEQ ID NO: 81 light chain $V_L$ CDR1 amino acid sequence of hFab4.12
SEQ ID NO: 82 light chain $V_L$ CDR2 amino acid sequence of hFab4.12
SEQ ID NO: 83 light chain $V_L$ CDR3 amino acid sequence of hFab4.12
SEQ ID NO: 84 light chain $V_L$ CDR1 amino acid sequence of hFab4.18
SEQ ID NO: 85 light chain $V_L$ CDR2 amino acid sequence of hFab4.18
SEQ ID NO: 86 light chain $V_L$ CDR3 amino acid sequence of hFab4.18

DETAILED DESCRIPTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Each example of the present disclosure described herein is to be applied mutatis mutandis to each and every other example unless specifically stated otherwise.

Those skilled in the art will appreciate that the disclosure herein is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the disclosure, as described herein.

The present disclosure is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in Sambrook, Fritsch & Maniatis, Molecular Cloning: A Laboratory Manual, Cold Spring Harbor Laboratories, New York, Second Edition (1989), whole of Vols I, II, and III; Benny K. C. Lo, Antibody Engineering: Methods and Protocols, (2004) Humana Press, Vol. 248; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, pp 1-22; Atkinson et al., pp 35-81; Sproat et al., pp 83-115; and Wu et al., pp 135-151; Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series; J. F. Ramalho Ortigao, "The Chemistry of Peptide Synthesis" In: Knowledge database of Access to Virtual Laboratory website (Interactiva, Germany); Sakakibara Biochem. Biophys. Res. Commun. 73: 336-342, 1976; Merrifield J. Am. Chem. Soc. 85: 2149-2154, 1963; Barany and Merrifield (1979) in The Peptides (Gross, E. and Meienhofer, J. eds.), vol. 2, pp. 1-284, Academic Press, New York. 12. Wunsch, E., ed. (1974) Synthese von Peptiden in Houben-Weyls Metoden der Organischen Chemie (Miller, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky Int. J. Peptide Protein Res. 25: 449-474, 1985; Handbook of Experimental Immunology, Vols. I-IV (D. M. Weir and C. C. Blackwell, eds., 1986, Blackwell Scientific Publications); and Animal Cell Culture: Practical Approach, 3rd edn (John R. W. Masters, ed., 2000), ISBN 0199637970, whole of text.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Selected Definitions

CD83 is a single-pass type I membrane protein and member of the immunoglobulin superfamily. Three human transcript variants encoding different isoforms have been found. For the purposes of nomenclature and not limitation, the amino acid sequences of the human CD83 (hCD83) isoforms are shown in SEQ ID NO:44 (NP_004224.1; isoform a), SEQ ID NO:45 (NP_001035370.1; isoform b) and SEQ ID NO:46 (NP_001238830.1; isoform c). Accordingly, in one example, the amino acid sequence of human CD83 comprises an amino acid sequence as shown in SEQ ID NO:44, 45, or 46. Homologs of CD83 can be found in Pan troglodytes (XP_518248.2), *Macaca mulatta* (XP_001093591.1), *Canis lupus familiaris* (XP_852647.1), *Bos Taurus* (NP_001040055.1), *Mus musculus* (NP_033986.1), *Rattus norvegicus* (NP_001101880.1) and *Gallus gallus* (XP_418929.1). Exemplary CD83 binding proteins of the disclosure bind to or bind specifically to hCD83, including recombinant forms thereof (rhCD83).

The term "isolated protein" or "isolated polypeptide" is intended to mean a protein or polypeptide that by virtue of its origin or source of derivation is not associated with naturally-associated components that accompany it in its native state; is substantially free of other proteins from the same source. A protein may be rendered substantially free of naturally associated components or substantially purified by isolation, using protein purification techniques known in the art. By "substantially purified" is meant the protein is substantially free of contaminating agents, for example, at least about 70% or 75% or 80% or 85% or 90% or 95% or 96% or 97% or 98% or 99% free of contaminating agents.

The term "recombinant" shall be understood to mean the product of artificial genetic recombination. Accordingly, in the context of a recombinant protein comprising an antigen binding domain, this term does not encompass an antibody naturally-occurring within a subject's body that is the product of natural recombination that occurs during B cell maturation. However, if such an antibody is isolated, it is to be considered an isolated protein comprising an antigen binding domain. Similarly, if nucleic acid encoding the protein is isolated and expressed using recombinant means, the resulting protein is a recombinant protein comprising an antigen binding domain. A recombinant protein also encompasses a protein expressed by artificial recombinant means when it is within a cell, tissue or subject, for example, in which it is expressed.

The term "CD83 binding protein" shall be taken to include a single polypeptide chain (i.e., a series of contiguous amino acids linked by peptide bonds), or a series of polypeptide chains covalently or non-covalently linked to one another (i.e., a polypeptide complex or protein) capable of binding to CD83 in the manner described and/or claimed herein. For example, the series of polypeptide chains can be covalently linked using a suitable chemical or a disulphide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

As used herein, the term "antigen binding domain" shall be taken to mean a region of an antibody that is capable of specifically binding to an antigen, that is, a $V_H$ or a $V_L$ or an Fv comprising both a $V_H$ and a $V_L$. The antigen binding domain need not be in the context of an entire antibody, for example, it can be in isolation (e.g., a domain antibody) or in another form (e.g., scFv).

For the purposes for the present disclosure, the term "antibody" includes a protein capable of specifically binding to one or a few closely related antigens (e.g., CD83) by virtue of an antigen binding domain contained within a Fv. This term includes four chain antibodies (e.g., two light (L) chains and two heavy (H) chains), recombinant or modified antibodies (e.g., chimeric antibodies, humanized antibodies, human antibodies, CDR-grafted antibodies, primatized antibodies, de-immunized antibodies, synhumanized antibodies, half-antibodies, bispecific antibodies). An antibody generally comprises constant domains, which can be arranged into a constant region or constant fragment or fragment crystallizable (Fc). Exemplary forms of antibodies comprise a four-chain structure as their basic unit. Full-length antibodies comprise two heavy chains (~50 to 70 kDa each) covalently linked and two light chains (~23 kDa each). A light chain generally comprises a variable region (if present) and a constant domain and in mammals is either a κ light chain or a λ light chain. A heavy chain generally comprises a variable region and one or two constant domain(s) linked by a hinge region to additional constant domain(s). Heavy chains of mammals are of one of the following types α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies. Each chain has an N-terminal variable region ($V_H$ or $V_L$ wherein each are ~110 amino acids in length) and one or more constant domains at the C-terminus. The constant domain of the light chain (CL which is ~110 amino acids in length) is aligned with and disulfide bonded to the first constant domain of the heavy chain ($C_H1$ which is 330 to 440 amino acids in length). The light chain variable region is aligned with the variable region of the heavy chain. The antibody heavy chain can comprise 2 or more additional $C_H$ domains (such as, $C_H2$, $C_H3$ and the like) and can comprise a hinge region between the $C_H1$ and $C_H2$ constant domains. Antibodies can be of any type (e.g., IgG, IgE, IgM, IgD, IgA, and IgY), class (e.g., IgG1, IgG2, IgG3, IgG4, IgA1 and IgA2) or subclass. In one example, the antibody is a murine (mouse or rat) antibody or a primate (such as, human) antibody. In one example, the antibody is humanized, synhumanized, chimeric, CDR-grafted or deimmunized.

The term "naked antibody" refers to an antibody that is not conjugated to another compound, for example, a toxic compound or radiolabel.

As used herein, "variable region" refers to the portions of the light and/or heavy chains of an antibody as defined herein that is capable of specifically binding to an antigen and, includes amino acid sequences of complementarity determining regions (CDRs), that is, CDR1, CDR2, and CDR3, and framework regions (FRs). For example, the variable region comprises three or four FRs (e.g., FR1, FR2, FR3 and optionally FR4) together with three CDRs. $V_H$ refers to the variable region of the heavy chain. $V_L$ refers to the variable region of the light chain.

As used herein, the term "complementarity determining regions" (syn. CDRs, i.e., CDR1, CDR2, and CDR3) refers to the amino acid residues of an antibody variable region the presence of which are major contributors to specific antigen binding. Each variable region domain ($V_H$ or $V_L$) typically has three CDR regions identified as CDR1, CDR2 and CDR3. In one example, the amino acid positions assigned to CDRs and FRs are defined according to Kabat Sequences of Proteins of Immunological Interest, National Institutes of Health, Bethesda, Md., 1987 and 1991 (also referred to herein as "the Kabat numbering system"). In another example, the amino acid positions assigned to CDRs and FRs are defined according to the Enhanced Chothia Numbering Scheme (http://www.bioinfo.org.uk/mdex.html). According to the numbering system of Kabat, $V_H$ FRs and CDRs are positioned as follows: residues 1 to 30 (FR1), 31 to 35 (CDR1), 36 to 49 (FR2), 50 to 65 (CDR2), 66 to 94 (FR3), 95 to 102 (CDR3) and 103 to 113 (FR4). According to the numbering system of Kabat, $V_L$ FRs and CDRs are positioned as follows: residues 1 to 23 (FR1), 24 to 34 (CDR1), 35 to 49 (FR2), 50 to 56 (CDR2), 57 to 88 (FR3), 89 to 97 (CDR3) and 98 to 107 (FR4). The present disclosure is not limited to FRs and CDRs as defined by the Kabat numbering system, but includes all numbering systems, including the canonical numbering system or of Chothia and Lesk J. Mol. Biol. 196: 901-917, 1987; Chothia et al., Nature 342: 877-883, 1989; and/or Al-Lazikani et al., J. Mol. Biol. 273: 927-948, 1997; the numbering system of Honnegher and Plükthun J. Mol. Biol. 309: 657-670, 2001; or the IMGT system discussed in Giudicelli et al., Nucleic Acids Res. 25: 206-211 1997. In one example, the CDRs are defined according to the Kabat numbering system. Optionally, heavy chain CDR2 according to the Kabat numbering system does not comprise the five C-terminal amino acids listed herein or any one or more of those amino acids are substituted with another naturally-occurring amino acid. In an additional, or alternative, option, light chain CDR1 does not comprise the four N-terminal amino acids listed herein or any one or more of those amino acids are substituted with another naturally-occurring amino acid. In this regard, Padlan et al., FASEB J., 9: 133-139, 1995 established that the five C-terminal amino acids of heavy chain CDR2 and/or the four N-terminal amino acids of light chain CDR1 are not generally involved in antigen binding.

"Framework regions" (FRs) are those variable region residues other than the CDR residues.

As used herein, the term "Fv" shall be taken to mean any protein, whether comprised of multiple polypeptides or a single polypeptide, in which a $V_L$ and a $V_H$ associate and form a complex having an antigen binding domain that is capable of specifically binding to an antigen. The $V_H$ and the $V_L$ which form the antigen binding domain can be in a single polypeptide chain or in different polypeptide chains. Furthermore, a Fv of the disclosure (as well as any protein of the disclosure) may have multiple antigen binding domains which may or may not bind the same antigen. This term shall be understood to encompass fragments directly derived from an antibody as well as proteins corresponding to such a fragment produced using recombinant means. In some examples, the $V_H$ is not linked to a heavy chain constant domain ($C_H$) 1 and/or the $V_L$ is not linked to a light chain constant domain ($C_L$). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, for example, $C_H2$ or $C_H3$ domain, for example, a minibody.

A "Fab fragment" consists of a monovalent antigen-binding fragment of an immunoglobulin, and can be produced by digestion of a whole antibody with the enzyme papain, to yield a fragment consisting of an intact light chain and a portion of a heavy chain or can be produced using recombinant means.

A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means.

A "F(ab')$_2$ fragment" of an antibody consists of a dimer of two Fab' fragments held together by two disulfide bonds, and is obtained by treating a whole antibody molecule with the enzyme pepsin, without subsequent reduction.

A "Fab$_2$" fragment is a recombinant fragment comprising two Fab fragments linked using, for example, a leucine zipper or a $C_H3$ domain.

A "single chain Fv" or "scFv" is a recombinant molecule containing the variable region fragment (Fv) of an antibody in which the variable region of the light chain and the variable region of the heavy chain are covalently linked by a suitable, flexible polypeptide linker.

As used herein, the term "binds" in reference to the interaction of a CD83 binding protein or an antigen binding domain thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the antibody, will reduce the amount of labeled "A" bound to the antibody.

As used herein, the term "specifically binds" or "binds specifically" shall be taken to mean that a protein of the disclosure reacts or associates more frequently, more rapidly, with greater duration and/or with greater affinity with a particular antigen or cell expressing same than it does with alternative antigens or cells. For example, a protein that specifically binds to an antigen binds that antigen with greater affinity, avidity, more readily, and/or with greater duration than it binds to other antigens. For example, a protein binds to CD83 (e.g., hCD83) with materially greater affinity than it does to other immunoglobulin superfamily ligands or to antigens commonly recognized by polyreactive natural antibodies (i.e., by naturally occurring antibodies known to bind a variety of antigens naturally found in humans). It is also understood by reading this definition that, for example, a protein that specifically binds to a first antigen may or may not specifically bind to a second antigen. As such, "specific binding" does not necessarily require exclusive binding or non-detectable binding of another antigen, this is meant by the term "selective binding". In one example, "specific binding" of a CD83 binding protein of the disclosure to an antigen, means that the protein binds to the antigen with an equilibrium constant ($K_D$) of 100 nM or less, such as 50 nM or less, for example, 20 nM or less, such as, 15 nM or less or 10 nM or less or 5 nM or less or 1 nM or less or 500 pM or less or 400 pM or less or 300 pM or less or 200 pM or less or 100 pM or less.

As used herein, the term "epitope" (syn. "antigenic determinant") shall be understood to mean a region of CD83 to which a protein comprising an antigen binding domain of an antibody binds. This term is not necessarily limited to the specific residues or structure to which the protein makes contact. For example, this term includes the region spanning amino acids contacted by the protein and/or at least 5 to 10 or 2 to 5 or 1 to 3 amino acids outside of this region. In some examples, the epitope is a linear series amino acids. An epitope may also comprise a series of discontinuous amino acids that are positioned close to one another when CD83 is folded, that is, a "conformational epitope". The skilled artisan will also be aware that the term "epitope" is not limited to peptides or polypeptides. For example, the term "epitope" includes chemically active surface groupings of molecules such as sugar side chains, phosphoryl side chains, or sulfonyl side chains, and, in certain examples, may have specific three dimensional structural characteristics, and/or specific charge characteristics. An epitope or peptide or polypeptide comprising same can be administered to an animal to generate antibodies against the epitope.

The term "competitively inhibits" shall be understood to mean that a CD83 binding protein of the disclosure reduces or prevents binding of a recited antibody to CD83, for example, to hCD83. This may be due to the protein (or antigen binding domain) binding to the same or an overlapping epitope as the antibody. It will be apparent from the foregoing that the protein need not completely inhibit binding of the antibody, rather it need only reduce binding by a statistically significant amount, for example, by at least about 10% or 20% or 30% or 40% or 50% or 60% or 70% or 80% or 90% or 95%. Methods for determining competitive inhibition of binding are known in the art and/or described herein. For example, the antibody is exposed to CD83 either in the presence or absence of the protein. If less antibody binds in the presence of the protein than in the absence of the protein, the protein is considered to competitively inhibit binding of the antibody. In one example, the competitive inhibition of binding is caused by the antigen binding domain of the protein on CD83 overlapping with the antigen binding domain of the antibody.

"Overlapping" in the context of two epitopes means that two epitopes share a sufficient number of amino acid residues to permit a binding protein of the disclosure that binds to one epitope to competitively inhibit the binding of a recited antibody to CD83 that binds to the other epitope. For example, the "overlapping" epitopes share at least 1 or 2 or 3 or 4 or 5 or 6 or 7 or 8 or 9 or 10 or 11 or 12 or 13 or 14 or 15 or 16 or 17 or 18 or 19 or 20 amino acids.

As used herein, a "CD83 associated condition or disease" refers to any condition or disease that is caused by or associated with CD83 or a cell expressing CD83. The skilled artisan will be readily able to determine such conditions or diseases based on the disclosure herein and/or by performing an assay to diagnose a CD83 associated condition or disease. In this regard, in some examples the condition or disease is an inflammatory condition or disease, or an autoimmune condition or disease. A description of exemplary conditions and diseases is included herein.

As used herein, the terms "preventing", "prevent" or "prevention" include administering a protein of the disclosure to thereby stop or hinder the development of at least one symptom of a condition or disease. This term also encompasses treatment of a subject in remission to prevent or hinder relapse. For example, a subject suffering from relapsing-remitting multiple sclerosis is treated during remission to thereby prevent a relapse.

As used herein, the terms "treating", "treat" or "treatment" include administering a protein described herein to thereby reduce or eliminate at least one symptom of a specified condition or disease.

As used herein, the term "subject" shall be taken to mean any animal, such as, a mammal. In one example, the mammal is a human or non-human primate. In one example, the mammal is a human.

Reference herein to a "sample" should be understood as a reference to any sample derived from a subject such as, but not limited to, a body fluid (e.g., blood or blood fraction such as serum or plasma, tears, urine, synovial fluid or cerebrospinal fluid), cellular material (e.g. tissue aspirate), tissue biopsy specimens or surgical specimens. In some examples, the "sample" is any one or more of serum, plasma, PBMCs, or a buffy coat fraction.

As used herein, the term "diagnosis", and variants thereof such as, but not limited to, "diagnose", "diagnosed" or "diagnosing" includes any primary diagnosis of a clinical state or diagnosis of recurrent disease.

"Prognosis", "prognosing" and variants thereof as used herein refer to the likely outcome or course of a disease, including the chance of recovery or recurrence or the outcome of treatment.

The term "expression construct" is to be taken in its broadest context and includes a nucleic acid comprising one or more promoter sequences operably linked with one or more nucleic acids as described herein.

The term "expression vector" refers to a nucleic acid comprising an expression construct that is additionally capable of maintaining and or replicating nucleic acid in an expressible format. For example, an expression vector may comprise a plasmid, bacteriophage, phagemid, cosmid, virus sub-genomic or genomic fragment. Selection of appropriate vectors is within the knowledge of those having skill in the art.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, for example, in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter. A promoter can be operably linked to numerous nucleic acids, for example, through an internal ribosome entry site.

Proteins Comprising Antigen Binding Domains
Antibodies
Library-Based Methods

The present disclosure also encompasses screening of libraries of antibodies or proteins comprising antigen binding domains thereof (e.g., comprising variable regions thereof) to identify a CD83 binding protein of the disclosure. For example, a library comprising a $V_H$ of the disclosure and a plurality of $V_L$ regions can be screened to identify a CD83 binding protein of the disclosure.

Examples of libraries contemplated by this disclosure include naïve libraries (from unchallenged subjects), immunized libraries (from subjects immunized with an antigen) or synthetic libraries. Nucleic acid encoding antibodies or regions thereof (e.g., variable regions) are cloned by conventional techniques (e.g., as disclosed in Sambrook and Russell, eds, Molecular Cloning: A Laboratory Manual, 3rd Ed, vols. 1-3, Cold Spring Harbor Laboratory Press, 2001) and used to encode and display proteins using a method known in the art. Other techniques for producing libraries of proteins are described in, for example in U.S. Pat. No. 6,300,064 (e.g., a HuCAL library of Morphosys AG), U.S. Pat. Nos. 5,885,793, 6,204,023, 6,291,158, or U.S. Pat. No. 6,248,516.

The CD83 binding proteins according to the disclosure may be soluble secreted proteins or may be presented as a fusion protein on the surface of a cell, or particle (e.g., a phage or other virus, a ribosome or a spore). Various display library formats are known in the art. For example, the library is an in vitro display library (e.g., a ribosome display library, a covalent display library or a mRNA display library, e.g., as described in U.S. Pat. No. 7,270,969). In yet another example, the display library is a phage display library wherein proteins comprising antigen binding domains of antibodies are expressed on phage, for example, as described in U.S. Pat. Nos. 6,300,064, 5,885,793, 6,204,023, 6,291,158, or U.S. Pat. No. 6,248,516. Other phage display methods are known in the art and are contemplated by the present disclosure. Similarly, methods of cell display are contemplated by the disclosure, for example, bacterial display libraries, for example, as described in U.S. Pat. No. 5,516,637; yeast display libraries, for example, as described in U.S. Pat. No. 6,423,538; or a mammalian display library.

Methods for screening display libraries are known in the art. In one example, a display library of the present disclosure is screened using affinity purification, for example, as described in Scopes (In: Protein purification: principles and practice, Third Edition, Springer Verlag, 1994). Methods of affinity purification typically involve contacting proteins comprising antigen binding domains displayed by the library with a target antigen (e.g., CD83) and, following washing, eluting those domains that remain bound to the antigen.

Any variable regions or scFvs identified by screening are readily modified into a complete antibody, if desired. Exemplary methods for modifying or reformatting variable regions or scFvs into a complete antibody are described, for example, in Jones et al., J. Immunol. Methods 354: 85-90, 2010; or Jostock et al., J. Immunol. Methods, 289: 65-80, 2004. Alternatively, or additionally, standard cloning methods are used, e.g., as described in Ausubel et al., (In: Current Protocols in Molecular Biology. Wiley Interscience, ISBN 047 150338, 1987), and/or (Sambrook et al., (In: Molecular Cloning: Molecular Cloning: A Laboratory Manual, Cold Spring Harbor Laboratories, New York, Third Edition 2001).

In one example, the present disclosure provides a method of producing or isolating a CD83 binding protein of the disclosure by screening a display library, for example, a phage display library, for example, as described in U.S. Pat. No. 6,300,064 and/or U.S. Pat. No. 5,885,793. For example, the present inventors have isolated scFvs by biopanning a human scFv immunoglobulin gene library by three rounds of selection against recombinant extracellular domain of human CD83. Once isolated, a CD83 binding protein of the invention can be cloned and expressed and optionally reformatted as, for example, an IgG1 antibody using known methods in the art.

In one example, the present disclosure provides a method of producing a CD83 binding protein, the method comprising:

(i) screening a CD83 binding protein preparation or library for a binding protein that binds to the extracellular domain of CD83, for example, the extracellular domain of recombinant human CD83; and (ii) isolating a CD83 binding protein having a desired binding affinity for the extracellular domain of CD83.

In one example, a CD83 binding protein preparation is screened. A CD83 preparation may be made by, for example, immunizing an animal with a CD83 antigen so as to produce antibodies that react with the extracellular domain of CD83.

In another example, a CD83 binding protein library is screened. The library may be a phage library, for example, a Fab phage library.

In one example, the method comprises producing a population of phage particles displaying at their surface a population of binding molecules having a range of binding specificities for a target CD83 epitope or antigen. Such phage particles comprise a phagemid genome comprising a nucleic acid encoding the binding protein. This nucleic acid can be isolated, cloned and expressed in a recombinant system to produce the CD83 binding protein of the invention.

Deimmunized, Chimeric, Humanized, Synhumanized, Primatized, Human and Composite CD83 Binding Proteins The CD83 binding proteins of the present disclosure may be CDR grafted proteins which include CDRs from an antibody from a non-human species (e.g., mouse or rat or non-human primate) grafted onto or inserted into FRs from a human antibody or which include CDRs from an antibody from one type of antibody (e.g., one type of human antibody) grafted onto or inserted into FRs from another type of antibody (e.g., another type of human antibody). This term also encompasses a composite protein comprising, for example, one or more CDR grafted variable regions and one or more, for example, human variable regions, chimeric variable regions, synhumanized variable regions, or primatized variable regions.

The CD83 binding proteins of the present disclosure may be humanized proteins.

The term "humanized protein" shall be understood to refer to a protein comprising a human-like variable region, which includes CDRs from an antibody from a human species (e.g., mouse or rat or non-human primate) grafted onto or inserted into FRs from a non-human antibody (this type of antibody is also referred to as a "CDR-grafted antibody"). Humanized proteins also include proteins in which one or more residues of the human protein are modified by one or more amino acid substitutions and/or one or more FR residues of the human protein are replaced by corresponding non-human residues. Humanized proteins may also comprise residues which are found in neither the human antibody or in the non-human antibody. Any additional regions of the protein (e.g., Fc region) are generally human. Humanization can be performed using a method known in the art, for example, as described in U.S. Pat. Nos. 5,225,539, 6,054,297, 7,566,771, or U.S. Pat. No. 5,585,089. The term "humanized protein" also encompasses a super-humanized protein, for example, as described in U.S. Pat. No. 7,732,578. This term also encompasses a composite protein comprising, for example, one or more humanized variable regions and one or more, for example, human variable regions, chimeric variable regions, synhumanized variable regions or primatized variable regions.

In one example, a humanized CD83 binding protein comprises the regions between 27d and 34, 50 and 55, and 89 and 96 in a light chain sequence disclosed herein; and 31 and 35b, 50 and 58, and 95 and 101 in a heavy chain sequence disclosed herein (numbering according to the Kabat numbering system). In this regard, Padlan et al., FASEB J., 9: 133-139, 1995 presents evidence that these regions are those most likely to bind or contact antigen.

The CD83 binding proteins of the present disclosure may be human proteins. The term "human protein" as used herein refers to proteins having variable and, optionally, constant antibody regions found in humans, for example, in the human germline or somatic cells or from libraries produced using such regions. The "human" antibodies can include amino acid residues not encoded by human sequences, for example, mutations introduced by random or site directed mutations in vitro (in particular mutations which involve conservative substitutions or mutations in a small number of residues of the protein, for example, in 1, 2, 3, 4 or 5 of the residues of the protein). These "human antibodies" do not necessarily need to be generated as a result of an immune response of a human, rather, they can be generated using recombinant means (e.g., screening a phage display library) and/or by a transgenic animal (e.g., a mouse) comprising nucleic acid encoding human antibody constant and/or variable regions and/or using guided selection (e.g., as described in U.S. Pat. No. 5,565,332). This term also encompasses affinity matured forms of such antibodies. For the purposes of the present disclosure, a human protein will also be considered to include a protein comprising FRs from a human antibody or FRs comprising sequences from a consensus sequence of human FRs and in which one or more of the CDRs are random or semi-random, for example, as described in U.S. Pat. No. 6,300,064 and/or U.S. Pat. No. 6,248,516.

Exemplary human CD83 binding proteins are antibodies comprising the following pairs of variable regions:

(i) a $V_H$ sequence as shown in SEQ ID NO:2 and a $V_L$ sequence as shown in SEQ ID NO:6; or (ii) a $V_H$ sequence as shown in SEQ ID NO:2 and a $V_L$ sequence as shown in SEQ ID NO:7; or (iii) a $V_H$ sequence as shown in SEQ ID NO:2 and a $V_L$ sequence as shown in SEQ ID NO:8; or (iv) a $V_H$ sequence as shown in SEQ ID NO:2 and a $V_L$ sequence as shown in SEQ ID NO:9; or (v) a $V_H$ sequence as shown in SEQ ID NO:2 and a $V_L$ sequence as shown in SEQ ID NO:10; or (vi) a $V_H$ sequence as shown in SEQ ID NO:2 and a $V_L$ sequence as shown in SEQ ID NO:11; or (vii) a $V_H$ sequence as shown in SEQ ID NO:2 and a $V_L$ sequence as shown in SEQ ID NO:12; or (viii) a $V_H$ sequence as shown in SEQ ID NO:2 and a $V_L$ sequence as shown in SEQ ID NO:13; or (ix) a $V_H$ sequence as shown in SEQ ID NO:2 and a $V_L$ sequence as shown in SEQ ID NO:14; or (x) a $V_H$ sequence as shown in SEQ ID NO:2 and a $V_L$ sequence as shown in SEQ ID NO:15; or (xi) a $V_H$ sequence as shown in SEQ ID NO:2 and a $V_L$ sequence as shown in SEQ ID NO:16; or (xii) a $V_H$ sequence as shown in SEQ ID NO:2 and a $V_L$ sequence as shown in SEQ ID NO:17.

In one example, the $V_L$ sequence lacks the c-terminal lysine residue. The C-terminal lysine of the $V_L$ sequence of a CD83 binding protein of the disclosure may be removed, for example, during production or purification of the CD83 binding protein, or by recombinant engineering the nucleic acid encoding the $V_L$ of the CD83 binding protein. Accordingly, CD83 binding proteins may comprise populations with all C-terminal lysine residues of the $V_L$ removed, populations with no C-terminal lysine residues of the $V_L$ removed, or populations having a mixture of proteins with and without the $V_L$ C-terminal lysine residue. In some examples, the protein populations may additionally comprise proteins having two $V_L$s in which the C-terminal lysine residue is removed in one of the $V_L$s. Similarly, a composition of proteins may comprise the same or a similar mix of protein populations with or without the $V_L$ C-terminal lysine residue.

Optionally, the $V_H$ is linked to a heavy chain constant region, for example, an IgG1 heavy chain constant region. In one example, the heavy chain constant region lacks the c-terminal lysine residue.

Optionally, the $V_L$ is linked to a light chain constant region.

The CD83 binding proteins of the present disclosure may be synhumanized proteins. The term "synhumanized protein" refers to a protein prepared by a method described in US20080095767. A synhumanized CD83 binding protein includes a variable region of an antibody, wherein the variable region comprises FRs from a New World primate antibody variable region and CDRs from a non-New World primate antibody variable region. For example, a synhumanized CD83 binding protein includes a variable region of an antibody, wherein the variable region comprises FRs from a New World primate antibody variable region and CDRs from a mouse or rat antibody. In one example, the synhumanized CD83 binding protein is a CD83 binding antibody in which one or both of the variable regions are synhumanized. This term also encompasses a composite protein comprising, for example, one or more synhumanized variable regions and one or more, for example, human variable regions or humanized variable regions or chimeric variable regions.

The CD83 binding proteins of the present disclosure may be primatized proteins. A "primatized protein" comprises variable region(s) from an antibody generated following immunization of a non-human primate (e.g., a cynomolgus macaque). Optionally, the variable regions of the non-human primate antibody are linked to human constant regions to produce a primatized antibody. Exemplary methods for producing primatized antibodies are described in U.S. Pat. No. 6,113,898. This term also encompasses a composite protein comprising, for example, one or more primatized variable regions and one or more, for example, human variable regions or humanized variable regions or chimeric variable regions.

In one example, a CD83 binding protein of the disclosure is a chimeric protein. The term "chimeric proteins" refers to proteins in which an antigen binding domain is from a particular species (e.g., murine, such as mouse or rat) or belonging to a particular antibody class or subclass, while the remainder of the protein is from a protein derived from another species (such as, for example, human or non-human primate) or belonging to another antibody class or subclass. In one example, a chimeric protein is a chimeric antibody comprising a $V_H$ and/or a $V_L$ from a non-human antibody (e.g., a murine antibody) and the remaining regions of the antibody are from a human antibody. The production of such chimeric proteins is known in the art, and may be achieved by standard means (as described, e.g., in U.S. Pat. Nos. 6,331,415; 5,807,715; 4,816,567 and 4,816,397). This term also encompasses a composite protein comprising, for example, one or more chimeric variable regions and one or more, e.g., human variable regions or humanized variable regions or chimeric variable regions.

The present disclosure also contemplates a deimmunized CD83 binding protein, for example, as described in WO2000/34317 and US20070292416. De-immunized antibodies and proteins have one or more epitopes, for example, B cell epitopes or T cell epitopes removed (i.e., mutated) to thereby reduce the likelihood that a subject will raise an immune response against the antibody or protein. For example, a CD83-binding protein of the disclosure is analyzed to identify one or more B or T cell epitopes and one or more amino acid residues within the epitope is mutated to thereby reduce the immunogenicity of the CD83 binding protein.

It will be apparent to the skilled artisan from the foregoing disclosure that a "composite" protein comprises one form of $V_H$ (e.g., human) and another form of $V_L$ (e.g., humanized). The present disclosure explicitly encompasses all combinations of forms of $V_H$ and $V_L$.

Other CD83 Binding Proteins Comprising an Antigen Binding Domain

The present disclosure also contemplates other CD83 binding proteins comprising a variable region or antigen binding domain of an antibody, such as:

(i) a single-domain antibody, which is a single polypeptide chain comprising all or a portion of the $V_H$ or a $V_L$ of an antibody, for example, as described in U.S. Pat. No. 6,248,516);

(ii) diabodies, triabodies and tetrabodies, for example, as described in U.S. Pat. No. 5,844,094 and/or US2008152586;

(iii) scFvs, for example, as described in U.S. Pat. No. 5,260,203;

(iv) minibodies, for example, as described in U.S. Pat. No. 5,837,821;

(v) "key and hole" bispecific proteins, for example, as described in U.S. Pat. No. 5,731,168;

(vi) heteroconjugate proteins, for example, as described in U.S. Pat. No. 4,676,980;

(vii) heteroconjugate proteins produced using a chemical cross-linker, for example, as described in U.S. Pat. No. 4,676,980;

(viii) Fab'-SH fragments, for example, as described in Shalaby et al., J. Exp. Med., 175: 217-225, 1992; or (ix) Fab3, for example, as described in EP19930302894.

Constant Domain Fusions

The present disclosure encompasses CD83 binding proteins comprising an antigen binding domain of an antibody and a constant region or Fc or a domain thereof, for example, $C_H2$ and/or $C_H3$ domain. Suitable constant regions and/or domains will be apparent to the skilled artisan and/or the sequences of such polypeptides are readily available from publicly available databases. Kabat et al. also provide description of some suitable constant regions/domains.

Constant regions and/or domains thereof are useful for providing biological activities such as, dimerization, extended serum half-life (e.g., by binding to FcRn), antibody-dependent cell cytotoxicity (ADCC), complement dependent cytotoxicity (CDC), antibody-dependent cell phagocytosis (ADCP).

The present disclosure also contemplates CD83 binding proteins comprising mutant constant regions or domains, for example, as described in U.S. Pat. No. 7,217,797; U.S. Pat. No. 7,217,798; or US20090041770 (having increased half-life) or U.S. Pat. No. 7,355,008 (increased ADCC).

The C-terminal lysine of the heavy chain constant region of a CD83 binding protein of the disclosure comprising a constant region or Fc may be removed, for example, during production or purification of the CD83 binding protein, or by recombinantly engineering the nucleic acid encoding a heavy chain of the CD83 binding protein. Accordingly, CD83 binding proteins may comprise populations with all C-terminal lysine residues of the heavy chain constant region removed, populations with no C-terminal lysine residues of the heavy chain constant region removed, or populations having a mixture of proteins with and without the heavy chain constant region C-terminal lysine residue. In some examples, the protein populations may additionally comprise proteins having two heavy chain constant regions in which the heavy chain constant region C-terminal lysine residue is removed in one of the heavy chain constant regions. Similarly, a composition of proteins may comprise the same or a similar mix of protein populations with or without the heavy chain constant region C-terminal lysine residue.

Enhancing Effector Function

In one example, a CD83 binding protein of the present disclosure may induce effector function or enhanced effector function.

In the context of the present disclosure, "effector functions" refer to those biological activities mediated by cells or proteins that bind to the Fc region (a native sequence Fc region or amino acid sequence variant Fc region) of an antibody that result in killing of a cell. Examples of effector functions induced by antibodies include: complement dependent cytotoxicity (CDC); antibody-dependent-cell-mediated cytotoxicity (ADCC); antibody-dependent-cell-phagocytosis (ADCP); and B-cell activation.

"Antibody-dependent-cell-mediated cytotoxicity" or "ADCC" refers to lysis of antibody coated target cells by effector cells (e.g., natural killer ("NK") cells, neutrophils and macrophages) having Fc receptors that recognize the Fc region of the bound antibody. To assess ADCC activity of a molecule of interest, an in vitro ADCC assay may be performed. Useful effector cells for such assays include peripheral blood mononuclear cells ("PBMC") and NK cells.

In one example, a CD83 binding protein of the present disclosure binds to CD83 on the surface of a cell in such a manner that it is capable of inducing an effector function, such as, ADCC and/or CDC.

For example, the CD83 binding protein remains bound to the CD83 on the surface of the cell for a time sufficient to induce an effector function, such as ADCC and/or CDC.

In one example, a CD83 binding protein of the present disclosure is capable of inducing enhanced effector function, for example, by virtue of a modified Fc region or by virtue of comprising a region capable of binding to an immune effector cell. For example, the level of effector function is increased compared to the level induced by a human IgG1 or IgG4 Fc region. Enhancing effector function induced by a CD83 binding protein of the disclosure may result in enhanced therapeutic or prophylactic effects, for example, by killing or depleting cells causing a condition, for example, antigen presenting cells (APC) (e.g., dendritic cells (DCs)) and/or lymphocytes (e.g., T cells) that modulate aberrant or unwanted immune responses in, for example, inflammatory and/or autoimmune conditions or diseases. In one example, enhancing effector function prevents allogeneic stimulation of T cells, by for example, killing or depleting CD83+ cells that stimulate allogeneic T cells.

In one example, the Fc region of a CD83 binding protein of the disclosure is modified to increase the level of effector function it is capable of inducing compared to the Fc region without the modification. Such modifications can be at the amino acid level and/or the secondary structural level and/or the tertiary structural level and/or to the glycosylation of the Fc region.

The skilled addressee will appreciate that greater effector function may be manifested in any of a number of ways, for example as a greater level of effect, a more sustained effect or a faster rate of effect.

In one example, the Fc region comprises one or more amino acid modifications that increase its ability to induce enhanced effector function. In one example, the Fc region binds with greater affinity to one or more FcγRs, such as FcγRIII. In one example, the Fc region comprise at least one amino acid substitution at a position selected from the group consisting of: 230, 233, 234, 235, 239, 240, 243, 264, 266, 272, 274, 275, 276, 278, 302, 318, 324, 325, 326, 328, 330, 332, and 335, numbered according to the EU index of Kabat. In one example, the Fc region comprises the following amino acid substitutions S239D/I332E, numbered according to the EU index of Kabat. This Fc region has about 14 fold increase in affinity for FcγRIIIa compared to a wild-type Fc region and about 3.3 increased ability to induce ADCC compared to a wild-type Fc region. In one example, the Fc region comprises the following amino acid substitutions S239D/A330L/I332E, numbered according to the EU index of Kabat. This Fc region has about 138 fold increase in affinity for FcγRIIIa compared to a wild-type Fc region and about 323 fold increased ability to induce ADCC compared to a wild-type Fc region.

Additional amino acid substitutions that increase ability of a Fc region to induce effector function are known in the art and/or described, for example, in U.S. Pat. Nos. 6,737,056 or 7,317,091.

Methods for determining effector function are known in the art. In one example, the level of ADCC activity is assessed using a $^{51}$Cr release assay, an europium release assay or a $^{35}$S release assay. In each of these assays, cells expressing CD83 are cultured with one or more of the recited compounds for a time and under conditions sufficient for the compound to be taken up by the cell. In the case of a $^{35}$S release assay, the cells can be cultured with $^{35}$S-labeled methionine and/or cysteine for a time sufficient for the labeled amino acids to be incorporated into newly synthesized proteins. Cells are then cultured in the presence or absence of the protein and in the presence of immune effector cells, for example, PBMCs and/or NK cells. The amount of $^{51}$Cr, europium and/or $^{35}$S in cell culture medium is then detected, and an increase in the presence of the protein compared to in the absence of immunoglobulin indicates that the binding molecule/agent has effector function. Exemplary publications disclosing assays for assessing the level of ADCC induced by an immunoglobulin include Hellstrom et al. Proc. Natl Acad. Sci. USA 83: 7059-7063, 1986 and Bruggemann et al., J. Exp. Med. 166: 1351-1361, 1987.

Other assays for assessing the level of ADCC induced by an immunoglobulin include ACTI™ nonradioactive cytotoxicity assay for flow cytometry (CellTechnology, Inc. CA, USA) or CytoTox 96® non-radioactive cytotoxicity assay (Promega, Wis., USA).

Alternatively, or additionally, effector function of a CD83 binding protein is assessed by determining its affinity for one or more FcγRs, for example, as described in U.S. Pat. No. 7,317,091.

C1q binding assays may also be carried out to confirm that the CD83 binding protein is able to bind C1q and may induce CDC. To assess complement activation, a CDC assay may be performed (see, e.g., Gazzano-Santoro et al., J. Immunol. Methods 202: 163, 1996).

In another example, the CD83 binding protein comprises one or more amino acid substitutions that increase the half-life of the protein. For example, the CD83 binding protein comprises a constant region comprising one or more amino acid substitutions that increase the affinity of the constant region for the neonatal Fc region (FcRn). For example, the constant region has increased affinity for FcRn at lower pH, for example, about pH 6.0, to facilitate Fc/FcRn binding in an endosome. In one example, the constant region has increased affinity for FcRn at about pH 6 compared to its affinity at about pH 7.4, which facilitates the re-release of Fc into blood following cellular recycling. These amino acid substitutions are useful for extending the half life of a CD83 binding protein, by reducing clearance from the blood.

Exemplary amino acid substitutions include T250Q and/or M428L or T252A, T254S and T266F or M252Y, S254T and T256E or H433K and N434F according to the EU numbering system. Additional or alternative amino acid substitutions are described, for example, in US20070135620 or U.S. Pat. No. 7,083,784.

Mutant CD83 Binding Proteins

The present disclosure also provides a CD83 binding protein or a nucleic acid encoding same having at least 80% identity to a sequence disclosed herein. In one example, a CD83 binding protein or nucleic acid of the disclosure comprises sequence at least about 80% or 81% or 82% or 83% or 84% or 85% or 90% or 95% or 96% or 97% or 98% or 99% identical to a sequence disclosed herein, wherein the protein specifically binds to CD83.

Alternatively, or additionally, the CD83 binding protein comprises a CDR (e.g., three CDRs) at least about 30% or 35% or 40% or 45% or 50% or 55% or 60% or 65% or 70% or 75% or 80% or 85% or 90% or 95% or 97% or 98% or 99% identical to CDR(s) of a $V_H$ or $V_L$ as described herein according to any example, wherein the protein is capable of specifically binding to CD83. In this regard, the inventors have produced numerous antibodies having diverse sequences within their CDRs. Methods for determining binding of a protein CD83 are described herein.

For example, the inventors have identified a group of CD83 binding proteins sharing at least about 60% identity in their light chain CDR1, such as, for example, with at least about 65% or 70% or 75% or 80% or 85% or 90% or 95% or 96% or 97% or 98% or 99% identity in their light chain CDR1 according to the Kabat numbering system.

The inventors have also identified a group of CD83 binding proteins sharing 70% identity in their light chain CDR2, such as, for example, with at least about 75% or 80% or 85% or 90% or 95% or 96% or 97% or 98% or 99% identity in their light chain CDR2 according to the Kabat numbering system.

The inventors have also identified a group of CD83 binding proteins sharing 30% identity in their light chain CDR3, such as, for example, with at least about 35% or 40% or 45% or 50% or 55% or 60% or 65% or 70% or 75% or 80% or 85% or 90% or 95% or 96% or 97% or 98% or 99% identity in their light chain CDR3 according to the Kabat numbering system.

As discussed herein, the four N-terminal amino acids of a light chain CDR1 can be deleted or any one or more of those amino acids can be substituted with another naturally-occurring amino acid (Padlan et al., FASEB J., 9: 133-139, 1995). Thus, a CD83 binding protein of the disclosure can comprise a CDR1 having at least about 70% identity to a light chain CDR1 sequence disclosed herein.

In another example, a nucleic acid of the disclosure comprises a sequence at least about 80% or 85% or 90% or 95% or 97% or 98% or 99% identical to a sequence disclosed herein and encoding a CD83 binding protein which is capable of specifically binding to CD83. The present disclosure also encompasses nucleic acids encoding a CD83 binding protein of the disclosure, which differs from a sequence exemplified herein as a result of degeneracy of the genetic code.

The % identity of a nucleic acid or polypeptide is determined by GAP (Needleman and Wunsch. Mol. Biol. 48, 443-453, 1970) analysis (GCG program) with a gap creation penalty=5, and a gap extension penalty=0.3. The query sequence is at least 50 residues in length, and the GAP analysis aligns the two sequences over a region of at least 50 residues. For example, the query sequence is at least 100 residues in length and the GAP analysis aligns the two sequences over a region of at least 100 residues. For example, the two sequences are aligned over their entire length.

As discussed above, the present disclosure also contemplates a nucleic acid that hybridizes under stringent hybridization conditions to a nucleic acid encoding a CD83 binding protein described herein, for example, nucleic acid encoding a $V_H$ or $V_L$ of antibody hFab4.1, hFab4.1, hFab4.3, hFab4.4, hFab4.4, hFab4.5, hFab4.7, hFab4.8, hFab4.9, hFab4.10, hFab4.12, hFab4.18. A "moderate stringency" is defined herein as being a hybridization and/or washing carried out in 2×SSC buffer, 0.1% (w/v) SDS at a temperature in the range 45° C. to 65° C., or equivalent conditions. A "high stringency" is defined herein as being a hybridization and/or wash carried out in 0.1×SSC buffer, 0.1% (w/v) SDS, or lower salt concentration, and at a temperature of at least 65° C., or equivalent conditions. Reference herein to a particular level of stringency encompasses equivalent conditions using wash/hybridization solutions other than SSC known to those skilled in the art. For example, methods for calculating the temperature at which the strands of a double stranded nucleic acid will dissociate (also known as melting temperature, or Tm) are known in the art. A temperature that is similar to (e.g., within 5° C. or within 10° C.) or equal to the Tm of a nucleic acid is considered to be high stringency. Medium stringency is to be considered to be within 10° C. to 20° C. or 10° C. to 15° C. of the calculated Tm of the nucleic acid.

The present disclosure also contemplates mutant forms of a CD83 binding protein of the disclosure comprising one or more conservative amino acid substitutions compared to a sequence set forth herein. In some examples, the CD83 binding protein comprises 10 or fewer, for example, 9 or 8 or 7 or 6 or 5 or 4 or 3 or 2 or 1 conservative amino acid substitutions. A "conservative amino acid substitution" is one in which the amino acid residue is replaced with an amino acid residue having a similar side chain and/or hydropathicity and/or hydrophilicity.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), (3-branched side chains (e.g., threonine, valine, isoleucine) and aromatic side chains (e.g., tyrosine, phenylalanine, tryptophan, histidine). Hydropathic indices are described, for example, in Kyte and Doolittle J. Mol. Biol., 157: 105-132, 1982 and hydrophylic indices are described in, for example, U.S. Pat. No. 4,554,101.

The present disclosure also contemplates non-conservative amino acid changes. For example, of particular interest are substitutions of charged amino acids with another charged amino acid and with neutral or positively charged amino acids. In some examples, the CD83 binding protein comprises 10 or fewer, for example, 9 or 8 or 7 or 6 or 5 or 4 or 3 or 2 or 1 non-conservative amino acid substitutions.

In one example, the mutation(s) occur within a FR of an antigen binding domain of a CD83 binding protein of the disclosure. In another example, the mutation(s) occur within a CDR of a CD83 binding protein of the disclosure.

Exemplary methods for producing mutant forms of a CD83 binding protein include:
mutagenesis of DNA (Thie et al., Methods Mol. Biol. 525: 309-322, 2009) or RNA (Kopsidas et al., Immunol. Lett. 107:163-168, 2006; Kopsidas et al. BMC Biotechnology, 7: 18, 2007; and WO1999/058661);
introducing a nucleic acid encoding the polypeptide into a mutator cell, for example, XL-1Red, XL-mutS and XL-mutS-Kanr bacterial cells (Stratagene);
DNA shuffling, for example, as disclosed in Stemmer, Nature 370: 389-91, 1994; and
site directed mutagenesis, for example, as described in Dieffenbach (ed) and Dveksler (ed) (In: PCR Primer: A Laboratory Manual, Cold Spring Harbor Laboratories, N Y, 1995).

Exemplary methods for determining biological activity of the mutant CD83 binding proteins of the disclosure will be apparent to the skilled artisan and/or described herein, for example, antigen binding. For example, methods for determining antigen binding, competitive inhibition of binding, affinity, association, dissociation and therapeutic efficacy are described herein.

Methods for Producing Proteins

Recombinant Expression

As discussed herein, a nucleic acid encoding a CD83 binding protein of the disclosure and/or one or more polypeptides thereof is introduced into an expression construct, such that it is operably linked to a promoter to thereby facilitate its expression. Methods for producing expression constructs, for example, cloning into expression constructs/vectors are known in the art and/or described in Ausubel et al., (In: Current Protocols in Molecular Biology. Wiley Interscience, ISBN 047 150338, 1987), and (Sambrook et al., (In: Molecular Cloning: Molecular Cloning: A Laboratory Manual, Cold Spring Harbor Laboratories, New York, Third Edition 2001) and U.S. Pat. No. 7,270,969.

In one example, the CD83 binding protein of the disclosure is expressed in a bacterial cell. Typical promoters suitable for expression in bacterial cells such as, for example, a bacterial cell selected from the group comprising *E. coli, Staphylococcus* sp., *Corynebacterium* sp., *Salmonella* sp., *Bacillus* sp., and *Pseudomonas* sp., include, but are not limited to a promoter such as lacz, Ipp, a temperature-sensitive L or R promoters, T7, T3, SP6 or semi-artificial promoters such as the IPTG-inducible tac promoter or lacUV5 promoter.

In another example, the CD83 binding protein is expressed in a yeast cell. Typical promoters suitable for expression in yeast cells such as, *Pichia pastoris, Saccharomyces cerevisiae* and *S. pombe*, include, but are not limited to, promoters from the following genes ADH1, GAL1, GAL4, CUP1, PHO5, nmt, RPR1, or TEF1.

In a further example, the CD83 binding protein is expressed in an insect cell. Typical promoters suitable for expression in insect cells, or in insects, include, but are not limited to, the OPEI2 promoter, the insect actin promoter isolated from *Bombyx* muri, the *Drosophila* sp. dsh promoter (Marsh et al., Hum. Mol. Genet. 9, 13-25, 2000).

A CD83 binding protein of the disclosure can also be expressed in plant cells. Promoters for expressing peptides in plant cells are known in the art, and include, but are not limited to, the *Hordeum vulgare* amylase gene promoter, the cauliflower mosaic virus 35S promoter, the nopaline synthase (NOS) gene promoter, and the auxin inducible plant promoters P1 and P2.

In one example, a CD83 binding protein of the disclosure is expressed in a mammalian cell or in a mammal. Typical promoters suitable for expression in a mammalian cell include, for example a promoter selected from the group consisting of, retroviral LTR elements, the SV40 early promoter, the SV40 late promoter, the CMV IE (cytomegalovirus immediate early) promoter, the EF1 promoter (from human elongation factor 1), the EM7 promoter, the UbC promoter (from human ubiquitin C). Examples of useful mammalian host cell lines include monkey kidney CV1 line transformed by SV40 (COS-7); human embryonic kidney line (HEK-293 cells); baby hamster kidney cells (BHK); Chinese hamster ovary cells (CHO); African green monkey kidney cells (VERO-76); or myeloma cells (e.g., NS/0 cells).

Exemplary cells used for expressing a CD83 binding protein of the disclosure are CHO cells, myeloma cells or HEK cells. The cell may further comprise one or more genetic mutations and/or deletions that facilitate expression of a modified antibody.

Other elements of expression constructs/vectors are known in the art and include, for example, enhancers, transcriptional terminators, polyadenylation sequences, nucleic acids encoding selectable or detectable markers and origins of replication.

In one example, an expression construct is a bicistronic expression construct. By "bicistronic" is meant a single nucleic acid molecule that is capable of encoding two distinct polypeptides from different regions of the nucleic acid, for example, a single nucleic acid capable of encoding a $V_H$ containing polypeptide and a $V_L$ containing polypeptide as distinct polypeptides. Generally, the regions encoding each distinct polypeptide are separated by an internal ribosome entry site (IRES) and the region 5' of the IRES does not comprise a transcription termination sequence. Exemplary IRESs are described, for example, in US20090247455.

Following production of a suitable expression construct, it is introduced into a suitable cell using any method known in the art. Exemplary methods include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The cells used to produce the CD83 binding proteins of this disclosure are then cultured under conditions known in the art to produce the CD83 binding protein of the disclosure.

Cell free expression systems are also contemplated by the present disclosure, for example, the TNT T7 and TNT T3 systems (Promega), the pEXP1-DEST and pEXP2-DEST vectors (Invitrogen).

Protein Purification

Following production/expression, a CD83 binding protein of the disclosure is purified using a method known in the art. Such purification provides the protein of the disclosure substantially free of nonspecific protein, acids, lipids, carbohydrates, and the like. In one example, the protein will be in a preparation wherein more than about 90% (e.g., 95%, 98% or 99%) of the protein in the preparation is a CD83 binding protein of the disclosure.

Standard methods of peptide purification are employed to obtain an isolated CD83 binding protein of the disclosure, including but not limited to various high-pressure (or performance) liquid chromatography (HPLC) and non-HPLC polypeptide isolation protocols, such as size exclusion chromatography, ion exchange chromatography, hydrophobic interaction chromatography, mixed mode chromatography, phase separation methods, electrophoretic separations, precipitation methods, salting in/out methods, immunochromatography, and/or other methods.

In one example, affinity purification is useful for isolating a fusion protein comprising a label. Methods for isolating a protein using affinity chromatography are known in the art and described, for example, in Scopes (In: Protein purification: principles and practice, Third Edition, Springer Verlag, 1994). For example, an antibody or compound that binds to the label (in the case of a polyhistidine tag this may be, for example, nickel-NTA) is immobilized on a solid support. A sample comprising a protein is then contacted to the immobilized antibody or compound for a time and under conditions sufficient for binding to occur. Following washing to remove any unbound or non-specifically bound protein, the protein is eluted.

In the case of a CD83 binding protein comprising a Fc region of an antibody, protein A or protein G or modified forms thereof can be used for affinity purification. Protein A is useful for isolating purified proteins comprising a human γ1, γ2, or γ4 heavy chain Fc region. Protein G is recommended for all mouse Fc isotypes and for human γ3.

Conjugates

In one example, a CD83 binding protein of the present disclosure is conjugated to a compound. For example, the compound is selected from the group consisting of a radioisotope, a detectable label, a therapeutic compound, a colloid, a toxin, a nucleic acid, a peptide, a protein, a compound that increases the half-life of the CD83 binding protein in a subject and mixtures thereof.

The other compound can be directly or indirectly bound to the CD83 binding protein (e.g., can comprise a linker in the case of indirect binding). Examples of compounds include, a radioisotope (e.g., iodine-131, yttrium-90 or indium-111), a detectable label (e.g., a fluorophore or a fluorescent nanocrystal), a therapeutic compound (e.g., a chemotherapeutic or an anti-inflammatory), a colloid (e.g., gold), a toxin (e.g., ricin or tetanus toxoid), a nucleic acid, a peptide (e.g., a serum albumin binding peptide), a protein (e.g., a protein comprising an antigen binding domain of an antibody or serum albumin), a compound that increases the half-life of the CD83 binding protein in a subject (e.g., polyethylene glycol or other water soluble polymer having this activity) and mixtures thereof. Exemplary compounds that can be conjugated to a CD83 binding protein of the disclosure and methods for such conjugation are known in the art and described, for example, in WO2010/059821.

Some exemplary compounds that can be conjugated to a CD83 binding protein of the present disclosure are listed in Table 2.

TABLE 2

Compounds useful in conjugation.

| Group | Detail |
|---|---|
| Radioisotopes (either directly or indirectly) | $^{123}$I, $^{125}$I, $^{130}$I, $^{133}$I, $^{135}$I, $^{47}$Sc, $^{72}$As, $^{72}$Sc, $^{90}$Y, $^{88}$Y, $^{97}$Ru, $^{100}$Pd, $^{101m}$Rh, $^{101m}$Rh, $^{119}$Sb, $^{128}$Ba, $^{197}$Hg, $^{211}$At, $^{212}$Bi, $^{153}$Sm, $^{169}$Eu, $^{212}$Pb, $^{109}$Pd, $^{111}$In, $^{67}$Gu, $^{68}$Gu, $^{67}$Cu, $^{75}$Br, $^{76}$Br, $^{77}$Br, $^{99m}$Tc, $^{11}$C, $^{13}$N, $^{15}$O, $^{18}$I, $^{188}$Rc, $^{203}$Pb, $^{64}$Cu, $^{105}$Rh, $^{198}$Au, $^{199}$Ag, or $^{177}$Lu |
| Half-life extenders | Polyethylene glycol<br>Glycerol<br>Glucose |
| Fluorescent probes | Phycoerythrin (PE)<br>Allophycocyanin (APC)<br>Alexa Fluor 488<br>Cy5.5 |
| Biologics | fluorescent proteins such as Renilla luciferase, GFP<br>immune modulators, such as cytokines<br>toxins<br>an immunoglobulin or antibody or antibody variable region<br>half-life extenders such as albumin or antibody variable regions or peptides that bind to albumin |
| Chemotherapeutics | Taxol<br>5-FU<br>Doxorubicin<br>Idarubicin |

Screening Assays

CD83 binding proteins of the present disclosure are readily screened for biological activity, for example, as described below.

Binding Assays

One form of assay is an antigen binding assay, for example, as described in Scopes (In: Protein purification: principles and practice, Third Edition, Springer Verlag, 1994). Such a method generally involves labeling the CD83 binding protein and contacting it with immobilized antigen. Following washing to remove non-specific bound protein, the amount of label and, as a consequence, bound protein is detected. Of course, the CD83 binding protein can be immobilized and the antigen labeled. Panning-type assays, for example, as described or exemplified herein can also be used. Alternatively, or additionally, surface plasmon resonance assays can be used.

In one example, a binding assay is performed with peptide comprising an epitope of CD83. In this way, CD83 binding proteins that bind to a specific region of CD83 are selected.

In Vivo Assays

CD83 binding proteins of the present disclosure can also be assessed for therapeutic efficacy in an animal model of a condition, for example, a CD83 mediated condition. For example, the CD83 binding protein is administered to a model of inflammatory bowel disease or colitis (e.g., dextran sodium sulphate (DSS)-induced colitis or CD45Rb adoptive transfer model of colitis (e.g., Kanai et al., Inflamm. Bowel Dis. 12: 89-99, 2006). In another example, a CD83 binding protein is administered to a model of multiple sclerosis, for example, EAE models in which a mouse or rat is immunized with a myelin sheath protein or peptide derived therefrom (e.g., MOG, MBP or PLP) and an immune response is generated against the protein thereby inducing a model of multiple sclerosis. Exemplary EAE models are reviewed in, for example Tsunoda and Fujinami, J. Neuropathol. Exp. Neurol. 55: 673-686, 1996. The CD83 binding protein can also or alternatively be tested in a model of arthritis, for example, a SKG strain of mouse (Sakaguchi et al., Nature 426: 454-460, 1995), rat type II collagen arthritis model, mouse type II collagen arthritis model or antigen induced arthritis models (Bendele J. Musculoskel. Neuron. Interact. 1: 377-385, 2001) and/or a model of inflammatory airway disease (for example, OVA challenge or cockroach antigen challenge).

The therapeutic efficacy of a CD83 binding protein of the present disclosure can also or alternatively be assessed in a model of graft-versus-host-response, for example, in which splenocytes from one animal are injected into a allogeneic animal (e.g., a MHC or HLA unmatched animal). In one example, human peripheral blood mononuclear cells (PBMCs) are transplanted into a xenogeneic SCID mouse model via, for example, intraperitoneal injection after sub lethal total body irradiation inducing a fatal human CD4$^+$ T cell mediated graft versus host response that requires human DCs. Treatment with a CD83 binding protein of the disclosure can be administered to mice, by, for example, intraperitoneal injection on the day of PBMC transplant (day 0) and mice scored for clinical manifestations of GVDH.

Competitive Binding Assays

Assays for determining a CD83 binding protein that competitively inhibits binding of an antibody of the disclosure will be apparent to the skilled artisan. For example, the antibody of the disclosure is conjugated to a detectable label, for example, a fluorescent label or a radioactive label. The labeled antibody and the test CD83 binding protein are then mixed and contacted with CD83 or a peptide comprising an epitope thereof. The level of labeled antibody is then determined and compared to the level determined when the labeled antibody is contacted with the CD83 or the peptide comprising an epitope thereof in the absence of the CD83 binding protein. If the level of labeled antibody is reduced in the presence of the CD83 binding protein compared to the absence of the CD83 binding protein, the CD83 binding protein competitively inhibits binding of the antibody.

Optionally, the CD83 binding protein is conjugated to a different label than the antibody. This permits detection of the level of binding of the CD83 binding protein to CD83 or epitope bearing peptide.

In another example, the CD83 binding protein is permitted to bind to CD83 or a peptide comprising an epitope thereof prior to contacting the CD83 or peptide with an antibody described herein. A reduction in the amount of bound antibody in the presence of the CD83 binding protein compared to in the absence of the CD83 binding protein indicates that the CD83 binding protein competitively inhibits binding of the antibody to CD83. A reciprocal assay can also be performed using labeled CD83 binding protein and first allowing the antibody to bind to CD83 or the peptide. In this case, a reduced amount of labeled CD83 binding protein bound to CD83 or the peptide in the presence of the antibody compared to in the absence of antibody indicates that the CD83 binding protein competitively inhibits binding of the antibody to CD83.

Epitope Mapping Assays

In another example, the epitope bound by a protein described herein is mapped. Epitope mapping methods will be apparent to the skilled artisan. For example, a series of overlapping peptides spanning the CD83 sequence or a region thereof comprising an epitope of interest, for example, peptides comprising 10 to 15 amino acids are produced. The CD83 binding protein is then contacted to each peptide or a combination thereof and the peptide(s) to which it binds determined. This permits determination of peptide(s) comprising the epitope to which the CD83 binding protein binds. If multiple non-contiguous peptides are bound by the protein, the protein may bind a conformational epitope.

Alternatively, or in addition, amino acid residues within CD83 are mutated, for example, by alanine scanning mutagenesis, and mutations that reduce or prevent protein binding are determined. Any mutation that reduces or prevents binding of the CD83 binding protein is likely to be within the epitope bound by the protein.

A further method involves binding CD83 or a region thereof to an immobilized CD83 binding protein of the present disclosure and digesting the resulting complex with proteases. Peptide that remains bound to the immobilized protein are then isolated and analyzed, for example, using mass spectrometry, to determine their sequence.

A further method involves converting hydrogens in CD83 or a region thereof to deuterium atoms and binding the resulting protein to an immobilized CD83 binding protein of the present disclosure. The deuterium atoms are then converted back to hydrogen, the CD83 or region thereof isolated, digested with enzymes and analyzed, for example, using mass spectrometry to identify those regions comprising deuterium, which would have been protected from conversion to hydrogen by the binding of a CD83 binding protein described herein.

Half Life Assays

Some CD83 binding proteins encompassed by the present disclosure have an improved half-life, for example, are modified to extend their half-life compared to CD83 binding proteins that are unmodified. Methods for determining a CD83 binding protein with an improved half-life will be apparent to the skilled person. For example, the ability of a CD83 binding protein to bind to a neonatal Fc receptor (FcRn) is assessed. In this regard, increased binding affinity for FcRn increased the serum half-life of the CD83 binding protein (see for example, Kim et al., Eur. J. Immunol., 24: 2429, 1994).

The half-life of a CD83 binding protein of the disclosure can also be measured by pharmacokinetic studies, for example, according to the method described by Kim et al, Eur. J. of Immunol. 24: 542, 1994. According to this method, radiolabeled CD83 binding protein is injected intravenously into mice and its plasma concentration is periodically measured as a function of time, for example at 3 minutes to 72 hours after the injection. The clearance curve thus obtained should be biphasic, that is, an alpha phase and beta phase. For the determination of the in vivo half-life of the CD83 binding protein, the clearance rate in beta-phase is calculated and compared with that of the wild type or unmodified CD83 binding protein.

Stability Assays

Stability of a CD83 binding protein of the disclosure can be assessed by any of a variety of assays. For example, the CD83 binding protein is exposed to a condition, for example, heat or acid or stored for a period of time (e.g., 1 month) at room temperature. Aggregation of the CD83 binding protein can then be assessed by determining turbidity (with an increase in turbidity following exposure to the condition indicating instability), size exclusion chromatography, non-reducing gel electrophoresis or a binding or neutralization study described herein.

Pharmaceutical Compositions and Methods of Treatment

The CD83 binding protein of the present disclosure or nucleic acid encoding same or cell expressing same (syn. active ingredient) is useful for parenteral, topical, oral, or local administration, aerosol administration, or transdermal administration, for prophylactic or for therapeutic treatment.

Formulation of a CD83 binding protein or nucleic acid encoding same or cell expressing same to be administered will vary according to the route of administration and formulation (e.g., solution, emulsion, capsule) selected. An appropriate pharmaceutical composition comprising CD83 binding protein or nucleic acid encoding same or cell expressing same to be administered can be prepared in a physiologically acceptable carrier. A mixture of CD83 binding proteins can also be used. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, Remington's Pharmaceutical Science, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The CD83 binding protein of this disclosure can be lyophilized for storage and reconstituted in a suitable carrier prior to use according to art-known lyophilization and reconstitution techniques.

The optimum concentration of the active ingredient(s) in the chosen medium can be determined empirically, according to procedures well known to the skilled artisan, and will depend on the ultimate pharmaceutical formulation desired.

The dosage ranges for the administration of the CD83 binding protein of the disclosure are those large enough to produce the desired effect. For example, the composition comprises a therapeutically or prophylactically effective amount of the CD83 binding protein or nucleic acid encoding same or cell expressing same.

As used herein, the term "effective amount" shall be taken to mean a sufficient quantity of the CD83 binding protein, nucleic acid, or cells to induce/increase or inhibit/reduce/prevent CD83 activity in a subject. The skilled artisan will be aware that such an amount will vary depending on, for example, the CD83 binding protein, nucleic acid, or cells and/or the particular subject and/or the type or severity of a condition being treated. Accordingly, this term is not to be construed to limit the disclosure to a specific quantity, for example, weight or number of CD83 binding proteins, nucleic acids, or cells.

As used herein, the term "therapeutically effective amount" shall be taken to mean a sufficient quantity of CD83 binding protein, nucleic acid, or cells to reduce or inhibit one or more symptoms of a condition.

As used herein, the term "prophylactically effective amount" shall be taken to mean a sufficient quantity of CD83 binding protein, nucleic acid or cells to prevent or inhibit or delay the onset of one or more detectable symptoms of a condition.

The dosage should not be so large as to cause adverse side effects, such as hyper viscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication. Dosage can vary from about 0.1 mg/kg to about 300 mg/kg, for example, from about 0.2 mg/kg to about 200 mg/kg, such as, from about 0.5 mg/kg to about 20 mg/kg, in one or more dose administrations daily, for one or several days.

In one example, the CD83 binding protein is administered subcutaneously or intravenously.

In some examples, the CD83 binding protein or other active ingredient is administered at an initial (or loading) dose which is higher than subsequent (maintenance doses). For example, the binding molecule is administered at an initial dose of between about 1 mg/kg to about 30 mg/kg. The binding molecule is then administered at a maintenance dose of between about 0.0001 mg/kg to about 1 mg/kg. The maintenance doses may be administered every 7 to 35 days, such as, every 14 or 21 or 28 days.

In some examples, a dose escalation regime is used, in which a CD83 binding protein or other active ingredient is initially administered at a lower dose than used in subsequent doses. This dosage regime is useful in the case of subject's initially suffering adverse events In the case of a subject that is not adequately responding to treatment, multiple doses in a week may be administered. Alternatively, or in addition, increasing doses may be administered.

One or more CD83 binding proteins of the present disclosure can be administered to an individual by an appropriate route, either alone or in combination with (before, simultaneous with, or after) another drug or agent. For example, the CD83 binding protein of the present disclosure can also be used in combination with proteins, for example, a TNF antagonist, an anti-IL-12/23 antibody, an anti-inflammatory, a corticosteroid, methotrexate or a painkiller. The CD83 binding protein of the present disclosure can be used as separately administered compositions given in conjunction with antibiotics and/or antimicrobial agents.

It will be appreciated by those skilled in the art that the CD83 binding proteins of the present disclosure may be introduced into a subject by administering an expression construct of the disclosure or a cell expressing a CD83 binding protein of the disclosure. A variety of methods can be used for introducing a nucleic acid encoding the antibody into a target cell in vivo. For example, the naked nucleic acid may be injected at the target site, may be encapsulated into liposomes, or may be introduced by way of a viral vector.

CD83 Detection Assays

The following assays can be performed with a CD83 binding protein of the disclosure, for example, a CD83 binding protein conjugated to a detectable label as discussed herein. Detection of CD83 with an assay described herein is useful for diagnosing or prognosing a condition.

An immunoassay is an exemplary assay format for diagnosing a condition in a subject or detecting CD83 in a sample. The present disclosure contemplates any form of immunoassay, including Western blotting, enzyme-linked immunosorbent assay (ELISA), fluorescence-linked immunosorbent assay (FLISA), competition assay, radioimmunoassay, lateral flow immunoassay, flow-through immunoassay, electrochemiluminescent assay, nephelometric-based assays, turbidometric-based assay, and fluorescence activated cell sorting (FACS)-based assays.

One form of a suitable immunoassay is, for example, an ELISA or FLISA.

In one form, such an assay involves immobilizing a CD83 binding protein of the disclosure onto a solid matrix, such as, for example a polystyrene or polycarbonate microwell or dipstick, a membrane, or a glass support (e.g., a glass slide). A test sample is then brought into direct contact with the CD83 binding protein and CD83 in the sample is bound or captured. Following washing to remove any unbound protein in the sample, a protein that binds to CD83 at a distinct epitope is brought into direct contact with the captured CD83. This detector protein is generally labeled with a detectable reporter molecule, such as, for example, an enzyme (e.g. horseradish peroxidase (HRP)), alkaline phosphatase (AP) or β-galactosidase) in the case of an ELISA or a fluorophore in the case of a FLISA. Alternatively, a second labeled protein can be used that binds to the detector protein. Following washing to remove any unbound protein the detectable reporter molecule is detected by the addition of a substrate in the case of an ELISA, such as, for example, hydrogen peroxide, TMB, or toluidine, or 5-bromo-4-chloro-3-indol-beta-D-galactopyranoside (x-gal). Of course, the immobilized (capture) protein and the detector protein may be used in the opposite manner.

The level of the antigen in the sample is then determined using a standard curve that has been produced using known quantities of the marker or by comparison to a control sample.

The assays described above are readily modified to use chemiluminescence or electrochemiluminescence as the basis for detection.

As will be apparent to the skilled artisan, other detection methods based on an immunosorbent assay are useful in the performance of the present disclosure. For example, an immunosorbent method based on the description supra using a radiolabel for detection, or a gold label (e.g., colloidal gold) for detection, or a liposome, for example, encapsulating NAD+ for detection or an acridinium linked immunosorbent assay.

In some examples of the disclosure, the level of CD83 is determined using a surface plasmon resonance detector (e.g., BIAcore™, GE Healthcare, Piscataway, N.J.), a flow through device, for example, as described in U.S. Pat. No. 7,205,159, a micro- or nano-immunoassay device (e.g., as described in US20030124619), a lateral flow device (e.g., as described in US20040228761 or US20040265926), a fluorescence polarization immunoassay (FPIA e.g., as described in U.S. Pat. Nos. 4,593,089 or 4,751,190), or an immunoturbidimetric assay (e.g., as described in U.S. Pat. Nos. 5,571,728 or 6,248,597).

Conditions or Disease

The CD83 binding proteins of the disclosure can be used for the treatment, prevention, diagnosis or prophylaxis of a CD83 associated condition or disease.

Exemplary conditions or disease that can be treated, prevented, diagnosed, or prognosed by performing a method of the disclosure include inflammatory or autoimmune conditions or diseases.

Exemplary conditions and diseases include allergies, asthma, graft rejection, autoimmune conditions such as myasthemia gravis, multiple sclerosis, vasculitis, cronic inflammatory bowel diseases such as Morbus Crohn or colitis ulcerosa, HLA B27-associated autoimmunopathis such as Morbus Bechterew, and systemic lupus erythematosis, skin diseases such as psoriasis, rheumatoid arthritis, insulin-dependent diabetes mellitus and AIDS.

In one example, the CD83 binding protein of the disclosure depletes immune cells such as antigen presenting cells (APC) (e.g., dendritic cells (DCs)) and/or lymphocytes (e.g., T cells) to modulate aberrant or unwanted immune responses in, for example, inflammatory and/or autoimmune conditions or diseases. In one example, the CD83 binding protein is an antibody which specifically binds to the surface of an APC and/or lymphocyte and depletes the APC and/or lymphocyte via antibody dependent mediated cytotoxicity (ADCC). In one example, ADCC is mediated by natural killer (NK) cells.

In one example, the CD83 binding protein of the disclosure bind to and deplete CD83 expressing tumors and/or cancer cells. Thus, the disclosure also provides a method for treating a CD83 expressing tumor or cancer, the method comprising administering a CD83 binding protein of the disclosure or composition comprising same. Exemplary CD83 expressing cancers/tumors include, lung cancer, breast cancer, colon cancer, colorectal cancer, melanoma and hematopoietic cancers, such as lymphomas and leukemias.

Graft Rejection

In one example, the CD83 binding proteins of the disclosure can be used to deplete immune cells such as APCs and/or lymphocytes to modulate immune responses associated with for, example, rejection of a graft by, for example, graft versus host disease or host versus graft disease. In one example, the graft is an organ or tissue or cell graft. In one example, the graft is an allograft. In one example, the graft is an autologic graft.

In one example, the graft is a hematopoietic stem cell graft.

Graft versus host disease may result where an immunocompetent graft, for example, an allogeneic hematopoietic stem cell graft, is administered with viable and functional immune cells to a recipient, for example, an histo-incompatible recipient, and the immune cells present in the graft, for example, T cells, attack tissues of the transplant recipient. Graft versus host disease may be chronic or acute and the present disclosure contemplate treating chronic graft versus host disease or acute graft versus host disease.

Acute graft versus host disease is generally accepted as occurring within the first 3 months after a transplant. Common acute symptoms include:
Abdominal pain or cramps, nausea, vomiting, and diarrhea;
Dry or irritated eyes;
Jaundice (yellow coloring of the skin or eyes); and/or
Skin rash, itching, redness on areas of the skin Chronic graft versus host disease is generally recognized as occurring more than 3 months after a transplant. Chronic symptoms may include:
Dry eyes or vision changes;
Dry mouth, white patches inside the mouth, and sensitivity to spicy foods;
Fatigue, muscle weakness, and chronic pain;
Skin rash with raised, discolored areas, as well as skin tightening or thickening;
Shortness of breath; and/or
Weight loss Host versus graft disease may result where antigens derived from the allogenic graft are presented by either donor or recipient APCs to immune cells of the recipient, for example, T cells, which are in turn activated to become effector immune cells, for example, cytotoxic T lymphoctes (CTLs) that then attack the transplant.

An "allogeneic graft" is a graft from a genetically non-identical donor (e.g., histo-incompatible donor) of the same species.

The present disclosure contemplates treatment of (or prevention of) rejection of any form of graft, including any form of stem cell or progenitor cell, such as endothelial progenitor cells, mesenchymal stem cells, etc.

Hematopoietic Stem Cell Transplantation (HSCT)

A "hematopoietic stem cell transplantation (HSCT)" is a graft comprising multipotent hematopoietic stem cells which can be derived, for example, from bone marrow, umbilical cord blood or peripheral blood. The transplant may include some non-stem cells, for example, APCs including DCs and/or lymphocytes.

"Hematopoietic stem cells" can self-renew and differentiate to give rise to all the blood cell types including myeloid (monocytes and macrophages, neutrophils, basophils, eosinophils, dendritic cells), erythroid (erythrocytes), megakaryocytic (platelets) and lymphoid lineages (T-cells, B-cells, NK-cells). Throughout differentiation, the hematopoietic stem cell first loses its self-renewal capacity, then loses lineage potential step by step as it commits to becoming a mature effector cell. Typically a Lin–, CD34+, CD38–, CD90+, CD45RA– human cell is a hematopoietic stem cell. In one example, expression of CD34 is used to identify hematopoietic stem cells in peripheral blood isolated from human donors.

HSCT can be used in the treatment of diseases and conditions which require stem cell transplants. For example, the stem cells can be used for the treatment of failure or dysfunction of normal blood cell production and maturation, hematopoietic malignancy, autoimmune disease, liver disease, or immunodeficiency (by reason of for example, irradiation, chemotherapy or infection with a pathogen).

The stem cells may be expanded or differentiated ex vivo prior to administration to a subject.

Allogeneic hematopoietic stem-cell transplantation may be used to treat one or more of the following conditions: acute myeloid leukemia, acute lymphoblastic leukemia, chronic myeloid leukemia, chronic lymphocytic leukemia, myeloproliferative disorders, myelodysplastic syndromes, multiple myeloma, non-Hodgkin lymphoma, Hodgkin disease, aplastic anemia, pure red cell aplasia, paroxysmal nocturnal hemoglobinuria, Fanconi anemia, Thalassemia major, sickle cell anemia, Severe combined immunodeficiency (SCID), Wiskott-Aldrich syndrome, hemophagocytic lymphohistiocytosis (HLH), inborn errors of metabolism (e.g., mucopolysaccharidosis, Gaucher disease, metachromatic leukodystrophies and adrenoleukodystrophies).

Kits

The present disclosure additionally comprises a kit comprising one or more of the following:
(i) a CD83 binding protein of the disclosure or expression construct(s) encoding same;
(ii) a cell of the disclosure; or
(iii) a pharmaceutical composition of the disclosure.

In the case of a kit for detecting CD83, the kit can additionally comprise a detection means, for example, linked to a CD83 binding protein of the disclosure.

In the case of a kit for therapeutic/prophylactic use, the kit can additionally comprise a pharmaceutically acceptable carrier.

Optionally a kit of the disclosure is packaged with instructions for use in a method described herein according to any example.

The present disclosure includes the following non-limiting Examples.

EXAMPLES

Example 1 Isolation of Human Fab's Specific for hCD83-his 1.1 Phage Display Library The phage display library was prepared in the phagemid vector pCES1 essentially as described (de Haard et al., *J. Biol. Chem*, 1999). The final phage library was titrated to >$10^{12}$/ml.

1.2 Selection of Human Fab's from the Phage Display Library

The ectodomain of human CD83 was cloned into a vector containing a 6× Histidine tag (HIS) for mammalian cell expression (Munster et al., *Int. Immunol.*, 2004; Dudziak et al., *J. Immunol.*, 2005).

CD83-His (10 μg/ml) was incubated overnight in a Maxisorp microtiter plate, washed three times with PBS, tapped dry and blocked with PBS containing 5% milk powder for 2 hours at room temperature. The phage display library was pre-incubated with PBS/milk powder for 15 minutes. The coated, blocked wells were washed in PBS and the phage display library incubated for 1-2 hours.

Unbound Fab's were removed by washing four times with PBS. Bound Fab's were eluted by addition of 1 ml 0.1M Glycine pH2.2 for 10 minutes and eluted phage was equilibrated with 1.5M Tris.

A stationary culture of log phase TG1 cells were re-infected with phage for 30 minutes at 37° C. The culture was rescued by addition of $10^{13}$ helper phage for 30 minutes at 37° C. The re-infected rescued culture was amplified by addition of 2YT/Carb/Kan, incubated overnight at 37° C., centrifuged (8000 rpm; 10 minutes) and supernatant removed for PEG precipitation. PEG solution was added, mixed and incubated on ice at 4° C. for 2 hours. The mixture was centrifuged (10,000 rpm; 30 minutes) and the phage pellet resuspended in 1 ml of PBS. Multiple rounds of panning were performed and the amount of CD83 antigen for subsequent rounds was reduced to 5 μg/ml. The washing stringency was increased per round (six PBS containing 0.1% Tween20 (PBST) washes for round 2; ten in round 3; 15 in round 4) to isolate higher affinity Fab's specific for CD83 from the phage display library.

An increased number of bound phage was detected after the fourth round of panning (FIG. 1) with low binding to a non-specific antigen, indicating clones in round four have a high reactivity to hCD83-His.

Example 2 Identification of Monoclonal hFab's Specific for CD83-his 2.1 Single Clone ELISA Phage pools were incubated with log-phase TG1 cells and plated onto 2YT/Carb/2% Glu solid media (2YTmedia containing 15 g bactoagar). Single colonies were picked and used to inoculate 2YT/Carb/2% Glu media, and incubated shaking overnight at 37° C. Overnight cultures were used to inoculate 2YT/Carb media and cultures were grown to log-phase, allowed to settle and phage rescued by addition of helper phage. Rescued phage preparations were used to inoculate fresh 2YT/Carb/Kan cultures and incubated 37° C. overnight in a shaking incubator. Phage was harvested by centrifugation and PEG precipitation. Pellets were resuspended in PBS.

Binding of individual phage clones was determined by an ELISA assay. Wells of a maxisorp microtitre plate were coated with CD83-His, 9E10 (anti-Myc tag) and a control antigen, for 1 hour, then washed with PBS. Wells were blocked with PBS containing 5% milk powder for 2 hours, washed twice with PBS and phage preparations incubated for 1 hour on the plate shaker. The plate was washed with PBST and goat anti-human kappa chain antibody conjugated to horse radish peroxidise (HRP; Bethyl labs, US) at 0.25 μg/ml in PBST added for 1 hour shaking. The plate was washed five times with PBST and once with PBS. The ELISA was developed by addition of 3,3',5,5'-Tetramethylbenzidine (TMB, Pierce) and the reaction stopped by addition of 2M $H_2SO_4$. Absorbance readings were measured at 450 nM (Spectromax).

Single clones were found to be highly reactive to both CD83-His and CD83-Fc and did not react with an irrelevant Fc-tagged antigen.

2.2 DNA Sequencing

Variable regions for both the heavy chain ($V_H$) and kappa light chain ($V_L$) were PCR amplified using primers against the 5' and 3' framework regions of each chain. PCR products were purified using Qiagen PCR clean up kit.

DNA sequencing revealed clone 1F7 was the dominant clone selected. A further 3 clones with different sequences were isolated, but these had lower binding when compared with 1F7 to CD83-His.

Example 3 Analysis of Clone hFab 1F7

3.1 Sub-Cloning to pGC *E. coli* Expression Vector

Cultures were incubated overnight in a shaking incubator (37° C.) in LB/Carb (LB: 10 g Tryptone, 5 g Yeast extract, 10 g Sodium chloride pH 7.5) and DNA isolated using a Qiagen Miniprep kit. DNA was digested with AflIII and NotI, purified using a Qiagen gel extraction kit, ligated with the *E. coli* expression vector pGC and transformed into chemically competent *E. coli* XL1blue cells according manufacturers protocol (Stratagene). Cells were pelleted and plated on 2YT/Carb/2% Glu plates. Colonies were PCR amplified, DNA extracted using a Qiagen Miniprep kit and sequence verified.

3.2 Expression of hFab Clones

Fab's were transformed into TG1 cells for protein expression. 2YT/Carb/2% Glu media was inoculated and cultured in a shaking incubator overnight at 37° C. until late log phase (OD600 approx 0.9-1.0). 1 mM Isopropyl thiogalactose (IPTG) and fresh antibiotic were added and incubation continued overnight in a shaking incubator at 30° C. The cultures were centrifuged (8000 rpm; 10 minutes) and supernatant removed. Pellets were resuspended in cold periplasmic extraction buffer (0.1M Tris, 20% sucrose, 1 mM EDTA pH8) containing a complete protease inhibitor cocktail (Roche) for 30 minutes on ice. The extract was centrifuged (15,000 rpm; 15 minutes) and supernatant filtered.

3.3 Purification of hFab's a) Affinity Purification Using Ni-NTA

Periplasmic extracts were purified using Ni-NTA agarose (Qiagen) affinity chromatography via the 6× Histidine tag at the C-terminus of the hFab. Periplasmic extracts were dialysed into PBS then diluted in PBS with 0.5M sodium chloride (PBS/NaCl) and incubated with pre-washed resin for 1-2 hours or overnight at 4° C. on a rotator. The mixture was poured into an empty column and allowed to flow through. The column was eluted in a competitive step-wise manner by adding increasing concentrations of Imidazole (20 mM, 50 mM and 250 mM). The column was washed with 30-50 mls PBS/NaCl containing 20 mM Imidazole, followed by 50 mM Imidazole and finally 250 mM Imiadazole. All fractions were collected and analysed by SDS PAGE. Fractions containing purified hFab were dialysed into PBS with 3 buffer changes and concentrated using a Centricon concentrator 10 kDa cut-off (Millipore).

b) Gel Filtration of hFab's

Gel filtration chromatography was performed on hFab's using an FPLC 200 ml Superose S-200HR (GE) column run in PBS at 0.4 ml/minute on an Agilent FPLC. Fractions were collected and analysed for purity on SDS PAGE. Fractions containing pure hFab were pooled and concentrated.

Correct folding and purity of the $V_H$ and $V_L$ chains was verified by SDS PAGE gel and the identity of the hFab was determined by western blot by detecting the kappa light chain, and the heavy chain via the His tag and the myc tag at the expected hFab molecular weight.

The reactivity of purified hFab 1F7 to CD83 was analysed by ELISA. Dilutions of the hFab were allowed to react with CD83-His and the binding curve is shown in FIG. 2A. To further analyse the specificity of hFab 1F7 an ELISA was performed (FIG. 2B), the binding data shows that hFab 1F7 is highly specific binding only to CD83-His and CD83-Fc and is not reactive with the other control antigens.

3.4 Cell Surface Binding Analysis of 1F7 hFab

Cell surface CD83 binding specificity of 1F7 hFab an assay was determined by measuring binding and competitive blocking with soluble CD83. 1F7 Fab was pre-mixed with secondary antibody FITC conjugated goat anti-human IgG, F(ab')2 specific (Jacksons Immunoresearch labs) to obtain a 2:1 molar ratio. The mixture was incubated on ice for 30 mins.

Pre-mixing hFab 1F7 with the secondary FITC anti-human antibody allowed crosslinking of the hFab which resulted in a high fluorescence level shown in FIG. 3 (nil blocking trace) by a shift to the right compared with the no hFab filled trace.

A 5 fold molar excess of soluble hCD83-Fc or hCD83-His relative to Fab was added for 30 mins on ice. KMH2 cells (Hock et al., Int. Immunol. 2001) were pelleted (1000 g; 2 mins), and added to the Fab/secondary IgG/soluble CD83 mix and incubated for 30 mins on ice. The reactions were washed twice and re-pelleted. The cell pellets were resuspended and the binding analysed by FACS.

When hCD83-Fc or hCD83-His was incubated with the cells/antibody mix this blocked the fluorescence signal by up to 95%. Mouse CD83 blocked the fluorescence signal slightly resulting in intermediate quenching and a slight shift in the trace to the left. The soluble CD83 competes for antibody binding and quenches the fluorescence indicating highly specific binding for CD83 (FIG. 3). The controls omitted the 1F7 Fab and as a result the trace showed background levels of fluorescence indicating little non-specific binding.

Example 4 Affinity Maturation of Clone hFab 1F7

Affinity maturation of Fabs was performed by the process of light chain shuffling essentially as described (Marks et al., Nature Biotech. 1992). The $V_H$ chain library was sequentially digested with SfiI and NotI restriction enzymes and replaced by 1F7$V_H$ clone.

Figure 5:
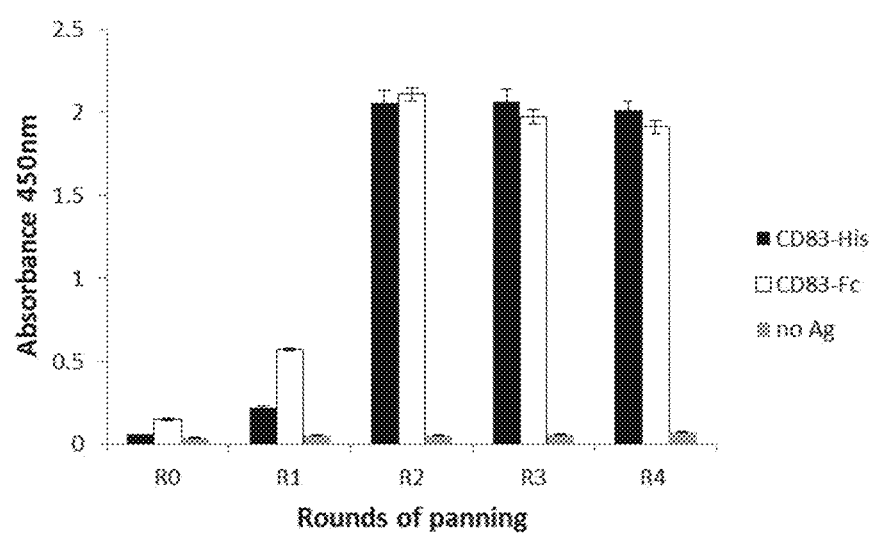
FIG. 5 is a graphical representation of enrichment of higher affinity clones by light chain shuffling as determined by ELISA. Enrichment in the binding to CD83-His was observed after 2 rounds of panning with further increases in binding in round 3 and 4. Analysis was performed in duplicate; error bars indicate ranges of individual values.

Titration of the light chain shuffled library resulted in a final library size of >1×10$^7$. The library was expanded to 10$^{13}$/ml for panning and 4 rounds of selection on CD83-His were performed to isolate higher affinity clones. Individual clones from round 4 were DNA sequenced (FIG. 4). Phages from rounds 2-4 reacted strongly to CD83-His and CD83-Fc by ELISA (FIG. 5) with no cross-reactivity to no-antigen wells.

All clones showed higher relative binding when compared directly to the native clone 1F7. Eleven clones were subcloned into the E. coli expression vector pGC. Eight clones were expressed as hFab's in the E. coli periplasm and analysed for binding to CD83-Fc. Several clones showed superior levels of binding when compared with wild type 1F7.

Normalising the levels of expressed protein i.e. correcting for equivalent levels of binding to 9E10 and corresponding reactivity to CD83 was performed. The highest three hFab binders 4.4, 4.8 and 4.5 were expressed and purified to high purity using Ni-NTA affinity and gel filtration chromatography as previously described.

Affinity maturation was measured by surface Plasmon resonance (SPR) using the ProteOn XPR36™ instrument (BioRad). Individual channels of a GLC chip were coupled with the CD83-His ligand at 3 μg/ml in 0.1M sodium acetate buffer pH 4.5 using amine coupling according to the manufacturer's instructions. Five dilutions of analyte hFab were prepared in PBS containing 0.005% Tween20 (running buffer) and allowed to flow over the coupled CD83 at 30 sec/min flow rate for 300 seconds to evaluate the "on rate" (ka). This was followed by flow with the running buffer for 600 seconds to evaluate the "off rate" (kd). This process was repeated until the analyte dilution series allowed a good kinetic fit using the Langmuir statistical model for analysing the ka and kd, where the affinity constant (KD) is the kd/ka. The best fit data was analysed using the ProteOn software measured by Chi2, where the lowest value is the best fit of the model to the SPR binding curves.

The light chain shuffling process for affinity maturation was successful as the affinity constants of a mutant clone was shown to be approximately 25-fold higher than for the wildtype non-matured Fab 1F7.

Example 5 Reformatting hFab Clones to IgG1 and IgG4

The affinity matured hFab $V_L$ and $V_H$ genes were subcloned into the plasmids pFUSEss-CHIg-hG1, pFUSEss- CHIg-hG4 and pFUSE2ss-CLIg-hk (InvivoGen) for generation of whole human IgG1 and IgG4 antibodies. Fragments were PCR amplified using primers designed to introduce relevant restriction sites into the N' and C' terminal ends of the variable heavy ($V_H$) or variable light ($V_L$) chains. Example primers for reformatting the $V_H$ chain were: pFUSE $V_H$ 4.4 For 5'-GAATTCGGAGGTCCAGCTGGTA-CAG-3' (SEQ ID NO:47) and pFUSE $V_H$ 4.4 Rev 5'-GCTAGCGCTTGAGACGGTGACCGTGG-3' (SEQ ID NO:48), and for reformatting the light chain: pFUSE $V_L$ 4.4 For 5'-GAATTCAGATGTTGTGATGACTCAGTCTC-CAC-3' (SEQ ID NO:49) and pFUSE $V_L$ 4.4 Rev 5'-CGTACGTTTGATTTCCACCTT GGTCCCTTGG-3' (SEQ ID NO:50).

Plasmids and PCR products were digested and ligated as previously described. Ligation products were transformed into chemically competent DH5α cells by standard heat shock method. For $V_H$ cloning low salt LB agar (10 g Tryptone, 5 g Yeast extract, 5 g sodium chloride, 15 g bactoagar) with Zeocin resistance (25 μg/ml) was used for plating transformed colonies and for $V_L$ low salt LB agar with Blasticidin S resistance at 10 μg/ml.

The invention claimed is:

1. A CD83 binding protein comprising an antigen binding domain which specifically binds to CD83, wherein the binding protein comprises:
three heavy chain complementarity determining regions ($V_H$ CDRs) comprising amino acid sequences as shown in SEQ ID NO:3 ($V_H$ CDR1), SEQ ID NO:4 ($V_H$ CDR2), and SEQ ID NO:5 ($V_H$ CDR3); and
(i) three light chain complementarity determining regions ($V_L$ CDRs) comprising amino acid sequences as shown in SEQ ID NO:51 ($V_L$ CDR1), SEQ ID NO:52 ($V_L$ CDR2), and SEQ ID NO:53 ($V_L$ CDR3); or
(ii) three light chain complementarity determining regions ($V_L$ CDRs) comprising amino acid sequences as shown in SEQ ID NO:54 ($V_L$ CDR1), SEQ ID NO:55 ($V_L$ CDR2), and SEQ ID NO:56 ($V_L$ CDR3); or
(iii) three light chain complementarity determining regions ($V_L$ CDRs) comprising amino acid sequences as shown in SEQ ID NO:57 ($V_L$ CDR1), SEQ ID NO:58 ($V_L$ CDR2), and SEQ ID NO:59 ($V_L$ CDR3); or
(iv) three light chain complementarity determining regions ($V_L$ CDRs) comprising amino acid sequences as shown in SEQ ID NO:60 ($V_L$ CDR1), SEQ ID NO:61 ($V_L$ CDR2), and SEQ ID NO:62 ($V_L$ CDR3); or
(v) three light chain complementarity determining regions ($V_L$ CDRs) comprising amino acid sequences as shown in SEQ ID NO:63 ($V_L$ CDR1), SEQ ID NO:64 CDR2), and SEQ ID NO:65 ($V_L$ CDR3); or
(vi) three light chain complementarity determining regions ($V_L$ CDRs) comprising amino acid sequences as shown in SEQ ID NO:66 ($V_L$ CDR1), SEQ ID NO:67 CDR2), and SEQ ID NO:68 ($V_L$ CDR3); or
(vii) three light chain complementarity determining regions ($V_L$ CDRs) comprising amino acid sequences as shown in SEQ ID NO:69 ($V_L$ CDR1), SEQ ID NO:70 CDR2), and SEQ ID NO:71 ($V_L$ CDR3); or
(viii) three light chain complementarity determining regions ($V_L$ CDRs) comprising amino acid sequences as shown in SEQ ID NO:72 ($V_L$ CDR1), SEQ ID NO:73 CDR2), and SEQ ID NO:74 ($V_L$ CDR3); or
(ix) three light chain complementarity determining regions ($V_L$ CDRs) comprising amino acid sequences as shown in SEQ ID NO:75 ($V_L$ CDR1), SEQ ID NO:76 CDR2), and SEQ ID NO:77 ($V_L$ CDR3); or
(x) three light chain complementarity determining regions ($V_L$ CDRs) comprising amino acid sequences as shown in SEQ ID NO:78 ($V_L$ CDR1), SEQ ID NO:79 CDR2), and SEQ ID NO:80 ($V_L$ CDR3); or
(xi) three light chain complementarity determining regions ($V_L$ CDRs) comprising amino acid sequences as shown in SEQ ID NO:81 ($V_L$ CDR1), SEQ ID NO:82 CDR2), and SEQ ID NO:83 ($V_L$ CDR3); or
(xii) three light chain complementarity determining regions CDRs) comprising amino acid sequences as shown in SEQ ID NO:84 ($V_L$ CDR1), SEQ ID NO:85 CDR2), and SEQ ID NO:86 CDR3).

2. The CD83 binding protein of claim 1, wherein the binding protein comprises a heavy chain variable region ($V_H$) and a light chain variable region ($V_L$) in a single polypeptide chain.

3. The CD83 binding protein of claim 2, wherein the binding protein is:
a single chain Fv fragment (scFv); or
(ii) a dimeric scFv (di-scFv); or
(iii) (i) or (ii) linked to a Fc or a heavy chain constant domain ($C_H$2 and/or $C_H$3; or
(iv) (i) or (ii) linked to a protein that binds to an immune effector cell.

4. The CD83 binding protein of claim 1, wherein the binding protein comprises a heavy chain variable region ($V_H$) and a light chain variable region ($V_L$) in separate polypeptide chains.

5. The CD83 binding protein of claim 4, wherein the binding protein is:
(i) a diabody; or
(ii) a triabody; or
(iii) a tetrabody; or
(iv) a Fab; or
(v) a F(ab')2; or
(vi) a Fv; or
(vii) one of (i) to (vi) linked to a Fc or a $C_H$2 and/or $C_H$3; or
(viii) one of (i) to (vi) linked to a protein that binds to an immune effector cell or (IX) an antibody.

6. The CD83 binding protein of claim 5, wherein the binding protein is an antibody.

7. The CD83 binding protein of claim 6, wherein the antibody comprises:
(i) a $V_H$ sequence as shown in amino acids 1 to 115 of SEQ ID NO:2 and a $V_L$ sequence as shown in SEQ ID NO:6; or
(ii) a $V_H$ sequence as shown in amino acids 1 to 115 of SEQ ID NO:2 and a $V_L$ sequence as shown in SEQ ID NO:7; or
(iii) a $V_H$ sequence as shown in amino acids 1 to 115 of SEQ ID NO:2 and a $V_L$ sequence as shown in SEQ ID NO:8; or
(iv) a $V_H$ sequence as shown in amino acids 1 to 115 of SEQ ID NO:2 and a $V_L$ sequence as shown in SEQ ID NO:9; or (v) a $V_H$ sequence as shown in amino acids 1 to 115 of SEQ ID NO:2 and a $V_L$ sequence as shown in SEQ ID NO:10; or (vi) a $V_H$ sequence as shown in amino acids 1 to 115 of SEQ ID NO:2 and a $V_L$ sequence as shown in SEQ ID NO:11; or (vii) a $V_H$ sequence as shown in amino acids 1 to 115 of SEQ ID NO:2 and a $V_L$ sequence as shown in SEQ ID NO:12; or (viii) a $V_H$ sequence as shown in amino acids 1 to 115 of SEQ ID NO:2 and a $V_L$ sequence as shown in SEQ ID NO:13; or (ix) a $V_H$ sequence as shown in amino acids 1 to 115 of SEQ ID NO:2 and a $V_L$ sequence as shown in SEQ ID NO:14; or (x) a $V_H$ sequence as shown in amino acids 1 to 115 of SEQ ID NO:2 and a $V_L$ sequence as shown in SEQ ID NO:15; or (xi) a $V_H$ sequence as shown in amino acids 1 to 115 of SEQ ID NO:2 and a $V_L$ sequence as shown in SEQ ID NO:16; or (xii) a $V_H$ sequence as shown in amino acids 1 to 115 of SEQ ID NO:2 and a $V_L$ sequence as shown in SEQ ID NO:17.

8. The CD83 binding protein of claim 1, wherein the binding protein is a chimeric, de-immunized, humanized, synhumanized, human, primatized, or composite antibody.

9. The CD83 binding protein of claim 1, wherein the binding protein comprises an Fc region capable of inducing an enhanced level of effector function compared to a human IgG1 or IgG4 Fc region and/or an Fc region capable of conferring an extended half-life compared to a human IgG1 or IgG4 Fc region.

10. The CD83 binding protein of claim 1, wherein the binding protein competitively inhibits binding of an antibody to CD83 and/or binds to the same epitope on CD83 as an antibody, wherein the antibody comprises a heavy chain sequence as shown in SEQ ID NO:1 and a light chain sequence as shown in SEQ ID NO:31.

11. A conjugate binding protein comprising the CD83 binding protein of claim 1, wherein the binding protein is conjugated to a compound.

12. The CD83 binding protein of claim 1, wherein the binding protein is a naked binding protein.

13. A composition comprising the CD83 binding protein of claim 1, and a suitable carrier.

14. The composition of claim 13, wherein the carrier is pharmaceutically acceptable.

15. The CD83 binding protein of claim 1, wherein the binding protein comprises:

(i) a $V_H$ sequence as shown in amino acids 1 to 115 of SEQ ID NO:2 and a $V_L$ sequence as shown in SEQ ID NO:6; or (ii) a $V_H$ sequence as shown in amino acids 1 to 115 of SEQ ID NO:2 and a $V_L$ sequence as shown in SEQ ID NO:7; or (iii) a $V_H$ sequence as shown in amino acids 1 to 115 of SEQ ID NO:2 and a $V_L$ sequence as shown in SEQ ID NO:8; or (iv) a $V_H$ sequence as shown in amino acids 1 to 115 of SEQ ID NO:2 and a $V_L$ sequence as shown in SEQ ID NO:9; or (v) a $V_H$ sequence as shown in amino acids 1 to 115 of SEQ ID NO:2 and a $V_L$ sequence as shown in SEQ ID NO:10; or (vi) a $V_H$ sequence as shown in amino acids 1 to 115 of SEQ ID NO:2 and a $V_L$ sequence as shown in SEQ ID NO:11; or (vii) a $V_H$ sequence as shown in amino acids 1 to 115 of SEQ ID NO:2 and a $V_L$ sequence as shown in SEQ ID NO:12; or (viii) a $V_H$ sequence as shown in amino acids 1 to 115 of SEQ ID NO:2 and a $V_L$ sequence as shown in SEQ ID NO:13; or (ix) a $V_H$ sequence as shown in amino acids 1 to 115 of SEQ ID NO:2 and a $V_L$ sequence as shown in SEQ ID NO:14; or (x) a $V_H$ sequence as shown in amino acids 1 to 115 of SEQ ID NO:2 and a $V_L$ sequence as shown in SEQ ID NO:15; or (xi) a $V_H$ sequence as shown in amino acids 1 to 115 of SEQ ID NO:2 and a $V_L$ sequence as shown in SEQ ID NO:16; or (xii) a $V_H$ sequence as shown in amino acids 1 to 115 of SEQ ID NO:2 and a $V_L$ sequence as shown in SEQ ID NO:17.

16. The CD83 binding protein of claim 15, wherein the binding protein comprises a $V_H$ sequence as shown in amino acids 1 to 115 of SEQ ID NO:2 and a $V_L$ sequence as shown in SEQ ID NO:6.

17. The CD83 binding protein of claim 16, wherein the binding protein comprises a heavy chain sequence as shown in SEQ ID NO:1 and a light chain sequence as shown in SEQ ID NO:31.

* * * * *

UNITED STATES PATENT AND TRADEMARK OFFICE
CERTIFICATE OF CORRECTION

PATENT NO. : 10,870,704 B2  
APPLICATION NO. : 15/521124  
DATED : December 22, 2020  
INVENTOR(S) : Joanne L. Casey and Andrew M. Coley Page 1 of 1

It is certified that error appears in the above-identified patent and that said Letters Patent is hereby corrected as shown below:

In the Claims

Claim 1, Column 107, Line 44, "SEQ ID NO:64 CDR2)" should read --SEQ ID NO:64 ($V_L$ CDR2)--.

Claim 1, Column 107, Lines 48-49, "SEQ ID NO:67 CDR2)" should read --SEQ ID NO:67 ($V_L$ CDR2)--.

Claim 1, Column 107, Lines 52-53, "SEQ ID NO:70 CDR2)" should read --SEQ ID NO:70 ($V_L$ CDR2)--.

Claim 1, Column 107, Lines 56-57, "SEQ ID NO:73 CDR2)" should read --SEQ ID NO:73 ($V_L$ CDR2)--.

Claim 1, Column 107, Lines 60-61, "SEQ ID NO:76 CDR2)" should read --SEQ ID NO:76 ($V_L$ CDR2)--.

Claim 1, Column 107, Line 64, "SEQ ID NO:79 CDR2)" should read --SEQ ID NO:79 ($V_L$ CDR2)--.

Claim 1, Column 108, Lines 18-19, "SEQ ID NO:82 CDR2)" should read --SEQ ID NO:82 ($V_L$ CDR2)--.

Claim 1, Column 108, Line 21, "regions CDRs)" should read --regions ($V_L$ CDRs)--.

Claim 1, Column 108, Lines 22-23, "SEQ ID NO:85 CDR2)" should read --SEQ ID NO:85 ($V_L$ CDR2)--.

Signed and Sealed this  
Sixth Day of April, 2021

Drew Hirshfeld  
*Performing the Functions and Duties of the*  
*Under Secretary of Commerce for Intellectual Property and*  
*Director of the United States Patent and Trademark Office*